US011103578B2

(12) United States Patent
Ciaramella et al.

(10) Patent No.: US 11,103,578 B2
(45) Date of Patent: *Aug. 31, 2021

(54) RESPIRATORY VIRUS NUCLEIC ACID VACCINES

(71) Applicant: ModernaTX, Inc., Cambridge, MA (US)

(72) Inventors: Giuseppe Ciaramella, Sudbury, MA (US); Sunny Himansu, Winchester, MA (US)

(73) Assignee: ModernaTX, Inc., Cambridge, MA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/467,142

(22) PCT Filed: Dec. 8, 2017

(86) PCT No.: PCT/US2017/065408
§ 371 (c)(1),
(2) Date: Jun. 6, 2019

(87) PCT Pub. No.: WO2018/107088
PCT Pub. Date: Jun. 14, 2018

(65) Prior Publication Data
US 2020/0069794 A1 Mar. 5, 2020

Related U.S. Application Data

(60) Provisional application No. 62/431,775, filed on Dec. 8, 2016.

(51) Int. Cl.
| | | |
|---|---|---|
| A61K 39/295 | (2006.01) | |
| A61K 31/7105 | (2006.01) | |
| A61K 31/7115 | (2006.01) | |
| A61K 38/16 | (2006.01) | |
| C12N 15/86 | (2006.01) | |
| A61K 9/51 | (2006.01) | |
| A61K 47/26 | (2006.01) | |
| A61K 9/00 | (2006.01) | |
| A61K 39/00 | (2006.01) | |

(52) U.S. Cl.
CPC .......... *A61K 39/295* (2013.01); *A61K 9/0051* (2013.01); *A61K 9/5146* (2013.01); *A61K 31/7105* (2013.01); *A61K 31/7115* (2013.01); *A61K 38/164* (2013.01); *A61K 47/26* (2013.01); *C12N 15/86* (2013.01); *A61K 9/0019* (2013.01); *A61K 2039/53* (2013.01); *A61K 2039/55511* (2013.01); *A61K 2039/6081* (2013.01); *C12N 2760/18334* (2013.01); *C12N 2760/18521* (2013.01); *C12N 2760/18534* (2013.01); *C12N 2760/18634* (2013.01)

(58) Field of Classification Search
CPC .... A61K 39/295; A61K 9/0051; A61K 47/26; A61K 9/5146; A61K 31/7105; A61K 31/7115; A61K 38/164; A61K 9/0019; A61K 2039/53; A61K 2039/55511; A61K 2039/6081; A61K 2039/6018; A61K 39/12; C12N 15/86; C12N 2760/18634; C12N 2760/18534; C12N 2760/18521; C12N 2760/18334; A61P 31/14; A61P 31/16

See application file for complete search history.

(56) References Cited

U.S. PATENT DOCUMENTS

| | | | |
|---|---|---|---|
| 3,906,092 | A | 9/1975 | Hilleman et al. |
| 4,790,987 | A | 12/1988 | Compans et al. |
| 5,169,628 | A | 12/1992 | Wathen |
| 5,427,782 | A | 6/1995 | Compans et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 6,610,044 | B2 | 8/2003 | Mathiesen |
| 7,001,890 | B1 | 2/2006 | Wagner et al. |
| 7,208,161 | B1 | 4/2007 | Murphy et al. |
| 7,449,324 | B2 | 11/2008 | Fouchier et al. |
| 7,531,342 | B2 | 5/2009 | Fouchier et al. |
| 7,671,186 | B2 | 3/2010 | Klein et al. |
| 7,704,720 | B2 | 4/2010 | Tang et al. |
| 8,217,016 | B2 | 7/2012 | Hoerr et al. |
| 8,252,289 | B2 | 8/2012 | Eleouët et al. |
| 8,569,256 | B2 | 10/2013 | Heyes et al. |
| 8,609,142 | B2 | 12/2013 | Troiano et al. |

(Continued)

FOREIGN PATENT DOCUMENTS

| | | |
|---|---|---|
| AU | 652831 B2 | 9/1994 |
| CA | 2473135 | 6/2003 |

(Continued)

OTHER PUBLICATIONS

Schmidt AC, Schaap-Nutt A, Bartlett EJ, Schomacker H, Boonyaratanakornkit J, Karron RA, Collins PL. Progress in the development of human parainfluenza virus vaccines. Expert Rev Respir Med. Aug. 2011;5(4):515-26.*

(Continued)

*Primary Examiner* — Rachel B Gill

(74) *Attorney, Agent, or Firm* — Wolf, Greenfield & Sacks, P.C.

(57) ABSTRACT

Provided herein, in some embodiments, are vaccines (and vaccination methods) that include a ribonucleic acid (RNA) polynucleotide encoding a human metapneumovirus (hMPV) F protein and a RNA polynucleotide encoding a human parainfluenza virus 3 (hPrV3) F protein.

28 Claims, 19 Drawing Sheets

Specification includes a Sequence Listing.

(56) References Cited

U.S. PATENT DOCUMENTS

| | | |
|---|---|---|
| 8,613,954 B2 | 12/2013 | Zale et al. |
| 8,617,608 B2 | 12/2013 | Zale et al. |
| 8,710,200 B2 | 4/2014 | Schrum et al. |
| 8,722,341 B2 | 5/2014 | Fouchier et al. |
| 8,734,832 B2 | 5/2014 | O'Hagan et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,841,433 B2 | 9/2014 | Fouchier et al. |
| 8,889,146 B2 | 11/2014 | Blais et al. |
| 8,927,206 B2 | 1/2015 | De Jong et al. |
| 8,999,380 B2 | 4/2015 | Bancel et al. |
| 9,192,661 B2 | 11/2015 | Jain et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,376,726 B2 | 6/2016 | Fouchier et al. |
| 9,464,124 B2 | 10/2016 | Bancel et al. |
| 9,512,456 B2 | 12/2016 | Wang et al. |
| 9,567,653 B2 | 2/2017 | Fouchier et al. |
| 9,597,380 B2 | 3/2017 | Chakraborty et al. |
| 9,623,095 B2 | 4/2017 | Kallen et al. |
| 9,669,089 B2 | 6/2017 | Thess et al. |
| 9,790,531 B2 | 10/2017 | Wang et al. |
| 9,868,691 B2 | 1/2018 | Benenato et al. |
| 9,872,900 B2 | 1/2018 | Ciaramella et al. |
| 9,937,196 B2 | 4/2018 | Jain et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,273,269 B2 | 4/2019 | Ciaramella |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 2001/0001066 A1 | 5/2001 | Cezayirli et al. |
| 2003/0032615 A1 | 2/2003 | Felgner et al. |
| 2003/0092653 A1 | 5/2003 | Kisich et al. |
| 2003/0232061 A1 | 12/2003 | Fouchier et al. |
| 2004/0005545 A1 | 1/2004 | Fouchier et al. |
| 2004/0096451 A1 | 5/2004 | Young et al. |
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2006/0002958 A1 | 1/2006 | Naylor et al. |
| 2006/0172003 A1 | 8/2006 | Meers et al. |
| 2006/0172966 A1 | 8/2006 | Lipford et al. |
| 2006/0228367 A1 | 10/2006 | Ulbrandt et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2009/0123529 A1 | 5/2009 | Xiaomao |
| 2009/0162395 A1 | 6/2009 | Crowe et al. |
| 2010/0130588 A1 | 5/2010 | Yaworski et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mulbe et al. |
| 2010/0272747 A1 | 10/2010 | Chow et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0135645 A1 | 6/2011 | Williamson et al. |
| 2011/0250225 A1 | 10/2011 | Fotin-Mleczek et al. |
| 2011/0269950 A1 | 11/2011 | Von Der Mulbe et al. |
| 2011/0311472 A1 | 12/2011 | Hoerr et al. |
| 2012/0009221 A1 | 1/2012 | Hoerr et al. |
| 2012/0045471 A1 | 2/2012 | Haller et al. |
| 2012/0189700 A1 | 7/2012 | Aguilar et al. |
| 2012/0219573 A1 | 8/2012 | Baumhof et al. |
| 2012/0258046 A1 | 10/2012 | Mutske |
| 2013/0022538 A1 | 1/2013 | Rossi |
| 2013/0078281 A1 | 3/2013 | He et al. |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0236974 A1 | 9/2013 | De Fougerolles |
| 2013/0243848 A1 | 9/2013 | Lobovkina et al. |
| 2013/0245103 A1 | 9/2013 | de Fougerolles et al. |
| 2013/0245107 A1 | 9/2013 | De Fougerolles et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0024076 A1 | 1/2014 | Tang et al. |
| 2014/0037660 A1 | 2/2014 | Folin-Mleczek et al. |
| 2014/0065228 A1 | 3/2014 | Yarowoski et al. |
| 2014/0134201 A1 | 5/2014 | Tureci et al. |
| 2014/0141042 A1 | 5/2014 | Vitelli et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0271829 A1 | 9/2014 | Lilja et al. |
| 2014/0370497 A1 | 12/2014 | Fouchier et al. |
| 2014/0378538 A1 | 12/2014 | Bancel |
| 2015/0030622 A1 | 1/2015 | Marshall et al. |
| 2015/0051268 A1 | 2/2015 | Bancel et al. |
| 2015/0056253 A1 | 2/2015 | Bancel et al. |
| 2015/0079121 A1 | 3/2015 | Weiner et al. |
| 2015/0093413 A1 | 4/2015 | Thess et al. |
| 2015/0126589 A1 | 5/2015 | Geiger et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0335728 A1 | 11/2015 | Wong et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0039884 A1 | 2/2016 | Li et al. |
| 2016/0151474 A1 | 6/2016 | Kallen et al. |
| 2016/0271272 A1 | 9/2016 | Bancel et al. |
| 2016/0317647 A1 | 11/2016 | Ciaramella et al. |
| 2016/0331828 A1 | 11/2016 | Ciaramella et al. |
| 2017/0065675 A1 | 3/2017 | Bancel et al. |
| 2017/0130255 A1 | 5/2017 | Wang et al. |
| 2017/0202979 A1 | 7/2017 | Chakraborty et al. |
| 2017/0340724 A1 | 11/2017 | Ciaramella et al. |
| 2018/0000953 A1 | 1/2018 | Almarsson et al. |
| 2018/0002393 A1 | 1/2018 | Bancel et al. |
| 2018/0008694 A1 | 1/2018 | Ciaramella et al. |
| 2018/0028645 A1 | 2/2018 | Ciaramella et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |

(56) References Cited

U.S. PATENT DOCUMENTS

| | | |
|---|---|---|
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314493 A1 | 10/2019 | Ciaramella et al. |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |

FOREIGN PATENT DOCUMENTS

| | | |
|---|---|---|
| EP | 1026253 | 8/2000 |
| EP | 1083232 | 2/2005 |
| EP | 1301614 B1 | 11/2006 |
| EP | 1383556 B1 | 10/2007 |
| EP | 1905844 A2 | 2/2008 |
| EP | 2188379 B1 | 1/2013 |
| EP | 2548960 A1 | 1/2013 |
| WO | WO 1987/005326 A1 | 9/1987 |
| WO | WO 1990/011092 A1 | 10/1990 |
| WO | WO 1993/014778 | 8/1993 |
| WO | WO 1995/024485 | 9/1995 |
| WO | WO 1995/026204 | 10/1995 |
| WO | WO 1995/033835 | 12/1995 |
| WO | WO 1998/058956 | 12/1998 |
| WO | WO 1999/033982 | 7/1999 |
| WO | WO 1999/052503 A2 | 10/1999 |
| WO | WO 2001/021810 A1 | 3/2001 |
| WO | WO 2003/072720 A2 | 9/2003 |
| WO | WO 2004/058166 A2 | 7/2004 |
| WO | WO 2004/076645 A1 | 9/2004 |
| WO | WO 2005/007689 A1 | 1/2005 |
| WO | WO 2005/009346 | 2/2005 |
| WO | WO 2005/027825 A2 | 3/2005 |
| WO | WO 2006/056027 A1 | 6/2006 |
| WO | WO 2006/071903 | 7/2006 |
| WO | WO 2006/095259 | 9/2006 |
| WO | WO 2007/038862 A1 | 4/2007 |
| WO | WO 2007/095976 A2 | 8/2007 |
| WO | WO 2008/014979 A3 | 2/2008 |
| WO | WO 2008/043052 | 4/2008 |
| WO | WO 2008/052770 A2 | 5/2008 |
| WO | WO 2008/083949 A2 | 7/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/115046 A2 | 10/2010 |
| WO | WO 2010/149743 A2 | 12/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/144358 A1 | 11/2011 |
| WO | WO 2012/006369 A2 | 1/2012 |
| WO | WO 2012/006378 A1 | 1/2012 |
| WO | WO 2012/006380 A2 | 1/2012 |
| WO | WO 2012/019630 A1 | 2/2012 |
| WO | WO 2012/019780 A1 | 2/2012 |
| WO | WO 2012/030901 A1 | 3/2012 |
| WO | WO 2012/075040 A2 | 6/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A2 | 9/2012 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | WO 2013/052167 A2 | 4/2013 |
| WO | WO 2013/055905 A1 | 4/2013 |
| WO | WO 2013/056132 A2 | 4/2013 |
| WO | WO 2013/059496 A1 | 4/2013 |
| WO | WO 2013/090186 A1 | 6/2013 |
| WO | WO 2013/102203 A1 | 7/2013 |
| WO | WO 2013/113502 A1 | 8/2013 |
| WO | WO 2013/120628 A1 | 8/2013 |
| WO | WO 2013/120629 A1 | 8/2013 |
| WO | WO 2013/174409 A1 | 11/2013 |
| WO | WO 2013/185069 A1 | 12/2013 |
| WO | WO 2014/071963 A1 | 5/2014 |
| WO | WO 2014/072061 A1 | 5/2014 |
| WO | WO 2014/089486 A1 | 6/2014 |
| WO | WO 2014/127917 A1 | 8/2014 |
| WO | WO 2014/152027 A1 | 9/2014 |
| WO | WO 2014/152774 A1 | 9/2014 |
| WO | WO 2014/152940 A1 | 9/2014 |
| WO | WO 2014/160243 A1 | 10/2014 |
| WO | WO 2014/160463 A1 | 10/2014 |
| WO | WO 2015/013551 A1 | 1/2015 |
| WO | WO 2015/024667 A1 | 2/2015 |
| WO | WO 2015/024668 A2 | 2/2015 |
| WO | WO 2015/101414 A2 | 7/2015 |
| WO | WO 2015/101415 A1 | 7/2015 |
| WO | WO 2015/130584 A2 | 9/2015 |
| WO | WO 2015/164674 A1 | 10/2015 |
| WO | WO 2015/189425 A1 | 12/2015 |
| WO | WO 2015/199952 A1 | 12/2015 |
| WO | WO 2016/103238 | 6/2016 |
| WO | WO 2016/164762 A1 | 10/2016 |
| WO | WO 2016/176330 A1 | 11/2016 |
| WO | WO 2016/201377 A1 | 12/2016 |
| WO | WO 2016/203025 A1 | 12/2016 |
| WO | WO 2017/015457 A1 | 1/2017 |
| WO | WO 2017/015463 A1 | 1/2017 |
| WO | WO 2017/019935 A1 | 2/2017 |
| WO | WO 2017/020026 A1 | 2/2017 |
| WO | WO 2017/172890 A1 | 3/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070622 A1 | 4/2017 |
| WO | WO 2017/070623 A1 | 4/2017 |
| WO | WO 2017/070626 A2 | 4/2017 |
| WO | WO 2017/127750 A1 | 7/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |

(56) References Cited

FOREIGN PATENT DOCUMENTS

| WO | WO 2018/053209 A1 | 3/2018 |
|---|---|---|
| WO | WO 2018/075980 A1 | 4/2018 |
| WO | WO 2018/081459 A1 | 5/2018 |
| WO | WO 2018/081462 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |

OTHER PUBLICATIONS

Más V, Rodriguez L, Olmedillas E, Cano O, Palomo C, Terrón MC, Luque D, Melero JA, McLellan JS. Engineering, Structure and Immunogenicity of the Human Metapneumovirus F Protein in the Postfusion Conformation. PLoS Pathog. Sep. 9, 2016;12(9): e1005859.*
Szebeni J, et. al. Adv Drug Deliv Rev. Sep. 16, 2011;63(12):1020-30. Epub Jul. 14, 2011.*
Szebeni J. Mol Immunol. Oct. 2014;61(2):163-73. Epub Aug. 12, 2014.*
Szebeni J, et. al. Biochem Biophys Res Commun. Dec. 18, 2015;468(3):490-7. Epub Jul. 14, 2015. Review.*
Ernsting MJ, et. al. J Control Release. Dec. 28, 2013;172(3):782-94. Epub Sep. 25, 2013.).*
Xue HY, et. al. Curr Pharm Des. 2015;21(22):3140-7.*
Hassett KJ, Benenato KE, Jacquinet E, Lee A, Woods A, Yuzhakov O, et. al. Optimization of Lipid Nanoparticles for Intramuscular Administration of mRNA Vaccines. Mol Ther Nucleic Acids. Apr. 15, 2019;15:1-11. Epub Feb. 7, 2019.*
Chen S, Tam YYC, Lin PJC, Sung MMH, Tam YK, Cullis PR. Influence of particle size on the in vivo potency of lipid nanoparticle formulations of siRNA. J Control Release. Aug. 10, 2016;235:236-244. doi: 10.1016/j.jconrel.2016.05.059. Epub May 26, 2016. PMID: 27238441.*
Leroueil PR, et. al. Nano Lett. Feb. 2008;8(2):420-4. Epub Jan. 25, 2008.*
International Search Report and Written Opinion for Application No. PCT/US2017/065408 dated, Jun. 5, 2018.
[No Author Listed], "Messenger RNA", Internet: Wikipedia. Jun. 19, 2013, XP002699196, Retrieved from the Internet: URL: http://en.wikipedia.org/wiki/Messenger RNA.
Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.
Archer, S.J., Induction of a T-cell specific antigen on bone marrow lymphocytes with thymus RNA. Immunology. Jan. 1978;34(1):123-9.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.
Bettinger, T. et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill, A., et al., Single-step antigen loading and activation of dendritic cells by mRNA electroporation for the purpose of therapeutic vaccination in melanoma patients. Clin Cancer Res. May, 2009; 15(10): 3366-3375.
Bose, S. et al., Role of nucleolin in human parainfluenza virus type 3 infection of human lung epithelial cells. J Viral. Aug. 2004;78(15):8146-58.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Cheng et al., Multifunctional triblock copolymers for intracellular messenger RNA delivery. Biomaterials. Oct. 2012; 33(28): 6868-6876.
Conry, R.M. et al., Characterization of a messenger RNA polynucleotide vaccine vector. Cancer Res. Apr. 1, 1995 ;55 (7):1397-1400.
Cu et al., Enhanced Delivery and Potency of Self-Amplifying mRNA Vaccines by Electroporation in Situ, Vaccines, 2013, 1, 367-383. Abstract Only.
Dahlman, James E. et al., In vivo endothelial siRNA delivery using polymeric nanoparticles with low molecular weight, Nature Nanotechnology, 2014, No vol.#, pp. 1-8.
Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
GenBank Accession No. ABM67072. Submitted to NCBI on Oct. 6, 2006. 1 page.
GenBank Accession No. AHX22069. First seen on NCBI on May 14, 2014. 2 pages.
GenBank Accession No. BAS30426.1 Submitted to NCBI on Sep. 2, 2015. 2 pages.
GenBank Accession No. EF051125. Submitted to NCBI on Oct. 7, 2006.
Gilboa, E. et al., Cancer immunotherapy with mRNA-transfected dendritic cells. Immunol Rev. Jun. 2004;199:251-63.
Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.

(56) References Cited

OTHER PUBLICATIONS

Hajj et al., Tools for translation: non-viral materials for therapeutic mRNA delivery. Nat Rev Mat. Sep. 2017;2:17056.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heiser, A. et al., Induction of polyclonal prostate cancer-specific CTL using dendritic cells transfected with amplified tumor RNA. J lmmunol. Mar. 1, 2001; 166(5):2953-60.
Heyes et al., Cationic lipid saturation influences intracellular delivery of encapsulated nucleic acids. J Control Release. Oct. 3, 2005;107(2):276-87.
Hoerr, I. et al., In vivo application of RNA leads to induction of specific cytotoxic T lymphocytes and antibodies. EurJ lmmunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp et al., Modification of antigen-encoding RNA increases stability, translational efficacy, and T-cell stimulatory capacity of dendritic cells. Blood. Dec. 15, 2006;108(13):4009-17.
Jirikowski, G.F., et al., Reversal of diabetes insipidus in Brattleboro Rats: lntrahypothalamic injection of vasopressin mRNA. Science. Feb. 1992; 255(5047): 996-998.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kalra et al., Virosomes: As a Drug Delivery Carrier. American Journal of Advanced Drug Delivery. 2013;1:29-35.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.
Kozielski et al., Bioreducible cationic polymer-based nanoparticles for efficient and environmentally triggered cytoplasmic siRNA delivery to primary human brain cancer cells. ACS Nano. Apr. 22, 2014;8(4):3232-41. doi: 10.1021/nn500704t. Epub Apr. 3, 2014.
Kreiter, S., et al., lntranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in lmmun. Jun. 2011; 23(3): 399-406.

Kuhn et al., mRNA as a versatile tool for exogenous protein expression. Current Gene Therapy. Oct. 2012; 12 (5): 347-361.
Leitner et al., DNA and RNA-based vaccines: principles, progress and prospects. Vaccine. Dec. 10, 1999;18 (9-10):765-77.
Li, L. et al., Overcoming obstacles to develop effective and safe siRNA therapeutics. Expert Opin Biol Ther. May 2009; 9(5): 609-19.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Lindgren et al., Induction of Robust B Cell Responses after Influenza mRNA Vaccination Is Accompanied by Circulating Hemagglutinin-Specific ICOS+PD-1+CXCR3+ T Follicular Helper Cells. Front Immunol. Nov. 13, 2017;8:1539. doi: 10.3389/fimmu.2017.01539. eCollection 2017.
Lorenzi et al., Intranasal vaccination with messenger RNA as a new approach in gene therapy: Use against tuberculosis. BMC Biotechnol. Oct. 2010; 10(77): 1-11.
MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Martinon et al., Induction of virus-specific cytotoxic T lymphocytes in vivo by liposome-entrapped mRNA. EurJ lmmunol. Jul. 1993;23(7):1719-22.
McKenzie et al., Nucleic acid vaccines: tasks and tactics. lmmunol Res. 2001 ;24(3):225-44.
Midoux et al., Lipid-based mRNA vaccine delivery systems. Expert Rev Vaccines. Feb. 2015;14(2):221-34. doi: 10.1586/14760584. 2015.986104. Epub Dec. 26, 2014. Review.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9):1065-9.
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Muller, M.R. et al., Transfection of dendritic cells with RNA induces CD4- and COB-mediated T cell immunity against breast carcinomas and reveals the immunodominance of presented T cell epitopes. J lmmunol. Jun. 15, 2003;170 (12):5892-6.
Narayanan et al., Interplay between viruses and host mRNA degradation. Biochim Biophys Acta. Jun.-Jul. 2013;1829(6-7):732-41. doi: 10.1016/j.bbagrm.2012.12.003. Epub Dec. 26, 2012.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pollard et al., Type I IFN counteracts the induction of antigen-specific immune responses by lipid-based delivery of mRNA vaccines. Mol Ther. Jan. 2013; 21 (1): 251-259.

(56) References Cited

OTHER PUBLICATIONS

Pulford, B., et al., Liposome-siRNA-peptide complexes cross the blood-brain barrier and significantly decrease PrP'C on neuronal cells and PrP'RES in infected cell cultures. PLoS ONE. 201 O; 5(6): e11085.

Rabinovich, P.M., et al., Synthetic messenger RNA as a tool for gene therapy. Hum. Gene Ther. Oct. 2006; 17: 1027-1035.

Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.

Sahin et al., mRNA-based therapeutics—developing a new class of drugs. Nat Rev Drug Discov. Oct. 2014;13(10):759-80. doi: 10.1038/nrd4278. Epub Sep. 19, 2014.

Schirrmacher et al., Intra-pinna anti-tumor vaccination with self-replicating infectious RNA or with DNA encoding a model tumor antigen and a cytokine. Gene Ther. Jul. 2000;7(13):1137-47.

Schmitt, W.E. et al., In vitro induction of a bladder cancer-specific T-cell response by mRNA-transfected dendritic cells. J Cancer Res Clin Oncol. 2001 ;127(3):203-6.

Schott et al., Viral and non-viral approaches for transient delivery of mRNA and proteins. Current Gene Ther. 2011; 11 (5): 382-398.

Segura, J., et al., Monitoring gene therapy by external imaging of mRNA: Pilot study on murine erythropoietin. Ther Drug Monit. Oct. 2007; 29(5): 612-8.

Smits, E., et al., RNA-based gene transfer for adult stem cells and T cells. Leukemia. 2004; 18: 1898-1902.

Sohn, R.L., et al., In-vivo particle mediated delivery of mRNA to mammalian tissues: ballistic and biological effects. Wound Rep and Regen. Jul.-Aug. 2001; 287-296.

Strong, V.T. et al., Incorporation of beta-globin untranslated regions into a Sindbis virus vector for augmentation of heterologous mRNA expression. Gene Ther. Jun. 1997;4(6):624-7.

Sullenger, BA et al., Emerging clinical applications of RNA. Nature. Jul. 11, 2002;418(6894):252-8.

Tang et al., A host-range restricted parainfluenza virus type 3 (PIV3) expressing the human metapneumovirus (hMPV) fusion protein elicits protective immunity in African green monkeys. Vaccine. Feb. 25, 2005;23(14):1657-67.

Tavernier, G., et al., mRNA as gene therapeutic: How to control protein expression. J. of Controlled Release. Mar. 2011; 150(3): 238-247.

Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.

Vassilev et al., Microparticle-mediated RNA immunization against bovine viral diarrhea virus. Vaccine. Feb. 28, 2001;19(15-16):2012-9.

Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Wong et al., An mRNA vaccine for influenza. Nat Biotechnol. Dec. 2012;30(12):1202-4. doi: 10.1038/nbt.2439.

Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.

Ying et al., Cancer therapy using a self-replicating RNA vaccine. Nat Med. Jul. 1999;5(7):823-7.

Zhou, W.Z. et al., RNA melanoma vaccine: induction of antitumor immunity by human glycoprotein 100 mRNA immunization. Hum Gene Ther. Nov. 1, 1999;10(16):2719-24.

U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/897,734, filed Jun. 10, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 17/127,949, filed Dec. 18, 2020, Ciaramella.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/848,318, filed Apr. 14, 2020, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 16/608,451, filed Oct. 25, 2019, Ciaramella et al.
U.S. Appl. No. 16/788,182, filed Feb. 11, 2020, Panther et al.
U.S. Appl. No. 16/794,318, filed Feb. 19, 2020, Mauger et al.
U.S. Appl. No. 17/145,164, filed Jan. 8, 2021, Giessel et al.
U.S. Appl. No. 17/000,201, filed Aug. 21, 2020, Stewart-Jones et al.
U.S. Appl. No. 17/000,215, filed Aug. 21, 2020, Stewart-Jones et al.

Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.

Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020;5:16. doi: 10.1038/s41541-020-0163-z. eCollection 2020.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.

Reichmuth et al., mRNA Vaccine Delivery Using Lipid Nanoparticles. Ther Deliv. 2016;7(5):319-34. doi: 10.4155/tde-2016-0006.

\* cited by examiner

Fig. 11A

Group 8

HMPV/PIV3-F, Cmpd1, 100ug, 2 doses

Group 9

HMPV/PIV3-HN, Cmpd1, 100ug, 2 doses

- 102
- 103
- 104

RESPIRATORY VIRUS NUCLEIC ACID VACCINES

RELATED APPLICATIONS

This application is a national stage filing under 35 U.S.C. § 371 of international application number PCT/US2017/065408, filed Dec. 8, 2017, which was published under PCT Article 21(2) in English and claims the benefit under 35 U.S.C. § 119(e) of U.S. provisional application No. 62/431,775, filed Dec. 8, 2016, which is incorporated by reference herein in its entirety.

BACKGROUND

Human metapneumovirus (hMPV), discovered in 2001, is a common cause of upper and lower respiratory infections. Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In healthy adults over the age of 65 years, the annual incidence rate of hMPV infection is 1.2/1,000, and 38% of these elderly adults require medical care (compared to 9% of young adults). hMPV infection in elderly adults is a common cause of respiratory infection outbreaks (attack rates 13-30%) in residential care facilities, and hospitalization rates are higher than those for influenza infection occurring in healthy adults over the age of 50 years. For individuals who have an underlying pulmonary disease, hMPV infection is associate with exacerbations of the disease (e.g., COPD), and individuals are twice as likely to have symptomatic disease and requirement for medical care. In immunocompromised individuals, hMPV is responsible for 6% of total respiratory infections in lung transplants and 3% of lower respiratory infections associated with stem cell transplant. hMPV infection is also thought to be associated with acute graft rejection.

Likewise, human parainfluenza virus 3 (hPIV3) is also a common cause of upper and lower respiratory infections. This serotype is the most pathogenic of the four PIV serotypes. Infection of hPIV3 in high risk groups can result in serious lower respiratory infections, including bronchiolitis and/or pneumonia.

SUMMARY

Provided herein, in some embodiments, are ribodeoxynucleic acid (RNA) (e.g., mRNA) vaccine compositions and methods for preventing and/or treating lower respiratory human metapneumovirus (hMPV) and human parainfluenza virus 3 (hPIV3) infections, for example, in infants and young adults, in elderly adults, and in those with underlying respiratory diseases. The hMPV/hPIV3 vaccines of the present disclosure produce proteins inside cells, which in turn are secreted or are active intracellularly. In some instances, RNA (e.g., mRNA) vaccines produce much larger antibody titers and produce immune responses earlier, relative to current anti-viral therapeutic treatments. Without being bound by theory, it is believed that the hMPV/hPIV3 RNA vaccines, as provided here, are better designed to produce the appropriate protein conformation upon translation, as the RNA vaccines co-opt natural cellular machinery. Unlike traditional vaccines, which are manufactured ex vivo and may trigger unwanted cellular responses, RNA vaccines are presented to the cellular system in a more native fashion.

Surprisingly, administration of the hMPV/hPIV3 vaccine of the disclosure induces high neutralizing antibody titers and reduced viral load, but does not result in alveolitis or interstitial pneumonia.

Some embodiments of the present disclosure provide a vaccine, comprising (a) a ribonucleic acid (RNA) polynucleotide encoding a human metapneumovirus (hMPV) antigenic polypeptide comprising the amino acid sequence identified by SEQ ID NO:7 or an amino acid sequence that is at least 95% identical to the amino acid sequence identified by SEQ ID NO:7, and (b) a RNA polynucleotide encoding human parainfluenza virus 3 (hPIV3) antigenic polypeptide comprising the amino acid sequence identified by SEQ ID NO:8 or an amino acid sequence that is at least 95% identical to the amino acid sequence identified by SEQ ID NO:8.

Some embodiments of the present disclosure provide a vaccine, comprising (a) a RNA polynucleotide comprising a nucleic acid sequence identified by SEQ ID NO:4 encoding a hMPV antigenic polypeptide or an amino acid sequence that is at least 95% identical to the amino acid sequence identified by SEQ ID NO:4 encoding a hMPV antigenic polypeptide and (b) a RNA polynucleotide comprising a nucleic acid sequence identified by SEQ ID NO:5 encoding a hPIV3 antigenic polypeptide or an amino acid sequence that is at least 95% identical to the amino acid sequence identified by SEQ ID NO:5 encoding a hPIV3 antigenic polypeptide.

In some embodiments, the RNA polynucleotides of (a) and (b) are formulated in a lipid nanoparticle comprising a cationic lipid, a PEG-modified lipid, a sterol and a non-cationic lipid.

In some embodiments, the vaccine comprises (a) a RNA polynucleotide comprising the nucleic acid sequence identified by SEQ ID NO:4 encoding a hMPV antigenic polypeptide and (b) a RNA polynucleotide comprising the nucleic acid sequence identified by SEQ ID NO:5 encoding a hPIV3 antigenic polypeptide. In some embodiments, the vaccine includes a 5' UTR, a 3' UTR, a polyA tail (e.g., 100 nucleotides), a cap (e.g., 7mG(5')ppp(5')NlmpNp), or any combination of two or more of the foregoing components. In some embodiments, the 5' UTR comprises a sequence identified by SEQ ID NO:12. In some embodiments, the 3' UTR comprises a sequence identified by SEQ ID NO:13. Other known UTR sequences may be used. In some embodiments, the RNA polynucleotide of (a) and/or (b) is chemically modified (e.g., comprises 1-methylpseudouridine modifications). In some embodiments, the vaccine comprises (a) a RNA polynucleotide comprising the nucleic acid sequence identified by SEQ ID NO:14 encoding a hMPV antigenic polypeptide and (b) a RNA polynucleotide comprising the nucleic acid sequence identified by SEQ ID NO:15 encoding a hPIV3 antigenic polypeptide. In some embodiments, the vaccine is formulated in a lipid nanoparticle, such as a cationic lipid nanoparticles. In some embodiments, the cationic lipid nanoparticle comprises a mixture of: Compound 1 lipids; 1,2-dimyristoyl-sn-glycerol, methoxypolyethyleneglycol (PEG2000-DMG); 1,2-distearoyl-sn-glycero-3-phosphocholine (DSPC); and cholesterol. In some embodiments, the vaccine comprises a 12.5 µg-200 12.5 µg dose of the RNA polynucleotide of (a) and a 12.5 µg-200 12.5 µg dose of the RNA polynucleotide of (b).

In some embodiments, the vaccine comprises (a) a RNA polynucleotide comprising a the nucleic acid sequence identified by SEQ ID NO:14 encoding a hMPV antigenic polypeptide and (b) a RNA polynucleotide comprising the nucleic acid sequence identified by SEQ ID NO:15 encoding a hPIV3 antigenic polypeptide, wherein the RNA polynucleotide of (a) and the RNA polynucleotide of (b) are co-formulated in a cationic lipid nanoparticle that comprises a mixture of: Compound 1 lipids; 1,2-dimyristoyl-sn-glycerol, methoxypolyethyleneglycol (PEG2000-DMG); 1,2-distearoyl-sn-glycero-3-phosphocholine (DSPC); and cholesterol. In some embodiments, the RNA polynucleotide of (a) and the RNA polynucleotide of (b) are formulated in separate cationic lipid nanoparticles that comprises a mixture of: Compound 1 lipids; 1,2-dimyristoyl-sn-glycerol, methoxypolyethyleneglycol (PEG2000-DMG); 1,2-distearoyl-sn-glycero-3-phosphocholine (DSPC); and cholesterol. In some embodiments, the vaccine comprises a 12.5 µg-200 12.5 µg dose of the RNA polynucleotide of (a) and a 12.5 µg-200 12.5 µg dose of the RNA polynucleotide of (b).

In some embodiments, hMPV and/or hPIV3 viral load is undetectable in subjects after challenge with the virus(es) following administration of less than three doses of the vaccine. In some embodiments, hMPV and/or hPIV3 viral load is undetectable in subjects after challenge with the virus(es) following administration of two doses of the vaccine. In some embodiments, hMPV and/or hPIV3 viral load is undetectable in subjects after challenge with the virus(es) following administration of a single dose of the vaccine.

In some embodiments, the anti-hPIV3 neutralizing antibody titer produced in a subject following administration of a dose of the vaccine is at least 3-fold higher than the anti-hPIV3 neutralizing antibody titer produced in a subject following administration of a comparable dose of a vaccine comprising mRNA encoding hPIV3 HN protein.

In some embodiments, the vaccine provides an effective immune response against both hMPV and hPIV3.

In some embodiments, the anti-hPIV3 and/or anti-hMPV neutralizing antibody titer produced in cotton rats following administration of the vaccine is at least 9 on a log base 2 scale, as measured at the 60% reduction end point of virus control.

In some embodiments, the hMPV viral load in the lung and/or nose is below the limit of quantification in subjects following administration of the vaccine and challenge with hMPV.

In some embodiments, the hPIV3 viral load in the lung and/or nose is below the limit of quantification in subjects following administration of the vaccine and challenge with the hPIV3.

In some embodiments, a subject administered the vaccine does not exhibit symptoms of vaccine-enhanced respiratory disease (e.g., alveolitis (cells within the alveolar spaces) or interstitial pneumonia (inflammatory cell infiltration and thickening of alveolar walls)).

In some embodiments, the neutralizing antibody titer against hMPV in a subject following administration of a second dose of the vaccine is increased by 8-10 fold at 14 days post-administration of the second dose.

In some embodiments, the neutralizing antibody titer against hPIV3 in a subject following administration of a second dose of the vaccine is increased by 4-10 fold at 14 days post-administration of the second dose.

Other embodiments of the present disclosure provide a vaccine, comprising a ribonucleic acid (RNA) polynucleotide encoding a human metapneumovirus (hMPV) antigenic polypeptide comprising the amino acid sequence identified by SEQ ID NO:7, wherein the hMPV RNA polynucleotide is formulated in a lipid nanoparticle comprising a cationic lipid, a PEG-modified lipid, a sterol and a non-cationic lipid.

Yet other embodiments of the present disclosure provide a vaccine, comprising a ribonucleic acid (RNA) polynucleotide encoding human parainfluenza virus 3 (hPIV3) antigenic polypeptide comprising the amino acid sequence identified by SEQ ID NO:8, wherein the hPIV3 RNA polynucleotide is formulated in a lipid nanoparticle comprising a cationic lipid, a PEG-modified lipid, a sterol and a non-cationic lipid.

In some embodiments, the vaccine further comprises a RNA polynucleotide encoding a respiratory syncytial virus (RSV) antigenic polypeptide.

In some embodiments, the cationic lipid is an ionizable lipid.

In some embodiments, the sterol is a cholesterol.

In some embodiments, the non-cationic lipid is a neutral lipid.

In some embodiments, the cationic lipid comprises a compound of Formula I. In some embodiments, the compound of Formula I is Compound 3, 18, 20, 25, 26, 29, 30, 60, 108-112, or 122. In some embodiments, the compound of Formula I is Compound 25.

In some embodiments, the lipid nanoparticle comprises a molar ratio of about 20-60% cationic lipid, 0.5-15% PEG-modified lipid, 25-55% sterol, and 25% non-cationic lipid.

In some embodiments, the lipid nanoparticle has a polydispersity value of less than 0.4.

In some embodiments, the lipid nanoparticle has a net neutral charge at a neutral pH value.

In some embodiments, the vaccine is formulated in an effective amount to prevent or treat a lower respiratory hMPV/hPIV3 infection in a subject.

In some embodiments, the effective amount is 5 µg-100 µg of the RNA polynucleotide encoding hMPV antigenic polypeptide and/or 5 µg-100 µg of the RNA polynucleotide encoding hPIV3 antigenic polypeptide. In some embodiments, the effective amount is 12.5 µg of the RNA polynucleotide encoding hMPV antigenic polypeptide and/or 12.5 µg of the RNA polynucleotide encoding hPIV3 antigenic polypeptide. In some embodiments, the effective amount is 25 µg of the RNA polynucleotide encoding hMPV antigenic polypeptide and/or 25 µg of the RNA polynucleotide encoding hPIV3 antigenic polypeptide. In some embodiments, the effective amount is 50 µg of the RNA polynucleotide encoding hMPV antigenic polypeptide and/or 50 µg of the RNA polynucleotide encoding hPIV3 antigenic polypeptide.

In some embodiments, the RNA polynucleotide encoding hMPV antigenic polypeptide and/or the RNA polynucleotide encoding hPIV3 antigenic polypeptide comprises at least one chemical modification.

In some embodiments, the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

In some embodiments, the chemical modification is in the 5-position of the uracil. In some embodiments, the chemical modification is a N1-methylpseudouridine or N1-ethylpseudouridine.

In some embodiments, at least 80% of the uracil in the open reading frame have a chemical modification. In some embodiments, at least 90% of the uracil in the open reading frame have a chemical modification. In some embodiments, 100% of the uracil in the open reading frame have a chemical modification.

In some embodiments, the RNA polynucleotide encoding hMPV antigenic polypeptide and/or the RNA polynucleotide encoding hPIV3 antigenic polypeptide further encodes at least one 5' terminal cap. In some embodiments, the 5' terminal cap is 7mG(5')ppp(5')NlmpNp.

In some embodiments, the vaccine further comprises an adjuvant. In some embodiments, the adjuvant is a flagellin protein or peptide.

Some embodiments provide a method of preventing a lower respiratory human metapneumovirus and/or human parainfluenza virus 3 (hMPV/hPIV3) infection in elderly subjects, comprising administering to a subject who is 65 years of age or older the vaccine of the present disclosure in an effective amount to prevent a lower respiratory hMPV/hPIV3 infection in the subject.

Other embodiments provide a method of treating a lower respiratory human metapneumovirus and/or human parainfluenza virus 3 (hMPV/hPIV3) infection in elderly subjects, comprising administering to a subject who is 65 years of age or older and is infected with hMPV/hPIV3 the vaccine of the present disclosure in an effective amount to treat a lower respiratory hMPV/hPIV3 infection in the subject.

Yet other embodiments provide a method of preventing a lower respiratory human metapneumovirus and/or human parainfluenza virus 3 (hMPV/hPIV3) infection in a child, comprising administering to a subject who is 5 years of age or younger the vaccine of the present disclosure in an effective amount to prevent a lower respiratory hMPV/hPIV3 infection in the subject.

Still other embodiments provide a method of treating a lower respiratory human metapneumovirus and/or human parainfluenza virus 3 (hMPV/hPIV3) infection in a child, comprising administering to a subject who is 5 years of age or younger and is infected with hMPV/hPIV3 the vaccine of the present disclosure in an effective amount to treat a lower respiratory hMPV/hPIV3 infection in the subject. In some embodiments, the subject is between 6 and 12 months of age.

Further embodiments provide a method of preventing a lower respiratory human metapneumovirus and/or human parainfluenza virus 3 (hMPV/hPIV3) infection in subjects having a pulmonary disease, comprising administering to a subject having a pulmonary disease the vaccine of the present disclosure in an effective amount to prevent a lower respiratory hMPV/hPIV3 infection in the subject.

Still further embodiments provide a method of treating a lower respiratory human metapneumovirus and/or human parainfluenza virus 3 (hMPV/hPIV3) infection in subjects having a pulmonary disease, comprising administering to a subject having a pulmonary condition the vaccine of the present disclosure in an effective amount to treat a lower respiratory hMPV/hPIV3 infection in the subject. In some embodiments, the pulmonary condition is associated with is Chronic Obstructive Pulmonary Disease (COPD), asthma, congestive heart failure or diabetes, or any combination thereof.

Some embodiments provide a method of preventing a lower respiratory human metapneumovirus and/or human parainfluenza virus 3 (hMPV/hPIV3) infection in immunocompromised subjects, comprising administering to an immunocompromised subject the vaccine of the present disclosure in an effective amount to prevent a lower respiratory hMPV/hPIV3 infection in the subject.

Other embodiments provide a method of treating a lower respiratory human metapneumovirus and/or human parainfluenza virus 3 (hMPV/hPIV3) infection in immunocompromised subjects, comprising administering to an immunocompromised subject the vaccine of the present disclosure in an effective amount to treat a lower respiratory hMPV/hPIV3 infection in the subject.

In some embodiments, a single dose of the vaccine is administered to the subject. In some embodiments, a booster dose of the vaccine is administered to the subject.

In some embodiments, the efficacy of the vaccine against the hMPV/hPIV3 infection is at least 50% following administration of the booster dose of the vaccine. In some embodiments, the efficacy of the vaccine against the hMPV/hPIV3 infection is at least 60% following administration of the booster dose of the vaccine.

In some embodiments, the efficacy of the vaccine against the hMPV and/or hPIV3 infection is at least 65% following administration of a single dose of the vaccine. In some embodiments, the efficacy of the vaccine against the hMPV and/or hPIV3 infection is at least 70% following administration of a single dose of the vaccine. In some embodiments, the efficacy of the vaccine against the hMPV and/or hPIV3 infection is at least 75% following administration of a single dose of the vaccine.

In some embodiments, the vaccine immunizes the subject against hMPV/hPIV3 for up to 2 years. In some embodiments, the vaccine immunizes the subject against hMPV/hPIV3 for more than 2 years.

Also provided herein is a vaccine, comprising (a) 12.5 µg-200 µg a human metapneumovirus (hMPV) ribonucleic acid (RNA) polynucleotide comprising the nucleic acid sequence identified by SEQ ID NO:4, and (b) 12.5 µg-200 µg a human parainfluenza virus 3 (hPIV3) RNA polynucleotide comprising the nucleic acid sequence identified by SEQ ID NO:5, wherein the RNA polynucleotides of (a) and (b) are formulated in a lipid nanoparticle comprising a Compound 25 of Formula (I), a PEG-modified lipid, a sterol and a non-cationic lipid. In some embodiments, the efficacy of the vaccine against the hMPV/hPIV3 infection is at least 50% following administration of the booster dose of the vaccine. In some embodiments, the efficacy of the vaccine against the hMPV and/or hPIV3 infection is at least 70% following administration of a single dose of the vaccine.

Further provided herein is a use of the vaccine of the present disclosure in the manufacture of a medicament for use in a method of inducing an antigen specific immune response to hMPV/hPIV3 in a subject, the method comprising administering to the subject the vaccine in an amount effective to produce an antigen specific immune response to hMPV/hPIV3 in the subject.

Some embodiments provide a pharmaceutical composition for use in vaccination of a subject comprising an effective dose of the vaccine of the present disclosure, wherein the effective dose is sufficient to produce detectable levels of antigen as measured in serum of the subject at 1-72 hours post administration. In some embodiments, the cut off index of the antigen is 1-2. Some embodiments provide a pharmaceutical composition for use in vaccination of a subject comprising an effective dose of the vaccine of the present disclosure, wherein the effective dose is sufficient to produce detectable levels of antigen as measured in serum of the subject within 14 days hours post administration.

Other embodiments provide a pharmaceutical composition for use in vaccination of a subject comprising an effective dose of the vaccine of the present disclosure, wherein the effective dose is sufficient to produce a 1,000-

10,000 neutralization titer produced by neutralizing antibody against hMPV/hPIV3 antigen as measured in serum of the subject at 1-72 hours post administration. Yet other embodiments provide a pharmaceutical composition for use in vaccination of a subject comprising an effective dose of the vaccine of the present disclosure, wherein the effective dose is sufficient to produce a 1,000-10,000 neutralization titer produced by neutralizing antibody against hMPV/hPIV3 antigen as measured in serum of the subject within 14 days post administration.

Further embodiments provide a vaccine, comprising (a) a human metapneumovirus (hMPV) ribonucleic acid (RNA) polynucleotide comprising the nucleic acid sequence identified by SEQ ID NO:4 or a nucleic acid sequence that is at least 95% identical to the nucleic acid sequence identified by SEQ ID NO:4, and (b) a human parainfluenza virus 3 (hPIV3) RNA polynucleotide comprising the nucleic acid sequence identified by SEQ ID NO:5 or a nucleic acid sequence that is at least 95% identical to the nucleic acid sequence identified by SEQ ID NO:5, wherein the RNA polynucleotides of (a) and (b) are formulated in a lipid nanoparticle comprising a cationic lipid, a PEG-modified lipid, a sterol and a non-cationic lipid.

Still further embodiments provide a vaccine, comprising (a) a human metapneumovirus (hMPV) ribonucleic acid (RNA) polynucleotide encoded by a nucleic acid comprising the nucleic acid sequence identified by SEQ ID NO:1 or a nucleic acid sequence that is at least 95% identical to the nucleic acid sequence identified by SEQ ID NO:1, and (b) a human parainfluenza virus 3 (hPIV3) RNA polynucleotide encoded by a nucleic acid comprising the nucleic acid sequence identified by SEQ ID NO:2 or a nucleic acid sequence that is at least 95% identical to the nucleic acid sequence identified by SEQ ID NO:2, wherein the RNA polynucleotides of (a) and (b) are formulated in a lipid nanoparticle comprising a cationic lipid, a PEG-modified lipid, a sterol and a non-cationic lipid.

BRIEF DESCRIPTION OF THE DRAWINGS

FIG. 1A, left panel, shows a hMPV F protein-positive (fluorescent) cell count for cells transfected with a mock construct. FIG. 1A, right panel, shows a hMPV F protein-positive (fluorescent) cell count for cells transfected with hMPV/hPIV3 vaccine constructs. hMPV F protein was detected using antibodies specific for hMPV F protein (MEP8). FIG. 1A, middle panel, shows fluorescence obtained from untransfected control cells, using only a secondary antibody. FIG. 1B shows the surface expression of hPIV3 F protein in Hela cells detected using antibodies specific for hPIV3 F protein (MAB10207).

FIG. 2A shows viral titers from the nose and lungs of cotton rats challenged with hMPV. FIG. 2B shows viral titers from the nose and lungs of cotton rats challenged with hPIV3. Cotton rats immunized with the mRNA vaccine were protected from hMPV infection and hPIV3 infection.

FIG. 7A shows viral titers from the nose and lungs of African green monkeys challenged with hMPV. FIG. 7B shows viral titers from the nose and lungs of African green monkeys challenged with hPIV3. Sero-negative African green monkeys immunized with 2 doses of the mRNA vaccine were completely protected from hMPV infection and hPIV3 infection.

FIGS. 11A-11B are graphs showing the neutralizing antibody titers against hPIV3 in sero-negative African green monkeys immunized with two 200 µg doses a vaccine containing mRNA having an open reading frame (SEQ ID NO:5) encoding hPIV3 F protein (SEQ ID NO:8) (FIG. 11A) or a vaccine containing mRNA having an open reading frame (SEQ ID NO:6) encoding hPIV3 HN protein (SEQ ID NO:9) (FIG. 11B). The vaccine encoding hPIV3-F protein induced higher neutralizing antibody titers than the vaccine encoding hPIV3-HN. The mRNA vaccines were formulated with Compound 1 lipids.

FIG. 13A shows that 2 doses of 200 µg and 100 µg of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) elicits high levels of hMPV neutralizing antibodies. FIG. 13B shows that a single dose of the hMPVhPIV3 mRNA vaccine boosts hMPV neutralizing antibodies by 8-10 fold in sero-positive African green monkeys.

FIG. 14A shows that 2 doses of 200 µg and 100 µg of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) elicits high levels of hMPV neutralizing antibodies. FIG. 14B shows that a single dose of the hMPV/hPIV3 mRNA vaccine boosts hPIV3 neutralizing antibodies by 4-10 folds in seropositive African green monkeys.

DETAILED DESCRIPTION

Figure 1A:
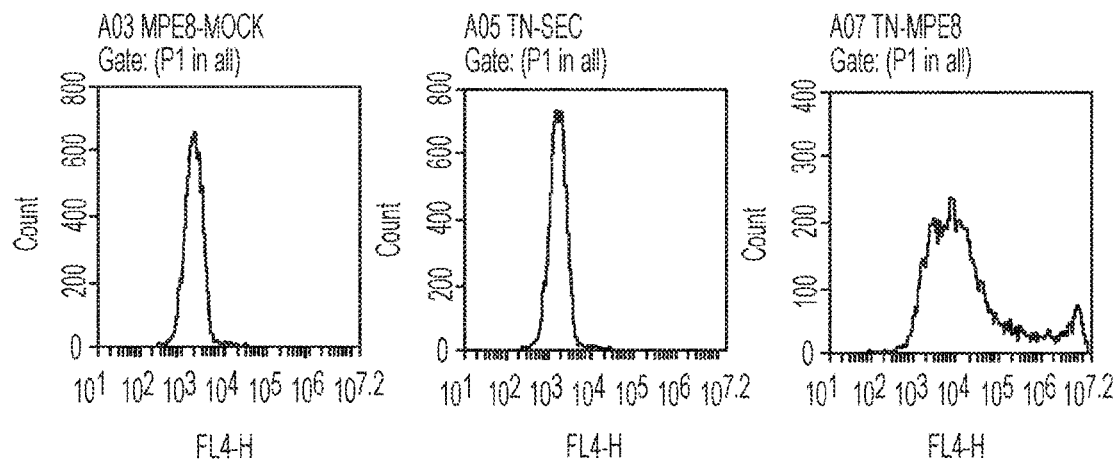
FIGS. 1A-1B are graphs showing that cells transfected with (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) expressed hMPV protein and hPIV3 protein on the cell surface.

The present disclosure provides, in some embodiments, combination vaccine therapies that comprise administering RNA (e.g., mRNA) polynucleotides encoding a human metapneumovirus (hMPV) F protein and a human parainfluenza virus type 3 (hPIV3) F protein, either formulated as a combination vaccine or formulated as single vaccines administered simultaneously or sequentially. In some embodiments, a combination vaccine may further comprise a RNA (e.g., mRNA) polynucleotide encoding a respiratory syncytial virus (RSV) antigenic polypeptide.

Also provided herein are vaccines (vaccine compositions) comprising RNA encoding hMPV F protein and/or hPIV3 F protein, methods of manufacturing these vaccines, and nucleic acids encoding these vaccines.

For simplicity, the term "hMPV/hPIV3" should be understood to encompass hMPV, hPIV3, or both hMPV and hPIV3. "hMPV/hPIV3" compositions contain, for example, a mRNA encoding hMPV, a mRNA encoding hPIV3 as well as one or more additional mRNAs encoding respiratory antigens (e.g., RSV antigens).

The hMPV/hPIV3 RNA (e.g., mRNA) vaccines, in some embodiments, are formulated in a lipid nanoparticle comprising a cationic lipid, a PEG-modified lipid, a sterol and a non-cationic lipid. In some embodiments, the non-cationic lipid is Compound 1 of Formula (I). Thus, in some embodiments, a hMPV/PIV3 RNA vaccine is formulated in a lipid nanoparticle that comprises Compound 1.

In some embodiments, the hMPV/hPIV3 RNA (e.g., mRNA) vaccines may be used to treat a lower respiratory hMPV and/or hPIV3 infection in a child, an elderly person, a young adult, or an immunocompromised person. The hMPV/hPIV3 RNA (e.g., mRNA) vaccines, in some embodiments, may be used to induce a balanced immune response, comprising both cellular and humoral immunity, without many of the risks associated with DNA vaccination. It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the present disclosure are superior to conventional vaccines by a factor of at least 10 fold, 20 fold, 40 fold, 50 fold, 100 fold, 500 fold or 1,000 fold.

In addition, the vaccines of the present disclosure result in effective immune responses against both hMPV and PIV3 (e.g., as measured by a reduction in infectious virus isolated from the nasal and/or lung passages upon exposure to virus), but do not result in visible respiratory pathology (e.g., alveolitis (cells within the alveolar spaces) or interstitial pneumonia (inflammatory cell infiltration and thickening of alveolar walls)). For example, viral load (e.g., as determined by plaque assay and pulmonary histopathology) was evaluated on hematoxylin and eosin (H&E) stained fixed lung sections of vaccinated animals. The sections were evaluated on a 0-4 severity scale and subsequently converted to a 0-100% histopathology scale. The lung histopathology scores were equivalent to the control, indicating no vaccine-enhanced respiratory disease (ERD).

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the present disclosure a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the present disclosure have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the present disclosure do not require viral replication to produce enough protein to result in a strong immune response. Thus, the mRNA of the present disclosure are not self-replicating RNA and do not include components necessary for viral replication.

The present disclosure involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the present disclosure generate a more rapid immune response with fewer doses of antigen than other vaccines tested. The mRNA-LNP formulations of the present disclosure also produce quantitatively and qualitatively better immune responses than vaccines formulated in a different carriers.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the present disclosure are demonstrated herein to generate enhanced IgG levels, sufficient for prophylactic and therapeutic methods rather than transient IgM responses.

hHMPV/hPIV3 RNA Vaccine Compositions

In some embodiments, a vaccine of the present disclosure comprises a RNA (e.g., mRNA) polynucleotide encoding a human metapneumovirus (hMPV) fusion (F) protein. In other embodiments, a vaccine of the present disclosure comprises a RNA (e.g., mRNA) polynucleotide encoding a human parainfluenza virus type 3 (hPIV3) fusion (F) protein. In yet other embodiments, a vaccine of the present disclosure comprises a RNA (e.g., mRNA) polynucleotide encoding a hMPV F protein and a RNA (e.g., mRNA) polynucleotide encoding a hPIV3 F protein.

In some embodiments, the vaccine of the present disclosure comprises a RNA (e.g., mRNA) polynucleotide encoding a hMPV F protein comprising the amino acid sequence identified by SEQ ID NO:7. In some embodiments, a vaccine of the present disclosure comprises a RNA (e.g., mRNA) polynucleotide encoding a hMPV F protein comprising an amino acid sequence that is at least 85% identical to the amino acid sequence identified by SEQ ID NO:7. For example, a vaccine may comprises a RNA (e.g., mRNA) polynucleotide encoding a hMPV F protein comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence identified by SEQ ID NO:7. In some embodiments, a vaccine comprises a RNA (e.g., mRNA) polynucleotide encoding a hMPV F protein comprising an amino acid sequence that is 85%, 86%, 87%, 88%, 89%, 90%, 91%, 92%, 93%, 94%, 95%, 96%, 97%, 98%, or 99% identical to the amino acid sequence identified by SEQ ID NO:7.

In some embodiments, a vaccine of the present disclosure comprises a RNA (e.g., mRNA) polynucleotide comprising the nucleotide sequence identified by SEQ ID NO:4. In some embodiments, a vaccine comprises a RNA (e.g., mRNA) polynucleotide comprising a nucleotide sequence that is at least 85% identical to the nucleotide sequence identified by SEQ ID NO:4. For example, a vaccine may comprise a RNA (e.g., mRNA) polynucleotide comprising a nucleotide sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the nucleotide sequence identified by SEQ ID NO:4. In some embodiments, a vaccine of the present disclosure comprises a RNA (e.g., mRNA) polynucleotide comprising a nucleotide sequence that is 85%, 86%, 87%, 88%, 89%, 90%, 91%, 92%, 93%, 94%, 95%, 96%, 97%, 98%, or 99% identical to the nucleotide sequence identified by SEQ ID NO:4.

In some embodiments, a vaccine of the present disclosure comprises a RNA (e.g., mRNA) polynucleotide encoding a hPIV3 F protein comprising the amino acid sequence identified by SEQ ID NO:8. In some embodiments, a vaccine comprises a RNA (e.g., mRNA) polynucleotide encoding a hPIV3 F protein comprising an amino acid sequence that is at least 85% identical to the amino acid sequence identified by SEQ ID NO:8. For example, a vaccine may comprise a RNA (e.g., mRNA) polynucleotide encoding a hPIV3 F protein comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence identified by SEQ ID NO:8. In some embodiments, a vaccine comprises a RNA (e.g., mRNA) polynucleotide encoding a hPIV3 F protein comprising an amino acid sequence that is 85%, 86%, 87%, 88%, 89%, 90%, 91%, 92%, 93%, 94%, 95%, 96%, 97%, 98%, or 99% identical to the amino acid sequence identified by SEQ ID NO:8.

In some embodiments, a vaccine of the present disclosure comprises a RNA (e.g., mRNA) polynucleotide comprising a nucleotide sequence identified by SEQ ID NO:5. In some embodiments, a vaccine comprises a RNA (e.g., mRNA) polynucleotide comprising a nucleotide sequence that is at least 85% identical to the nucleotide sequence identified by SEQ ID NO:5. For example, a vaccine may comprise a RNA (e.g., mRNA) polynucleotide comprising a nucleotide sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the nucleotide sequence identified by SEQ ID NO:5. In some embodiments, a vaccine comprises a RNA (e.g., mRNA) polynucleotide comprising a nucleotide sequence that is 85%, 86%, 87%, 88%, 89%, 90%, 91%, 92%, 93%, 94%, 95%, 96%, 97%, 98%, or 99% identical to the nucleotide sequence identified by SEQ ID NO:5.

In some embodiments, the RNA (e.g., mRNA) vaccine of the present disclosure comprises a RNA (e.g., mRNA) polynucleotide encoding a hPIV3 hemagglutinin-neuraminidase (UN) comprising the amino acid sequence identified by SEQ ID NO:9. In some embodiments, the RNA (e.g., mRNA) vaccine of the present disclosure comprises a RNA (e.g., mRNA) polynucleotide encoding a hPIV3 hemagglutinin-neuraminidase (HN) comprising an amino acid sequence that is at least 85% identical to the amino acid sequence identified by SEQ ID NO:9. For example, the RNA (e.g., mRNA) vaccine of the present disclosure comprises a RNA (e.g., mRNA) polynucleotide encoding a hPIV3 hemagglutinin-neuraminidase (HN) comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence identified by SEQ ID NO:9. In some embodiments, the RNA (e.g., mRNA) vaccine of the present disclosure comprises a RNA (e.g., mRNA) polynucleotide encoding a hPIV3 hemagglutinin-neuraminidase (HN) comprising an amino acid sequence that is 85%, 86%, 87%, 88%, 89%, 90%, 91%, 92%, 93%, 94%, 95%, 96%, 97%, 98%, or 99% identical to the amino acid sequence identified by SEQ ID NO:9.

In some embodiments, a vaccine of the present disclosure comprises a RNA (e.g., mRNA) polynucleotide comprising a nucleotide sequence identified by SEQ ID NO:6. In some embodiments, a vaccine comprises a RNA (e.g., mRNA) polynucleotide comprising a nucleotide sequence that is at least 85% identical to the nucleotide sequence identified by SEQ ID NO:6. For example, a vaccine may comprise a RNA (e.g., mRNA) polynucleotide comprising a nucleotide sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the nucleotide sequence identified by SEQ ID NO:6. In some embodiments, a vaccine comprises a RNA (e.g., mRNA) polynucleotide comprising a nucleotide sequence that is 85%, 86%, 87%, 88%, 89%, 90%, 91%, 92%, 93%, 94%, 95%, 96%, 97%, 98%, or 99% identical to the nucleotide sequence identified by SEQ ID NO:6.

In some embodiments, a vaccine of the present disclosure is a combination vaccine comprising a RNA (e.g., mRNA) polynucleotide encoding a hMPV F protein and a RNA (e.g., mRNA) polynucleotide encoding a hPIV3 F protein. In some embodiments, a vaccine comprises (a) a RNA (e.g., mRNA) polynucleotide encoding a hMPV F protein comprising the amino acid sequence identified by SEQ ID NO:7 or an amino acid sequence that is at least 90% (e.g., 90%, 91%, 92%, 93%, 94%, 95%, 96%, 97%, 98%, or 99%) identical to the amino acid sequence identified by SEQ ID NO:7, and (b) a RNA polynucleotide encoding a hPIV3 F protein comprising the amino acid sequence identified by SEQ ID NO:8 or an amino acid sequence that is at least 90% (e.g., 90%, 91%, 92%, 93%, 94%, 95%, 96%, 97%, 98%, or 99%) identical to the amino acid sequence identified by SEQ ID NO:8.

In some embodiments, a vaccine of the present disclosure is a combination vaccine comprising (a) a hMPV ribonucleic acid (RNA) polynucleotide comprising the nucleic acid sequence identified by SEQ ID NO:4 or a nucleic acid sequence that is at least 90% (e.g., 90%, 91%, 92%, 93%, 94%, 95%, 96%, 97%, 98%, or 99%) identical to the nucleic acid sequence identified by SEQ ID NO:4, and (b) a hPIV3 RNA polynucleotide comprising the nucleic acid sequence identified by SEQ ID NO:5 or a nucleic acid sequence that is at least 90% (e.g., 90%, 91%, 92%, 93%, 94%, 95%, 96%, 97%, 98%, or 99%) identical to the nucleic acid sequence identified by SEQ ID NO:5.

In some embodiments, a vaccine of the present disclosure is a combination vaccine comprising (a) a hMPV ribonucleic acid (RNA) polynucleotide encoded by a nucleic acid comprising the nucleic acid sequence identified by SEQ ID NO:1 or a nucleic acid sequence that is at least 90% (e.g., 90%, 91%, 92%, 93%, 94%, 95%, 96%, 97%, 98%, or 99%) identical to the nucleic acid sequence identified by SEQ ID NO:1, and (b) a hPIV3 RNA polynucleotide encoded by a nucleic acid comprising the nucleic acid sequence identified by SEQ ID NO:2 or a nucleic acid sequence that is at least 90% (e.g., 90%, 91%, 92%, 93%, 94%, 95%, 96%, 97%, 98%, or 99%) identical to the nucleic acid sequence identified by SEQ ID NO:2.

hMPV/hPIV3 Fusion (F) Proteins and Other Antigens/Antigenic Polypeptides

Human Metapneumovirus (hMPV) F Protein. hMPV shares substantial homology with respiratory syncytial virus (RSV) in its surface glycoproteins. hMPV fusion protein (F) is related to other paramyxovirus fusion proteins and appears to have homologous regions that may have similar functions. The hMPV F protein amino acid sequence contains features characteristic of other paramyxovirus F proteins, including a putative cleavage site and potential N-linked glycosylation sites. Paramyxovirus F proteins are synthesized as inactive precursors (FO) that are cleaved by host cell proteases into the biologically fusion-active F1 and F2 domains (see, e.g., Cseke G. et al. *Journal of Virology* 2007; 81(2):698-707, incorporated herein by reference). hMPV has one putative cleavage site, in contrast to the two sites established for RSV F, and only shares 34% amino acid sequence identity with RSV F. F2 is extracellular and disulfide linked to F1. F proteins are type I glycoproteins existing as trimers, with two 4-3 heptad repeat domains at the N- and C-terminal regions of the protein (HR1 and HR2), which form coiled-coil alpha-helices. These coiled coils become apposed in an antiparallel fashion when the protein undergoes a conformational change into the fusogenic state. There is a hydrophobic fusion peptide N proximal to the N-terminal heptad repeat, which is thought to insert into the target cell membrane, while the association of the heptad repeats brings the transmembrane domain into close proximity, inducing membrane fusion (see, e.g., Baker, K A et al. *Mol. Cell* 1999; 3:309-319). This mechanism has been proposed for a number of different viruses, including RSV, influenza virus, and human immunodeficiency virus. F proteins are major antigenic determinants for all known paramyxoviruses and for other viruses that possess similar fusion proteins such as human immunodeficiency virus, influenza virus, and Ebola virus.

Human Parainfluenza Virus Type 3 (hPIV3) F Protein. Parainfluenza viruses belong to the family Paramyxoviridae. These are enveloped viruses with a negative-sense single-stranded RNA genome. Parainfluenza viruses belong to the subfamily Paramyxoviridae, which is subdivided into three genera: Respirovirus (PIV-1, PIV-3, and Sendai virus (SeV)), Rubulavirus (PIV-2, PIV-4 and mumps virus) and Morbillivirus (measles virus, rinderpest virus and canine distemper virus (CDV)). Their genome, a ~15,500 nucleotide-long negative-sense RNA molecule, encodes two envelope glycoproteins, the hemagglutinin-neuraminidase (HN), the fusion protein (F or F0), which is cleaved into F1 and F2 subunits, a matrix protein (M), a nucleocapsid protein (N) and several nonstructural proteins including the viral replicase (L). All parainfluenza viruses, except for PIV1, express a non-structural V protein that blocks IFN signaling in the infected cell and acts therefore as a virulence factor (see, e.g., Nishio M et al. *J Virol.* 2008; 82(13):6130-38).

PIV3 fusion protein (PIV3 F) is located on the viral envelope, where it facilitates the viral fusion and cell entry. The F protein is initially inactive, but proteolytic cleavage leads to its active forms, F1 and F2, which are linked by disulfide bonds. This occurs when the HN protein binds its receptor on the host cell's surface. During early phases of infection, the F glycoprotein mediates penetration of the host cell by fusion of the viral envelope to the plasma membrane. In later stages of the infection, the F protein facilitates the fusion of the infected cells with neighboring uninfected cells, which leads to the formation of a syncytium and spread of the infection.

An antigenic polypeptide (e.g., hMPV/hPIV3 F protein) encoded by a RNA vaccine of the present disclosure may be naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain polypeptides or multichain polypeptides, such as antibodies or insulin, and may be associated or linked to each other. Most commonly, disulfide linkages are found in multichain polypeptides. The term "polypeptide" may also apply to amino acid polymers in which at least one amino acid residue is an artificial chemical analogue of a corresponding naturally-occurring amino acid.

A "polypeptide variant" is a molecule that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. Ordinarily, variants possess at least 50% identity to a native sequence or a reference sequence. In some embodiments, variants share at least 80% identity or at least 90% identity with a native sequence or a reference sequence.

Vaccines of the present disclosure may include a variant of a hMPV and/or hPIV3 F protein. These include, for example, substitutional, insertional, deletion and covalent variants and derivatives. The term "derivative" is synonymous with the term "variant" and generally refers to a molecule that has been modified and/or changed in any way relative to a reference molecule or a starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini and any combination(s) thereof.

When referring to polypeptides the term "domain" refers to a motif of a polypeptide having one or more identifiable structural or functional characteristics or properties (e.g., binding capacity, serving as a site for protein-protein interactions).

When referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide-based or polynucleotide-based molecules.

The terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Polypeptide or polynucleotide molecules of the present disclosure may share a certain degree of sequence identity with the reference molecules (e.g., reference polypeptides or reference polynucleotides), for example, an F protein having an amino acid sequence identified by SEQ ID NO:7 or SEQ ID NO:8. The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM *J Applied Math.*, 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

Thus, the term "identity" refers to a relationship between the sequences of two or more polypeptides or polynucleotides, as determined by comparing the sequences. In the art, identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.*

25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm.

The term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

Nucleic Acids/Polynucleotides

The term "nucleic acid" includes any compound and/or substance that comprises a polymer of nucleotides (nucleotide monomer). These polymers are referred to as polynucleotides. Thus, the terms "nucleic acid" and "polynucleotide" are used interchangeably.

Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally-occurring or wild-type sequence (e.g., a naturally-occurring or wild-type mRNA sequence encoding a polypeptide or protein of interest (e.g., F protein)).

In some embodiments, a codon-optimized sequence shares between 65% and 85% (e.g., between about 67% and about 85%, or between about 67% and about 80%) sequence identity to a naturally-occurring sequence or a wild-type sequence (e.g., a naturally-occurring or wild-type mRNA sequence encoding a polypeptide or protein of interest (e.g., an antigenic protein or polypeptide)). In some embodiments, a codon-optimized sequence shares between 65% and 75%, or about 80% sequence identity to a naturally-occurring sequence or wild-type sequence (e.g., a naturally-occurring or wild-type mRNA sequence encoding a polypeptide or protein of interest (e.g., an antigenic protein or polypeptide)).

In some embodiments a codon-optimized RNA (e.g., mRNA) may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Variants

In some embodiments, an RNA of the present disclosure encodes a hMPV/hPIV3 antigen variant. Antigen or other polypeptide variants refers to molecules that differ in their amino acid sequence from a wild-type, native or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a hMPV/hPIV3 vaccine comprises an mRNA ORF having a nucleotide sequence identified by any one of the sequences provided herein (see e.g., Sequence Listing), or having a nucleotide sequence at least 80%, at least 85%, at least 90%, at least 95%, at least 96%, at least 97%, at least 98%, or at least 99% identical to a nucleotide sequence identified by any one of the sequence provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, in particular the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

As recognized by those skilled in the art, protein fragments, functional protein domains, and homologous proteins are also considered to be within the scope of hMPV/hPIV3 antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to hMPV/hPIV3. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA (e.g., mRNA) vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, a hMPV/hPIV3 RNA (e.g., mRNA) vaccine of the present disclosure comprises a natural 5' cap. In some embodiments, a 5' cap may be a 5' cap analog, such as a 5' diguanosine cap, tetraphosphate cap analogs having a methylene-bis (phosphonate) moiety, cap analogs having a sulfur substitution for a non-bridging oxygen, N7-benzylated dinucleoside tetraphosphate analogs, or anti-reverse cap analogs. In some embodiments, the 5' cap is a 7mG(5')ppp(5')NlmpNp cap. In some embodiments, the 5' cap is a 7mG(5')ppp(5')NlmpN2mp cap. In some embodiments, the 5'cap analog is a 5' diguanosine cap.

In some embodiments, a hMPV/hPIV3 RNA (e.g., mRNA) vaccine includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. luciferase, green fluorescent protein (GFP), enhanced GFP (EGFP), or (3-Galactosidase), or a marker or selection protein (e.g. alpha-globin, galactokinase and xanthine: guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, a hMPV/hPIV3 RNA (e.g., mRNA) vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, a hMPV/hPIV3 RNA (e.g., mRNA) vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, including (e.g., consisting of) a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments a hMPV/hPIV3 RNA (e.g., mRNA) vaccine may have one or more AU-rich sequences removed. These sequences, sometimes referred to as AURES are destabilizing sequences found in the 3'UTR. The AURES may be removed from the RNA (e.g., mRNA) vaccines. Alternatively the AURES may remain in the RNA (e.g., mRNA) vaccine.

Signal Peptides In some embodiments, a hMPV/hPIV3 vaccine comprises a RNA having an ORF that encodes a signal peptide fused to the hMPV/hPIV3 antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other tha hMPV/hPIV3 antigens in nature) are known in the art and can be tested for desired properties and then incorporated into a nucleic acid of the disclosure. In some embodiments, the signal peptide is a bovine prolactin signal peptide. For example, the bovine prolactin signal peptide may comprise sequence MDSKGSSQKGSRLLLLLVVSNLLLPQGVVG (SEQ ID NO: 17). Other signal peptide sequences may also be used. For example, the signal peptide may comprise one of the following sequences: MDWTWILFLVAAATRVHS (SEQ ID NO: 18); METPAQLLFLLLLWLPDTTG (SEQ ID NO: 19); MLGSNSGQRVVFTILLLLVAPAYS (SEQ ID NO: 20); MKCLLYLAFLFIGVNCA (SEQ ID NO: 21); MWLVSLAIVTACAGA (SEQ ID NO: 22).

Fusion Proteins

In some embodiments, a hMPV/hPIV3 RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the hMPV/hPIV3 antigen. Antigenic fusion proteins, in some embodiments, retain the functional property from each original protein.

Scaffold Moieties

The RNA (e.g., mRNA) vaccines as provided herein, in some embodiments, encode fusion proteins which comprise hMPV/hPIV3 antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta, J. et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments a hMPV/hPIV3 antigen is fused to HBsAG or HBcAG to facilitate self-assembly of nanoparticles displaying the hMPV/hPIV3 antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol.* 2009; 390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem.* 2003; 8:105-111; Lawson D. M. et al. *Nature.* 1991; 349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. *Flavins and Flavoproteins.* Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. *J Mol Biol.* 2006; 362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. *Nat Struct Mol Biol.* 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J.* 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a hMPV/hPIV3 antigen). In some embodiments, a codon optimized sequence shares less than 90% sequence identity to a naturally-occurring or wild-type sequence (e.g., a naturally-occurring or wild-type mRNA sequence encoding a hMPV/hPIV3 antigen). In some embodiments, a codon optimized sequence shares less than 85% sequence identity to a naturally-occurring or wild-type sequence (e.g., a naturally-occurring or wild-type mRNA sequence encoding a hMPV/hPIV3 antigen). In some embodiments, a codon optimized sequence shares less than 80% sequence identity to a naturally-occurring or wild-type sequence (e.g., a naturally-occurring or wild-type mRNA sequence encoding a hMPV/hPIV3 antigen). In some embodiments, a codon optimized sequence shares less than 75% sequence identity to a naturally-occurring or wild-type sequence (e.g., a naturally-occurring or wild-type mRNA sequence encoding a hMPV/hPIV3 antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a hMPV/hPIV3 antigen). In some embodiments, a codon optimized sequence shares between 65% and 75% or about 80% sequence identity to a naturally-occurring or wild-type sequence (e.g., a naturally-occurring or wild-type mRNA sequence encoding a hMPV/hPIV3 antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a hMPV/hPIV3 antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of a hMPV/hPIV3 vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications hMPV/hPIV3 RNA vaccines of the present disclosure comprise, in some embodiments, at least one nucleic acid (e.g., RNA) having an open reading frame encoding at least one hMPV/hPIV3 antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/U52014/058891; PCT/U52014/070413; PCT/US2015/36773; PCT/US2015/36759; PCT/US2015/36771; or PCT/I132017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

N-Linked Glycosylation Site Mutants

N-linked glycans of viral proteins play important roles in modulating the immune response. Glycans can be important for maintaining the appropriate antigenic conformations, shielding potential neutralization epitopes, and may alter the proteolytic susceptibility of proteins. Some viruses have putative N-linked glycosylation sites. Deletion or modification of an N-linked glycosylation site may enhance the immune response. Thus, the present disclosure provides, in some embodiments, hMPV/hPIV3 RNA (e.g., mRNA) vaccines comprising nucleic acids (e.g., mRNA) encoding antigenic polypeptides (e.g., hMPV/hPIV3 F proteins) that comprise a deletion or modification at one or more N-linked glycosylation sites.

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 23), where R is a purine (adenine or guanine) three bases upstream of the start codon (AUG), which is followed by another 'G'. 5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived a-globin or b-globin (8278063; 9012219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 24) (WO2014/144196) may also be used. In another embodiment, 5' UTR of a TOP gene is a 5' UTR of a TOP gene lacking the 5' TOP motif (the oligopyrimidine tract) (e.g., WO2015/101414, WO2015/101415, WO2015/062738, WO2015/024667, WO2015/024667; 5' UTR element derived from ribosomal protein Large 32 (L32) gene (WO2015/101414, WO2015/101415, WO2015/062738), 5' UTR element derived from the 5'UTR of an hydroxysteroid (17-β) dehydrogenase 4 gene (HSD17B4) (WO2015/024667), or a 5' UTR element derived from the 5' UTR of ATP5A1 (OW2015/024667) can be used. In some embodiments, an internal ribosome entry site (IRES) is used instead of a 5' UTR.

In some embodiments, a 5' UTR of the present disclosure comprises the sequence of SEQ ID NO: 12.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 25) nonamers. Molecules containing this type of AREs include GM-CSF and TNF-a. Class III ARES are less well defined. These U rich regions do not contain an AUUUA motif c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Figure 4A:
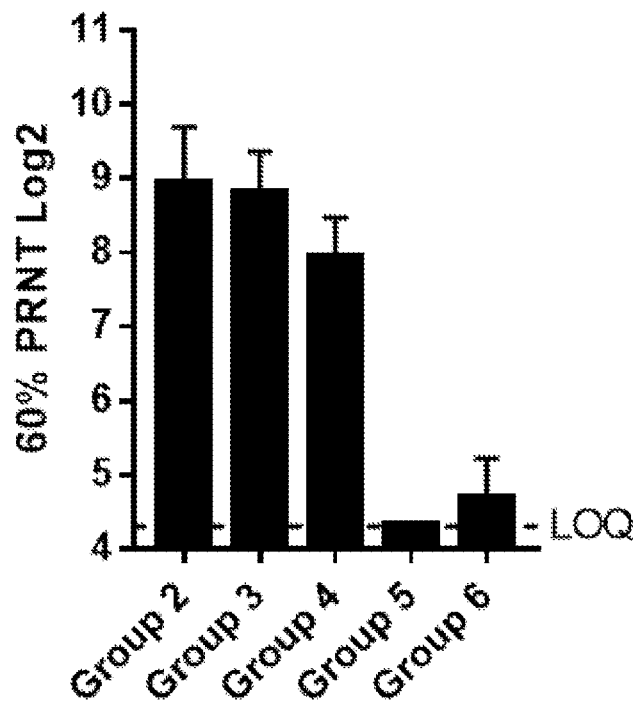
FIGS. 4A-4B are graphs showing hMPV (FIG. 4A) and PIV3 (FIG. 4B) serum neutralizing antibody titers in cotton rats. PIV3 neutralizing antibody titers detected at high levels in all animals immunized with PIV3-F and/or PIV3-HN mRNA (Groups 9-13).
Figure 4B:
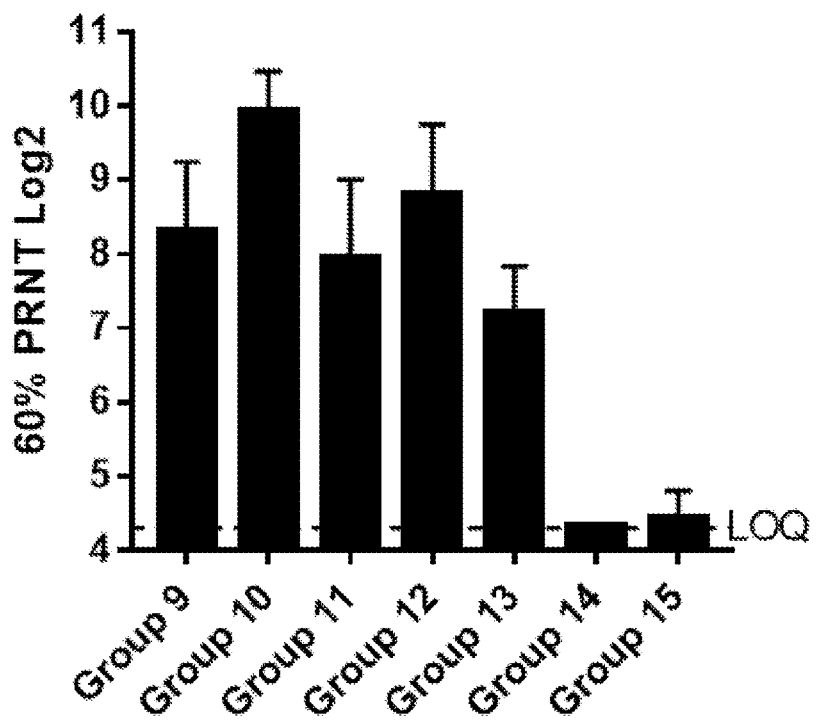

3' UTRs may be heterologous or synthetic. With respect to 3' UTRs, globin UTRs, including *Xenopus* β-globin UTRs and human β-globin UTRs are known in the art (8278063, 9012219, US20110086907). A modified β-globin construct with enhanced stability in some cell types by cloning two sequential human β-globin 3'UTRs head to tail has been developed and is well known in the art (US2012/0195936, WO2014/071963). In addition a2-globin, a1-globin, UTRs and mutants thereof are also known in the art (WO2015/101415, WO2015/024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014/152774), rabbit β globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and mouse ribosomal protein are used. Other examples include rps9 3'UTR (WO2015/101414, FIG. 4 (WO2015/101415), and human albumin 7 (WO2015/101415).

In some embodiments, a 3' UTR of the present disclosure comprises the sequence of SEQ ID NO: 13.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 2010/0129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US patent publication 2009/0226470, herein incorporated by reference in its entirety, and those known in the art.

In Vitro Transcription of RNA (e.g., mRNA)

A hMPV/hPIV3 RNA (e.g., mRNA) vaccine of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

In some embodiments, the in vitro transcription template used to produce the RNA (e.g., mRNA) polynucleotides of the present disclosure comprises the nucleotide sequence identified by any one of SEQ ID NO:1-3.

A "5' untranslated region" (5'UTR) refers to a region of an mRNA that is directly upstream (i.e., 5') from the start codon (i.e., the first codon of an mRNA transcript translated by a ribosome) that does not encode a polypeptide.

A "3' untranslated region" (3'UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, Mass.), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Pharmaceutical Formulations

Provided herein are compositions (e.g., pharmaceutical compositions), methods, kits and reagents for prevention or treatment of hMPV/hPIV3 in humans and other mammals, for example. hMPV/hPIV3 RNA (e.g., mRNA) vaccines can be used as therapeutic or prophylactic agents. They may be used in medicine to prevent and/or treat infectious disease.

In some embodiments, a hMPV/hPIV3 vaccine containing RNA polynucleotides as described herein can be administered to a subject (e.g., a mammalian subject, such as a human subject), and the RNA polynucleotides are translated in vivo to produce an antigenic polypeptide (antigen).

An "effective amount" of a hMPV/hPIV3 vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a hMPV/hPIV3 vaccine provides an induced or boosted immune response as a function of antigen production in the cells of the subject. In some embodiments, an effective amount of the hMPV/hPIV3 RNA vaccine containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

In some embodiments, a vaccine of the present disclosure is demonstrated to be effective by showing a desired result in an animal model, e.g., a rodent or non-human primate model. For example, vaccination of cotton rats with a hMPV/hPIV3 combination vaccine as provided herein resulted in the induction of high levels of neutralizing antibodies and reduced the viral titers in the nose and lungs of the immunized cotton rats after challenge with hMPV or hPIV3 viruses, without evidence of vaccine-enhanced respiratory disease (ERD). Studies of vaccinated African Green Monkeys demonstrated similar results. The hMPV/PIV3 combination vaccine afforded full protection against both viruses in the lung and the nose of the vaccinated animals after less than three intramuscular doses of the vaccine.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of hMPV/hPIV3. hMPV/hPIV3 RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

hMPV/hPIV3 RNA (e.g., mRNA) vaccines may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, hMPV/hPIV3 RNA vaccines may be administered intramuscularly, intranasally or intradermally, similarly to the administration of inactivated vaccines known in the art.

The hMPV/hPIV3 RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including hMPV/hPIV3 RNA vaccines and RNA vaccine compositions and/or complexes optionally in combination with one or more pharmaceutically acceptable excipients.

hMPV/hPIV3 RNA (e.g., mRNA) vaccines may be formulated or administered alone or in conjunction with one or more other components. For instance, hMPV/hPIV3 RNA vaccines (vaccine compositions) may comprise other components including, but not limited to, adjuvants.

In some embodiments, hMPV/hPIV3 RNA vaccines do not include an adjuvant (they are adjuvant free).

hMPV/hPIV3 RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, hMPV/hPIV3 RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, hMPV/hPIV3 RNA vaccines are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with hMPV/hPIV3 RNA vaccines (e.g., for transplantation into a subject), hyaluronidase, nanoparticle mimics and combinations thereof.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. typhimurium, H. pylori, V. cholera, S. marcesens, S. flexneri, T. pallidum, L. pneumophila, B. burgdorferei, C. difficile, R. meliloti, A. tumefaciens, R. lupini, B. clarridgeiae, P. mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8). In some embodiments, the flagellin protein comprises the following amino acid sequence: MAQVINTNSLSLLTQNNLNKSQSALGTAIERLSSGL-RINSAKDDAAGQAIA NRFTANIKGLTQASRNANDGI-SIAQTTEGALNEINNNLQRVRELAVQSANGTNSQSD LDSIQAEITQRLNEIDRVSGQTQFNGVKVLAQDNTL-TIQVGANDGETIDIDLKEISSKT LGLDKLNVQDAY-TPKETAVTVDKTTYKNGTDPITAQSNTDIQTAIGG-GATGVTGADI KFKDGQYYLDVKGGASAGVYKATY-DETTKKVNIDTTDKTPLATAEATAIRGTATIT HNQI-AEVTKEGVDTTTVAAQLAAAGVTGADKDNT-SLVKLSFEDKNGKVIDGGYAV KMGDDFYAATYDEKTGAITAKTTTYTDGTGVAQT-GAVKFGGANGKSEVVTATDGK TYLASDLDKHN-FRTGGELKEVNTDKTENPLQKIDAALAQVDTLRSDL-GAVQNRFNS AITNLGNTVNNLSSARSRIED-SDYATEVSNMSRAQILQQAGTSVLAQANQVPQNVLS LLR (SEQ ID NO:10). In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO:11).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides (e.g., F proteins) and the other encoding the flagellin polypeptide. The at least two RNA polynucleotides may be co-formulated in a carrier such as a lipid nanoparticle. Alternatively, the at least two RNA polynucleotides may be separately formulated.

Lipid Nanoparticles (LNPs) In some embodiments, hMPV/hPIV3 RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016/000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

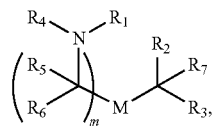

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH2)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O) N(R)$_2$, —N(OR)C(S)N (R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$,  —C(O)OR,  —OC(O)R,  —CX$_3$, —CX$_2$H, —CXH$_2$, —CN, —C(O)N(R)$_2$, —N(R)C(O)R, —N(R)S(O)$_2$R,  —N(R)C(O)N(R)$_2$,  —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR,  —N(OR)C(O)R,  —N(OR)S(O)$_2$R, —N(OR)C(O)OR, —N(OR)C(O)N(R)$_2$, —N(OR)C(S)N(R)$_2$,  —N(OR)C(=NR$_9$)N(R)$_2$,  —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) R$_4$ is —(CH$_2$)$_n$Q in which n is 1 or 2, or (ii) R$_4$ is —(CH$_2$)$_n$CHQR in which n is 1, or (iii) R$_4$ is —CHQR, and —CQ(R)$_2$, then Q is either a 5- to 14-membered heteroaryl or 8- to 14-membered heterocycloalkyl;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{2-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R';

R$_2$ and R$_3$ are independently selected from the group consisting of H, C$_{1-14}$ alkyl, C$_{2-14}$ alkenyl, —R*YR", —YR", and —R*OR", or R$_2$ and R$_3$, together with the atom to which they are attached, form a heterocycle or carbocycle;

R$_4$ is selected from the group consisting of a C$_{3-6}$ carbocycle, —(CH$_2$)$_n$Q, —(CH$_2$)$_n$Q, —(CH$_2$)$_n$CHQR, —CHQR, —CQ(R)$_2$, and unsubstituted C$_{1-6}$ alkyl, where Q is selected from a C$_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R,  —N(R)C(O)N(R)$_2$,  —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR,  —N(OR)C(O)R,  —N(OR)S(O)$_2$R, —N(OR)C(O)OR, —N(OR)C(O)N(R)$_2$, —N(OR)C(S)N(R)$_2$,  —N(OR)C(=NR$_9$)N(R)$_2$,  —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each R$_5$ is independently selected from the group consisting of C$_{1-3}$ alkyl, C$_{2-3}$ alkenyl, and H;

each R$_6$ is independently selected from the group consisting of C$_{1-3}$ alkyl, C$_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

R$_7$ is selected from the group consisting of C$_{1-3}$ alkyl, C$_{2-3}$ alkenyl, and H;

R$_8$ is selected from the group consisting of C$_{3-6}$ carbocycle and heterocycle;

R$_9$ is selected from the group consisting of H, CN, NO$_2$, C$_{1-6}$ alkyl, —OR, —S(O)$_2$R, —S(O)$_2$N(R)$_2$, C$_{2-6}$ alkenyl, C$_{3-6}$ carbocycle and heterocycle;

each R is independently selected from the group consisting of C$_{1-3}$ alkyl, C$_{2-3}$ alkenyl, and H;

each R' is independently selected from the group consisting of C$_{1-18}$ alkyl, C$_{2-18}$ alkenyl, —R*YR", —YR", and H;

each R" is independently selected from the group consisting of C$_{3-14}$ alkyl and C$_{3-14}$ alkenyl;

each R* is independently selected from the group consisting of C$_{1-12}$ alkyl and C$_{1-12}$ alkenyl;

each Y is independently a C$_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which R$_1$ is selected from the group consisting of C$_{5-30}$ alkyl, C$_{5-20}$ alkenyl, —R*YR", —YR", and —R"M'R'; R$_2$ and R$_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

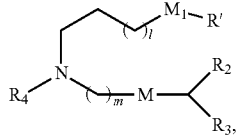

(IA)

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

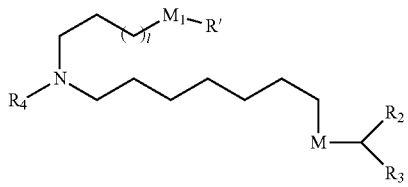

(II)

or a salt or isomer thereof, wherein 1 is selected from 1, 2, 3, 4, and 5; $M_1$ is a bond or M'; $R_4$ is unsubstituted $C_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

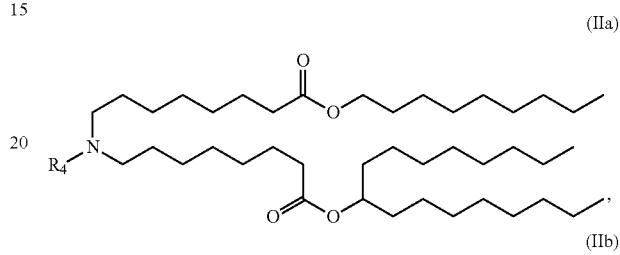

(IIa)

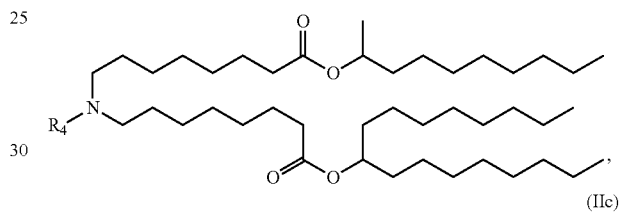

(IIb)

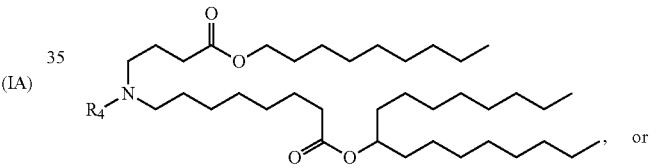

(IIc)

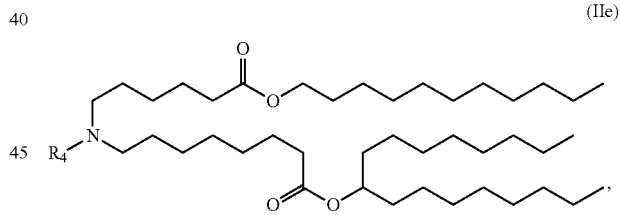

(IIe)

or a salt or isomer thereof, wherein $R_4$ is as described herein.

In some embodiments, a subset of compounds of Formula (I) includes those of Formula (IId):

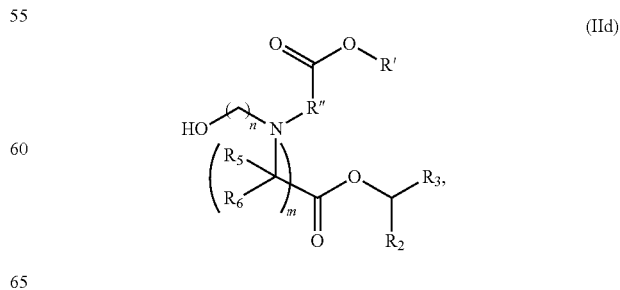

(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

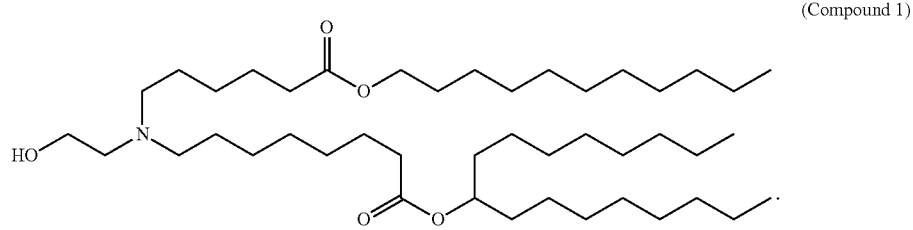 [SMILES: CCCCCCCCCCCOC(=O)CCCCCN(CCO)CCCCCCCC(=O)OC(CCCCCCCC)CCCCCCCC]

(Compound 1)

In some embodiments, an ionizable cationic lipid of the disclosure comprises a compound having structure:

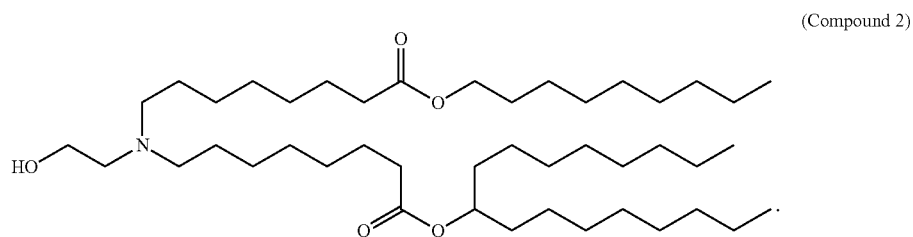 [SMILES: CCCCCCCCCOC(=O)CCCCCCCN(CCO)CCCCCCCC(=O)OC(CCCCCCCC)CCCCCCCC]

(Compound 2)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine,1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises a mixture of 4 lipids, including Compound 1; 1,2-dimyristoyl-sn-glycerol, methoxypolyethyleneglycol (PEG2000-DMG); 1,2-distearoyl-sn-glycero-3-phosphocholine (DSPC); and cholesterol. In some embodiments, a vaccine comprises a mRNA encoding a hMPV F protein of strain A/TN92-4 (e.g., SEQ ID NO:4) and a mRNA encoding a PIV3 F protein of strain PER/FLA4815/2008 (e.g., SEQ ID NO:5) formulated in a LNP that comprises a mixture of 4 lipids, including Compound 1; 1,2-dimyristoyl-sn-glycerol, methoxypolyethyleneglycol (PEG2000-DMG); DSPC; and cholesterol.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Multivalent Vaccines

The hMPV/hPIV3 vaccines, as provided herein, may include an RNA (e.g. mRNA) or multiple RNAs encoding two or more antigens of the same or different hMPV/hPIV3 species. In some embodiments, a hMPV/hPIV3 vaccine includes an RNA or multiple RNAs encoding two or more antigens selected from hMPV F protein and hPIVs F protein. In some embodiments, the RNA (at least one RNA) of a hMPV/hPIV3 vaccine may encode 1, 2, 3, 4, 5, 6, 7, 8, 9, 10, 11, 12, or more antigens.

In some embodiments, two or more different RNA (e.g., mRNA) encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The hMPV/hPIV3 vaccines, as provided herein, may include an RNA or multiple RNAs encoding two or more antigens of the same or different hMPV/hPIV3 strains. Also provided herein are combination vaccines that include RNA encoding one or more hMPV/hPIV3 antigen(s) and one or more antigen(s) of a different organisms (e.g., bacterial and/or viral organism). For example, in some embodiments, an hMPV/PIV3 vaccine of the present disclosure comprises an hMPV fusion (F) protein and a PIV3 F protein. In some embodiments, the two F proteins are co-formulated at a 1:1 mass ratio in an LNP. In some embodiments, the two F proteins are formulated separately in separate LNPs. Thus, the vaccines of the present disclosure may be combination vaccines that target one or more antigens of the same strain/species, or one or more antigens of different strains/ species, e.g., antigens which induce immunity to organisms which are found in the same geographic areas where the risk of hMPV/hPIV3 infection is high or organisms to which an individual is likely to be exposed to when exposed to hMPV/hPIV3. In some embodiments, the hMPV F protein is of the A/TN92-4 hMPV strain and the hPIV3 F protein is of the PER/FLA4815/2008 strain.

Dosing/Administration

Provided herein are compositions (e.g., pharmaceutical compositions), methods, kits and reagents for prevention and/or treatment of hMPV/hPIV3 in humans and other mammals. hMPV/hPIV3 RNA vaccines can be used as therapeutic or prophylactic agents. In some aspects, the RNA vaccines of the disclosure are used to provide prophylactic protection from hMPV/hPIV3. In some aspects, the RNA vaccines of the disclosure are used to treat a hMPV/ hPIV3 infection. In some embodiments, the hMPV/hPIV3 vaccines of the present disclosure are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the hMPV/hPIV3 vaccines are administered to a subject (e.g., a mammalian subject, such as a human subject) in an effective amount to induce an antigen-specific immune response. The RNA encoding the hMPV/hPIV3 antigen is expressed and translated in vivo to produce the antigen, which then stimulates an immune response in the subject.

In some embodiments, an hMPV/hPIV3 vaccine of the disclosure results in high neutralizing antibody titers (e.g., as measured by the 60% reduction end point assay) after fewer than three doses (e.g., after one or two doses). In some embodiments, a cotton rat model can be used to test the vaccine and a titer of at least 9 (log 2 transformed titer using 60% PRNT assay) can be measured using this assay. In some embodiments, a vaccine of the disclosure results in a higher titer than that observed with a traditional formalin inactivated protein vaccine (e.g., FI-PIV3 or FI-HMPV). In another embodiment, an hMPV/hPIV3 vaccine of the disclosure protects against challenge infection, e.g., as measured by reduced viral load in both the nose and lung after fewer than three doses. In some embodiments, a cotton rat model can be used to test this end point. Surprisingly, an hMPV/hPIV3 vaccine of the disclosure results in neutralizing antibody titers and reduced viral load, but does not result in alveolitis or interstitial pneumonia. In some embodiments, a cotton rat model can be used to determine lung pathology. In another embodiment, the protection provided by an hMPV/hPIV3 vaccine of the disclosure protects against challenge with HPIV3 even though PIV3-HN mRNA is not present in the vaccine.

Prophylactic protection from hMPV/hPIV3 can be achieved following administration of a hMPV/hPIV3 RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against hMPV/hPIV3 is provided in aspects of the present disclosure. The method involves administering to the subject a hMPV/hPIV3 RNA vaccine comprising at least one RNA (e.g., mRNA) having an open reading frame encoding at least one hMPV/hPIV3 antigen, thereby inducing in the subject an immune response specific to hMPV/hPIV3 antigen, wherein anti-antigen antibody titer in the subject is increased following vaccination relative to anti-antigen antibody titer in a subject vaccinated with a prophylactically effective dose of a traditional vaccine against the hMPV/ hPIV3. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the hMPV/hPIV3 or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the hMPV/hPIV3 or an unvaccinated subject.

A method of eliciting an immune response in a subject against a hMPV/hPIV3 is provided in other aspects of the disclosure. The method involves administering to the subject a hMPV/hPIV3 RNA vaccine comprising at least one RNA polynucleotide having an open reading frame encoding at least one hMPV/hPIV3 antigen, thereby inducing in the subject an immune response specific to hMPV/hPIV3 antigen, wherein the immune response in the subject is higher than or equivalent to an immune response in a subject vaccinated with a traditional vaccine against the hMPV/hPIV3. In some embodiments, the response is higher for the mRNA vaccine of the disclosure even when the protein vaccine is administered at 2 times to 100 times the dosage level relative to the RNA vaccine.

In some embodiments, the immune response in the subject is equivalent to an immune response in a subject vaccinated with a traditional vaccine at twice the dosage level relative to the hMPV/hPIV3 RNA vaccine. In some embodiments, the immune response in the subject is equivalent to an immune response in a subject vaccinated with a traditional vaccine at three times the dosage level relative to the hMPV/hPIV3 RNA vaccine. In some embodiments, the immune response in the subject is equivalent to an immune response in a subject vaccinated with a traditional vaccine at 4 times, 5 times, 10 times, 50 times, or 100 times the dosage level relative to the hMPV/hPIV3 RNA vaccine. In some embodiments, the immune response in the subject is equivalent to an immune response in a subject vaccinated with a traditional vaccine at 10 times to 1000 times the dosage level relative to the hMPV/hPIV3 RNA vaccine. In some embodiments, the immune response in the subject is equivalent to an immune response in a subject vaccinated with a traditional vaccine at 100 times to 1000 times the dosage level relative to the hMPV/hPIV3 RNA vaccine.

In other embodiments, the immune response is assessed by determining [protein] antibody titer in the subject. In other embodiments, the ability of serum or antibody from an immunized subject is tested for its ability to neutralize viral uptake or reduce hMPV/hPIV3 transformation of human B lymphocytes. In other embodiments, the ability to promote a robust T cell response(s) is measured using art recognized techniques.

Other aspects the disclosure provide methods of eliciting an immune response in a subject against a hMPV/hPIV3 by administering to the subject a hMPV/hPIV3 RNA vaccine comprising at least one RNA polynucleotide having an open reading frame encoding at least one hMPV/hPIV3 antigen, thereby inducing in the subject an immune response specific to hMPV/hPIV3 antigen, wherein the immune response in the subject is induced 2 days to 10 weeks earlier relative to an immune response induced in a subject vaccinated with a prophylactically effective dose of a traditional vaccine against the hMPV/hPIV3. In some embodiments, the immune response in the subject is induced in a subject vaccinated with a prophylactically effective dose of a traditional vaccine at 2 times to 100 times the dosage level relative to the RNA vaccine.

In some embodiments, the immune response in the subject is induced within 14 days of vaccine administration. In some embodiments, the immune response in the subject increases (e.g., by at least 50%) over the course of 14 to 27 days, 14 to 56 days, or 27 to 56 days following vaccination.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against a hMPV/hPIV3 by administering to the subject a hMPV/hPIV3 RNA vaccine having an open reading frame encoding a first antigen, wherein the RNA polynucleotide does not include a stabilization element, and wherein an adjuvant is not co-formulated or co-administered with the vaccine.

hMPV/hPIV3 RNA (e.g., mRNA) vaccines may be administered by any route which results in a therapeutically effective outcome. These include, but are not limited to, intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. hMPV/hPIV3 RNA (e.g., mRNA) vaccines compositions are typically formulated in dosage unit form for ease of administration and uniformity of dosage. It will be understood, however, that the total daily usage of hMPV/hPIV3 RNA (e.g., mRNA)vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of a hMPV/hPIV3 vaccine, as provided herein, may be as low as 20 µg, administered for example as a single dose or as two 10 µg doses. In some embodiments, the effective amount is a total dose of 20 µg-200 µg. For example, the effective amount may be a total dose of 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg. In some embodiments, the effective amount is a total dose of 25 µg-200 µg. In some embodiments, the effective amount is a total dose of 50 µg-200 µg.

In some embodiments, hMPV/hPIV3 RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, hMPV/hPIV3 RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, hMPV/hPIV3 RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, hMPV/hPIV3 RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a hMPV/hPIV3 RNA (e.g., mRNA) vaccine composition may be administered three or four times.

In some embodiments, hMPV/hPIV3 RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the hMPV/hPIV3 RNA (e.g., mRNA) vaccine for use in a method of vaccinating a subject is administered the subject a single dosage of between 10 µg/kg and 400 µg/kg of the nucleic acid vaccine in an effective amount to vaccinate the subject. In some embodiments, the RNA vaccine for use in a method of vaccinating a subject is administered the subject a single dosage of between 10 µg and 400 µg of the nucleic acid vaccine in an effective amount to vaccinate the subject. In some embodiments, a hMPV/hPIV3 RNA (e.g., mRNA) vaccine for use in a method of vaccinating a subject is administered to the subject as a single dosage of 25-1000 µg (e.g., a single dosage of mRNA encoding a hMPV/hPIV3 antigen). In some embodiments, a hMPV/hPIV3 RNA vaccine is administered to the subject as a single dosage of 25, 50, 100, 150, 200, 250, 300, 350, 400, 450, 500, 550, 600, 650, 700, 750, 800, 850, 900, 950 or 1000 µg. For example, a hMPV/hPIV3 RNA vaccine may be administered to a subject as a single dose of 25-100, 25-500, 50-100, 50-500, 50-1000, 100-500, 100-1000, 250-500, 250-1000, or 500-1000 µg. In some embodiments, a hMPV/hPIV3 RNA (e.g., mRNA) vaccine for use in a method of vaccinating a subject is administered to the subject as two dosages, the combination of which equals 25-1000 µg of the hMPV/hPIV3 RNA (e.g., mRNA) vaccine.

A hMPV/hPIV3 RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Methods of Treatment

Provided herein are compositions (e.g., pharmaceutical compositions), methods, kits and reagents for prevention and/or treatment of hMPV and/or hPIV3 infections. The RNA (e.g. mRNA) vaccines can be used as therapeutic or prophylactic agents, alone or in combination with other vaccine(s). They may be used in medicine to prevent and/or treat respiratory disease/infection (e.g., lower respiratory hMPV/hPIV3 infection). In some embodiments, the RNA (e.g., mRNA) vaccines of the present disclosure are used to provide prophylactic protection from hMPV and/or hPIV3. Prophylactic protection can be achieved following administration of a RNA (e.g., mRNA) vaccine of the present disclosure. RNA (e.g., mRNA) vaccines of the present disclosure may be used to treat or prevent viral "co-infections" containing two or more respiratory infections. Vaccines can be administered once, twice, three times, four times or more, but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against hMPV/hPIV3 is provided in aspects of the present disclosure. The method involves administering to the subject an effective amount of a RNA (e.g., mRNA) vaccine described herein, to thereby inducing in the subject an immune response specific to hMPV and/or hPIV3, wherein antibody titer of antibodies against hMPV and/or hPIV3 in the subject is increased following vaccination relative to antibody titer in a subject vaccinated with a prophylactically effective dose of a traditional vaccine against hMPV and/or hPIV3.

In some embodiments, a RNA (e.g., mRNA) vaccine (e.g., a hMPV/hPIV3 RNA vaccine) capable of eliciting an immune response is administered intramuscularly via a composition including a compound according to Formula (I), (IA), (II), (IIa), (IIb), (IIc), (IId) or (IIe) (e.g., Compound 3, 18, 20, 25, 26, 29, 30, 60, 108-112, or 122).

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the RNA (e.g., mRNA) vaccines of the present disclosure. For instance, a traditional vaccine includes but is not limited to live/attenuated microorganism vaccines, killed/inactivated microorganism vaccines, subunit vaccines, protein antigen vaccines, DNA vaccines, VLP vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-hMPV F protein and/or anti-hPIV F protein antibody titer in the subject is increased 1 log to 10 log following vaccination relative to anti-hMPV F protein and/or anti-hPIV F protein antibody titer in a subject vaccinated with a prophylactically effective dose of a traditional vaccine against hMPV and/or hPIV3.

In some embodiments the anti-hMPV F protein and/or anti-hPIV F protein antibody titer in the subject is increased 1 log, 2 log, 3 log, 5 log or 10 log following vaccination relative to anti-hMPV F protein and/or anti-hPIV F protein antibody titer in a subject vaccinated with a prophylactically effective dose of a traditional vaccine against hMPV and/or hPIV3.

A method of eliciting an immune response in a subject against hMPV and/or hPIV3 is provided in other aspects of the disclosure. The method involves administering to the subject an effective amount of a RNA (e.g., mRNA) vaccine described herein, to thereby inducing in the subject an immune response specific to hMPV and/or hPIV3, wherein the immune response in the subject is equivalent to an immune response in a subject vaccinated with a traditional vaccine against the hMPV and/or hPIV3 at 2 times to 100 times the dosage level relative to the RNA (e.g., mRNA) vaccine.

In some embodiments, the immune response in the subject is equivalent to an immune response in a subject vaccinated with a traditional vaccine at 2, 3, 4, 5, 10, 50, 100 times the dosage level relative to the hMPV and/or hPIV3RNA (e.g., mRNA) vaccine. In some embodiments the immune response in the subject is equivalent to an immune response in a subject vaccinated with a traditional vaccine at 10-100 times, or 100-1000 times, the dosage level relative to the hMPV and/or hPIV3RNA (e.g., mRNA) vaccine. In some embodiments the immune response is assessed by determining [protein] antibody titer in the subject.

In some embodiments, the immune response in the subject is induced 2 days earlier, or 3 days earlier, relative to an immune response induced in a subject vaccinated with a prophylactically effective dose of a traditional vaccine. In some embodiments the immune response in the subject is induced 1 week, 2 weeks, 3 weeks, 5 weeks, or 10 weeks earlier relative to an immune response induced in a subject vaccinated with a prophylactically effective dose of a traditional vaccine.

Therapeutic and Prophylactic Compositions

Provided herein are compositions (e.g., pharmaceutical compositions), methods, kits and reagents for prevention, treatment or diagnosis of hMPV and/or hPIV3 in humans and other mammals, for example. The RNA (e.g. mRNA) vaccines can be used as therapeutic or prophylactic agents. They may be used in medicine to prevent and/or treat infectious disease. In some embodiments, the respiratory RNA (e.g., mRNA) vaccines of the present disclosure are used fin the priming of immune effector cells, for example, to activate peripheral blood mononuclear cells (PBMCs) ex vivo, which are then infused (re-infused) into a subject.

In some embodiments, a RNA vaccine containing RNA (e.g., mRNA) polynucleotides as described herein can be administered to a subject (e.g., a mammalian subject, such as a human subject), and the RNA (e.g., mRNA) polynucleotides are translated in vivo to produce hMPV and/or hPIV3 F protein.

hMPV/hPIV3RNA (e.g., mRNA) vaccines may be induced for translation of a polypeptide (e.g., antigen or immunogen) in a cell, tissue or organism. In some embodiments, such translation occurs in vivo, although such translation may occur ex vivo, in culture or in vitro. In some embodiments, the cell, tissue or organism is contacted with an effective amount of a composition containing a RNA (e.g., mRNA) vaccine that contains a polynucleotide that has at least one a translatable region encoding an antigenic polypeptide (e.g., hMPV F protein and/or hPIV3 F protein).

An "effective amount" of an RNA (e.g. mRNA) vaccine is provided based, at least in part, on the target tissue, target cell type, means of administration, physical characteristics of the polynucleotide (e.g., size, and extent of modified nucleosides) and other components of the vaccine, and other determinants. In general, an effective amount of the RNA (e.g., mRNA) vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA, e.g., mRNA, vaccine), increased protein translation from the polynucleotide, decreased nucleic acid degradation (as demonstrated, for example, by increased duration of protein translation from a modified polynucleotide), or altered antigen specific immune response of the host cell. In some embodiments, RNA (e.g. mRNA) vaccines (including polynucleotides their encoded polypeptides) in accordance with the present disclosure may be used for treatment of hMPV and/or hPIV3.

RNA (e.g. mRNA) vaccines may be administered prophylactically or therapeutically as part of an active immunization scheme to healthy individuals or early in infection during the incubation phase or during active infection after onset of symptoms.

In some embodiments, a subject is an elderly human subject (e.g., an individual that is at least 65 years of age). For example, an elderly human subject may be 65, 66, 67, 68, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 years of age or older.

In some embodiments, a subject is a child (e.g., an individual that is 5 years of age or younger. For example, a subject that is a child may be 5, 4, 3, 2, 1 years of age or younger. In some embodiments, a subject that is a child may be 6-12 months of age. For example, a subject that is a child may be 6-7, 6-8, 6-9, 6-10, 6-11, 6-12, 7-8, 7-9, 7-10, 7-11, 7-12, 8-9, 8-10, 8-11, 8-12, 9-10, 9-11, 9-12, 10-11, 10-12, or 11-12 months of age. In some embodiments, a subject that is a child may be 6 months, 7 months, 8 months, 9 months, 10 months, 11 months, or 12 months of age.

In some embodiments, the RNA (e.g. mRNA) vaccines described herein are used for preventing a lower respiratory hMPV and/or hPIV3 infection in a subject having a pulmonary condition. A "pulmonary condition," as used herein, encompasses any condition that is associated with or results in impaired or reduce pulmonary function. In some embodiments, the pulmonary condition is associated with Chronic Obstructive Pulmonary Disease (COPD), asthma, congestive heart failure, diabetes, and any combination thereof. In some embodiments, the respiratory RNA (e.g. mRNA) vaccines described herein are used for preventing a lower respiratory hMPV and/or hPIV3 infection in a immunocompromised subject (e.g., an AIDS patient or a transplant recipient).

In some embodiments, the amount of RNA (e.g., mRNA) vaccine of the present disclosure provided to a cell, a tissue or a subject may be an amount effective for immune prophylaxis.

RNA (e.g. mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, hMPV/hPIV3 RNA (e.g. mRNA) vaccines may be administered intramuscularly or intradermally, similarly to the administration of inactivated vaccines known in the art.

RNA (e.g. mRNA) vaccines may be utilized in various settings depending on the prevalence of the infection or the degree or level of unmet medical need. As a non-limiting example, the RNA (e.g., mRNA) vaccines may be utilized to treat and/or prevent a variety of respiratory infections. RNA (e.g., mRNA) vaccines have superior properties in that they produce much larger antibody titers and produce responses early than commercially available anti-viral agents/compositions.

Provided herein are pharmaceutical compositions including RNA (e.g. mRNA) vaccines and RNA (e.g. mRNA) vaccine compositions and/or complexes optionally in combination with one or more pharmaceutically acceptable excipients.

RNA (e.g. mRNA) vaccines may be formulated or administered alone or in conjunction with one or more other components. For instance, hMPV/hPIV3 RNA (e.g., mRNA) vaccines (vaccine compositions) may comprise other components including, but not limited to, adjuvants.

In some embodiments, RNA (e.g. mRNA) vaccines do not include an adjuvant (they are adjuvant free).

RNA (e.g. mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, hMPV/hPIV3 RNA (e.g. mRNA) vaccines are administered to humans, human patients or subjects. For the purposes of the present disclosure, the phrase "active ingredient" generally refers to the RNA (e.g., mRNA) vaccines or the polynucleotides contained therein, for example, RNA polynucleotides (e.g., mRNA polynucleotides) encoding antigenic polypeptides (e.g., F proteins).

Formulations of the RNA vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

RNA (e.g. mRNA) vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with RNA (e.g. mRNA)vaccines (e.g., for transplantation into a subject), hyaluronidase, nanoparticle mimics and combinations thereof.

Modes of Vaccine Administration

The hMPV/hPIV3 RNA (e.g. mRNA) vaccines described herein may be administered by any route which results in a therapeutically effective outcome. These include, but are not limited, to intradermal, intramuscular, and/or subcutaneous administration. A RNA (e.g. mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

The present disclosure provides methods comprising administering RNA (e.g., mRNA) vaccines to a subject in need thereof. The exact amount required will vary from subject to subject, depending on the species, age, and general condition of the subject, the severity of the disease, the particular composition, its mode of administration, its mode of activity, and the like. RNA (e.g., mRNA) vaccines compositions are typically formulated in dosage unit form for ease of administration and uniformity of dosage. It will be understood, however, that the total daily usage of RNA (e.g., mRNA) vaccine compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, RNA (e.g. mRNA) vaccine compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see, e.g., the range of unit doses described in International Publication No WO2013078199, the contents of which are herein incorporated by reference in their entirety). The desired dosage may be delivered three times a day, two times a day, once a day, every other day, every third day, every week, every two weeks, every three weeks, every four weeks, every 2 months, every three months, every 6 months, etc. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a RNA (e.g., mRNA) vaccine composition may be administered three or four times.

In some embodiments, hMPV/hPIV3 RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the hMPV/hPIV3 RNA (e.g., mRNA) vaccine for use in a method of vaccinating a subject is administered to the subject as a single dosage of between 10 µg/kg and 400 µg/kg of the nucleic acid vaccine (in an effective amount to vaccinate the subject). In some embodiments the RNA (e.g., mRNA) vaccine for use in a method of vaccinating a subject is administered to the subject as a single dosage of between 10 µg and 400 µg of the nucleic acid vaccine (in an effective amount to vaccinate the subject).

In some embodiments, a hMPV/hPIV3 RNA (e.g., mRNA) vaccine for use in a method of vaccinating a subject is administered to the subject as a single dosage of 2-1000 µg (e.g., a single dosage of mRNA encoding hMPV, hPIV3, and/or RSV antigen). In some embodiments, a RNA (e.g., mRNA) vaccine for use in a method of vaccinating a subject is administered to the subject as a single dosage of 5-100 µg (e.g., a single dosage of mRNA encoding hMPV and/or hPIV3 F protein). In some embodiments, a RNA (e.g., mRNA) vaccine is administered to the subject as a single dosage of 2, 5, 10, 15, 20 25, 50, 100, 150, 200, 250, 300, 350, 400, 450, 500, 550, 600, 650, 700, 750, 800, 850, 900, 950 or 1000 µg. For example, a RNA (e.g., mRNA) vaccine may be administered to a subject as a single dose of 5-100, 10-100, 15-100, 20-100, 25-100, 25-500, 50-100, 50-500, 50-1000, 100-500, 100-1000, 250-500, 250-1000, or 500-1000 µg. In some embodiments, a RNA (e.g., mRNA) vaccine for use in a method of vaccinating a subject is administered to the subject as two dosages, the combination of which equals 10-1000 µg of the RNA (e.g., mRNA) vaccine.

hMPV/hPIV3 RNA (e.g., mRNA) Vaccine Formulations and Methods of Use

Some aspects of the present disclosure provide formulations of a hMPV/hPIV3 RNA (e.g., mRNA) vaccine, wherein the RNA (e.g., mRNA) vaccine is formulated in an effective amount to produce an antigen specific immune response in a subject (e.g., production of antibodies specific to an hMPV and/or hPIV3 F protein). "An effective amount" is a dose of an RNA (e.g., mRNA) vaccine effective to produce an antigen-specific immune response (e.g., that results in an ability to clear the virus more rapidly and/or a reduction in infectious virus in the nasal and/or lung passages upon exposure to the virus). Also provided herein are methods of inducing an antigen-specific immune response in a subject.

In some embodiments, the antigen-specific immune response is characterized by measuring an anti-hMPV and/or anti-PIV3 F protein antibody titer produced in a subject administered a RNA (e.g., mRNA) vaccine as provided herein. An antibody titer is a measurement of the amount of antibodies within a subject, for example, antibodies that are specific to a particular antigen (e.g., an anti-hMPV and/or anti-PIV3 F protein) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the RNA (e.g., mRNA) vaccine.

In some embodiments, an antibody induced by a RNA (e.g., mRNA) vaccine is a neutralizing antibody against the hMPV and/or hPIV3. A neutralizing titer is produced by neutralizing antibody against hMPV/PIV3 F protein as measured in serum of the subject. In some embodiments, an effective dose of the hMPV/PIV3 RNA (e.g., mRNA) vaccine is sufficient to produce more than a 500 neutralization titer. For example, an effective dose of the hMPV/PIV3 RNA (e.g., mRNA) vaccine is sufficient to produce a 1000-10,000 neutralization titer. In some embodiments, an effective dose of the hMPV/PIV3 RNA (e.g., mRNA) vaccine is sufficient to produce a 1000-2000, 1000-3000, 1000-4000, 1000-5000, 1000-6000, 1000-7000, 1000-8000, 1000-9000, 1000-10,000, 2000-3000, 2000-4000, 2000-5000, 2000-6000, 2000-7000, 2000-8000, 2000-9000, 2000-10,000, 3000-4000, 3000-5000, 3000-6000, 3000-7000, 3000-8000, 3000-9000, 3000-10,000, 4000-5000, 4000-6000, 4000-7000, 4000-8000, 4000-9000, 4000-10,000, 5000-6000, 5000-7000, 5000-8000, 5000-9000; 5000-10,000, 6000-7000, 6000-8000, 6000-9000, 6000-10,000, 7000-8000, 7000-9000, 7000-10,000, 8000-9000, 8000-10,000, or a 9000-10,000 neutralization titer. In some embodiments, an effective dose of the hMPV/PIV3 RNA (e.g., mRNA) vaccine is sufficient to produce a 500, 1000, 1500, 2000, 2500, 3000, 3500, 4000, 4500, 5000, 5500, 6000, 6500, 7000, 7500, 8000, 8500, 9000, 9500, 10,000, 11000, 12,000, 13,000, 14,000, 15,000, 16,000, 17,000, 18,000, 19000, 20,000 or higher neutralizing titer. In some embodiments, neutralizing titer is produced 1-72 hours post administration. For example, neutralizing titers may be produced 1-10, 1-20, 1-30, 1-40, 1-50, 1-60, 1-70, 1-72, 10-20, 10-30, 10-40, 10-50, 10-60, 10-70, 10-72, 20-30, 20-40, 20-50, 20-60, 20-70, 20-72, 30-40, 30-50, 30-60, 30-70, 30-72, 40-50, 40-60, 40-70, 40-72, 50-60, 50-70, 50-72, 60-70, 60-72, or 70-72 hours post administration. In some embodiments, neutralizing titers may be produced 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, 50, 51, 52, 53, 54, 55, 56, 57, 58, 59, 60, 61, 62, 63, 64, 65, 66, 67, 68, 69, 70, 71, or 72 hours post administration. In some embodiments, neutralizing titer is produced within 14 days of vaccine administration. In some embodiments, neutralizing titer is produced within 5, 6, 7, 8, 9, 10, 11, 12, 13, or 14 days of vaccine administration.

In some embodiments, an effective dose of the hMPV/PIV3 RNA (e.g., mRNA) vaccine is comparable to the dose of the vaccine required to produce, in a cotton rat model or an African Green Monkey model, a neutralization titer of at least 6, at least 7, at least 8, or at least 9 on a log 2 based scale, as measured by 60% plaque reduction neutralization test (PRNT). In some embodiments, an effective dose of the hMPV/PIV3 RNA (e.g., mRNA) vaccine is comparable to the dose of the vaccine required to produce, in a cotton rat model or an African Green Monkey model, a neutralization titer of 6, 7, 8, 9, 10, 11 or 12 on a log 2 based scale, as measured by 60% plaque reduction neutralization test (PRNT). In some embodiments, an effective dose of the hMPV/PIV3 RNA (e.g., mRNA) vaccine is comparable to the dose of the vaccine required to produce, in a cotton rat model or an African Green Monkey model, a neutralization titer of 6-12, 7-12, 8-12, or 9-12 on a log 2 based scale, as measured by 60% plaque reduction neutralization test (PRNT). In some embodiments, the high neutralizing antibody titer is induced within 14 days of vaccine administration. In some embodiments, the high neutralizing antibody titer is induced within 21 days of vaccine administration. In some embodiments, the high neutralizing antibody titer is induced within 28 days of vaccine administration.

In some embodiments, an anti-hMPV F protein and/or anti-PIV3 F protein antibody titer produced in a subject is increased by at least 1 log relative to a control. For example, anti-hMPV F protein and/or anti-PIV3 F protein antibody titer produced in a subject may be increased by at least 1.5, at least 2, at least 2.5, or at least 3 log relative to a control. In some embodiments, the anti-hMPV F protein and/or anti-PIV3 F protein polypeptide antibody titer produced in the subject is increased by 1, 1.5, 2, 2.5 or 3 log relative to a control. In some embodiments, the anti-hMPV F protein and/or anti-PIV3 F protein antibody titer produced in the subject is increased by 1-3 log relative to a control. For example, the anti-hMPV F protein and/or anti-PIV3 F protein antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-hMPV F protein and/or anti-PIV3 F protein antibody titer produced in a subject is increased at least 2 times relative to a control. For example, the anti-hMPV F protein and/or anti-PIV3 F protein antibody titer produced in a subject may be increased at least 3 times, at least 4 times, at least 5 times, at least 6 times, at least 7 times, at least 8 times, at least 9 times, or at least 10 times relative to a control. In some embodiments, the anti-hMPV F protein and/or anti-PIV3 F protein antibody titer produced in the subject is increased 2, 3, 4, 5, 6, 7, 8, 9, or 10 times relative to a control. In some embodiments, the anti-hMPV F protein and/or anti-PIV3 F protein antibody titer produced in a subject is increased 2-10 times relative to a control. For example, the anti-hMPV F protein and/or anti-PIV3 F protein antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5- 9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-hMPV F protein and/or anti-PIV3 F protein antibody titer produced in a subject who has not been administered a RNA (e.g., mRNA) vaccine of the present disclosure. In some embodiments, a control is an anti-hMPV F protein and/or anti-PIV3 F protein (antibody titer produced in a subject who has been administered a live attenuated hMPV and/or hPIV3 vaccine or an inactivated hMPV and/or hPIV3 vaccine. An attenuated vaccine is a vaccine produced by reducing the virulence of a viable (live). An attenuated virus is altered in a manner that renders it harmless or less virulent relative to live, unmodified virus. In some embodiments, a control is an anti-hMPV F protein and/or anti-PIV3 F protein antibody titer produced in a subject administered inactivated hMPV and/or hPIV3 vaccine. In some embodiments, a control is anti-hMPV F protein and/or anti-PIV3 F protein antibody titer produced in a subject administered a recombinant or purified hMPV and/or hPIV3 protein vaccine. Recombinant protein vaccines typically include protein antigens that either have been produced in a heterologous expression system (e.g., bacteria or yeast) or purified from large amounts of the pathogenic organism. In some embodiments, a control is an antibody titer produced in a subject who has been administered an hMPV and/or hPIV3 virus-like particle (VLP) vaccine. For example, an hMPV VLP vaccine used as a control may be a hMPV VLPs, comprising (or consisting of) viral matrix (M) and fusion (F) proteins, generated by expressing viral proteins in suspension-adapted human embryonic kidney epithelial (293-F) cells (see, e.g., Cox R G et al., *J Virol.* 2014 June; 88(11): 6368-6379, the contents of which are herein incorporated by reference).

In some embodiments, an effective amount of a hMPV/hPIV3 RNA (e.g., mRNA) vaccine is a dose that is reduced compared to the standard of care dose of a recombinant hMPV and/or hPIV3 protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hMPV and/or hPIV3 protein vaccine, or a live attenuated or inactivated hMPV and/or hPIV3 vaccine, that a physician/clinician or other medical professional would administer to a subject to treat or prevent hMPV and/or hPIV3, or a hMPV- and/or hPIV3-related condition, while following the standard of care guideline for treating or preventing hMPV and/or hPIV3, or a hMPV- and/or hPIV3-related condition.

In some embodiments, the an anti-hMPV F protein and/or anti-PIV3 F protein antibody titer produced in a subject administered an effective amount of a RNA (e.g., mRNA) vaccine is equivalent to an an anti-hMPV F protein and/or anti-PIV3 F protein antibody titer produced in a control subject administered a standard of care dose of a recombinant or purified hMPV and/or hPIV3 protein vaccine or a live attenuated or inactivated hMPV and/or hPIV3 vaccine.

In some embodiments, an effective amount of a RNA (e.g., mRNA) vaccine is a dose equivalent to an at least 2-fold reduction in a standard of care dose of a recombinant or purified hMPV and/or hPIV3 protein vaccine. For example, an effective amount of a RNA (e.g., mRNA) vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified hMPV and/or hPIV3 protein vaccine. In some embodiments, an effective amount of a RNA (e.g., mRNA) vaccine is a dose equivalent to an at least at least 100-fold, at least 500-fold, or at least 1000-fold reduction in a standard of care dose of a recombinant or purified hMPV and/or hPIV3 protein vaccine. In some embodiments, an effective amount of a RNA (e.g., mRNA) vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified hMPV and/or hPIV3 protein vaccine. In some embodiments, the anti-hMPV F protein and/or anti-hPIV F protein antibody titer produced in a subject administered an effective amount of a RNA (e.g., mRNA) vaccine is equivalent to an anti-hMPV F protein and/or anti-hPIV F protein antibody titer produced in a control subject administered the standard of care dose of a recombinant or protein hMPV and/or hPIV3, protein vaccine or a live attenuated or inactivated hMPV and/or hPIV3 vaccine. In some embodiments, an effective amount of a RNA (e.g., mRNA) vaccine is a dose equivalent to a 2-fold to 1000-fold (e.g., 2-fold to 100-fold, 10-fold to 1000-fold) reduction in the standard of care dose of a recombinant or purified hMPV and/or hPIV3 protein vaccine, wherein the anti-hMPV F protein and/or anti-hPIV F protein antibody titer produced in the subject is equivalent to an anti-hMPV F protein and/or anti-hPIV F protein antibody titer produced in a control subject administered the standard of care dose of a recombinant or purified hMPV and/or hPIV3 protein vaccine or a live attenuated or inactivated hMPV and/or hPIV3 vaccine.

In some embodiments, the effective amount of a hMPV/hPIV3 RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant hMPV and/or hPIV3 protein vaccine. In some embodiments, the anti-HMP F protein and/or anti-hPIV3 F protein antibody titer produced in the subject is equivalent to an anti-hMPV F protein and/or anti-hPIV F protein antibody titer produced in a control subject administered the standard of care dose of a recombinant or purified hMPV and/or hPIV3 protein vaccine or a live attenuated or inactivated hMPV and/or hPIV3 vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant hMPV and/or hPIV3 protein vaccine. In some embodiments, an anti-hMPV F protein and/or anti-hPIV3 F protein antibody titer produced in the subject is equivalent to an an anti-hMPV F protein and/or anti-hPIV3 F protein antibody titer produced in a control subject administered the standard of care dose of a recombinant or purified hMPV and/or hPIV3 protein vaccine or a live attenuated or inactivated hMPV and/or hPIV3 vaccine.

In some embodiments, the effective amount is 5 μg-100 μg of the RNA polynucleotide encoding hMPV F protein and/or 5 μg-100 μg of the RNA polynucleotide encoding hPIV3 F protein. For example, the effective amount may be 5 μg-10 μg, 5 μg-20 μg, 5 μg-30 μg, 5 μg-40 μg, 5 μg-50 μg, 5 μg-60 μg, 5 μg-70 μg, 5 μg-80 μg, 5 μg-90 μg, 5 μg-100 μg, 10 μg-20 μg, 10 μg-30 μg, 10 μg-40 μg, 10 μg-50 μg, 10 μg-60 μg, 10 μg-70 μg, 10 μg-80 μg, 10 μg-90 μg, 10 μg-100 μg, 25 μg-30 μg, 25 μg-40 μg, 25 μg-50 μg, 25 μg-60 μg, 25 μg-70 μg, 25 μg-80 μg, 25 μg-90 μg, 25 μg-100 μg, 50 μg-60 μg, 50 μg-70 μg, 50 μg-80 μg, 50 μg-90 μg, or 50 μg-100 μg of the RNA polynucleotide encoding hMPV F protein and/or 5 μg-10 μg, 5 μg-20 μg, 5 μg-30 μg, 5 μg-40 μg, 5 μg-50 μg, 5 μg-60 μg, 5 μg-70 μg, 5 μg-80 μg, 5 μg-90 μg, 5 μg-100 μg, 10 μg-20 μg, 10 μg-30 μg, 10 μg-40 μg, 10 μg-50 μg, 10 μg-60 μg, 10 μg-70 μg, 10 μg-80 μg, 10 μg-90 μg, 10 μg-100 μg, 25 μg-30 μg, 25 μg-40 μg, 25 μg-50 μg, 25 μg-60 μg, 25 μg-70 μg, 25 μg-80 μg, 25 μg-90 μg, 25 μg-100 μg, 50 μg-60 μg, 50 μg-70 μg, 50 μg-80 μg, 50 μg-90 μg, or 50 μg-100 μg of the RNA polynucleotide encoding hPIV3 F protein. In some embodiments, the effective amount is 5 μg, 10 μg, 12.5 μg, 20 μg, 25 μg, 30 μg, 40 μg, 50 μg, 60 μg, 70 μg, 80 μg, 90 μg, 100 μg of the RNA polynucleotide encoding hMPV F protein and/or 5 μg, 10 μg, 12.5 μg, 20 μg, 25 μg, 30 μg, 40 μg, 50 μg, 60 μg, 70 μg, 80 μg, 90 μg, 100 μg of the RNA polynucleotide encoding hPIV3 F protein. In some embodiments, the effective amount is 12.5 μg of the RNA polynucleotide encoding hMPV F protein and/or 12.5 μg of the RNA polynucleotide encoding hPIV3 F protein. In some embodiments, the effective amount is 25 μg of the RNA polynucleotide encoding hMPV F protein and/or 25 μg of the RNA polynucleotide encoding hPIV3 F protein. In some embodiments, the effective amount is 50 μg of the RNA polynucleotide encoding hMPV F protein and/or 50 μg of the RNA polynucleotide encoding hPIV3 F protein. In some embodiments, the effective amount is 100 μg of the RNA polynucleotide encoding hMPV F protein and/or 100 μg of the RNA polynucleotide encoding hPIV3 F protein.

In some embodiments, an effective dose of the RNA (e.g., mRNA) vaccine described herein is sufficient to produce detectable levels of F protein as measured in serum of the subject at 1-72 hours post administration. For example, hMPV F protein and/or hPIV3 F protein may be detected at 1, 2, 3, 4, 5, 6, 7, 8, 9, 10, 15, 20, 25, 30, 35, 40, 45, 50, 55, 60, 65, 70, or 72 hours post administration. In some embodiments, an effective dose of the RNA (e.g., mRNA) vaccine described herein is sufficient to produce detectable levels of F protein as measured in serum of the subject within 14 days of administration. In some embodiments, the cut off index of the antigen is 1-2 (e.g., 1, 1.5, or 2). In some embodiments, wherein the effective dose is sufficient to produce a 1,000-10,000 neutralization titer produced by neutralizing antibody against hMPV F protein and/or hPIV3 F protein as measured in serum of the subject at 1-72 hours post administration. In some embodiments, wherein the effective dose is sufficient to produce a 1,000-10,000 neutralization titer produced by neutralizing antibody against hMPV F protein and/or hPIV3 F protein as measured in serum of the subject within 14 days of administration. In some embodiments, the cut-off index of hMPV F protein and/or hPIV3 F protein is 1-2.

Vaccine Efficacy

Some aspects of the present disclosure provide formulations of the hMPV/hPIV3 RNA (e.g., mRNA) vaccine, wherein the hMPV/hPIV3 RNA vaccine is formulated in an effective amount to produce an antigen specific immune response in a subject (e.g., production of antibodies specific to an anti-hMPV/hPIV3 antigen). "An effective amount" is a dose of a hMPV/hPIV3 RNA (e.g., mRNA) vaccine effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) hMPV/hPIV3 protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-hMPV/hPIV3 antigen antibody titer produced in a subject administered a hMPV/hPIV3 RNA (e.g., mRNA) vaccine as provided herein. An antibody titer is a measurement of the amount of antibodies within a subject, for example, antibodies that are specific to a particular antigen (e.g., an anti-hMPV/hPIV3 antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the hMPV/hPIV3 RNA (e.g., mRNA) vaccine.

In some embodiments, an anti-hMPV/hPIV3 antigen antibody titer produced in a subject is increased by at least 1 log relative to a control. For example, anti-hMPV/hPIV3 antigen antibody titer produced in a subject may be increased by at least 1.5, at least 2, at least 2.5, or at least 3 log relative to a control. In some embodiments, the anti-hMPV/hPIV3 antigen antibody titer produced in the subject is increased by 1, 1.5, 2, 2.5 or 3 log relative to a control. In some embodiments, the anti-hMPV/hPIV3 antigen antibody titer produced in the subject is increased by 1-3 log relative to a control. For example, the anti-hMPV/hPIV3 antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-hMPV/hPIV3 antigen antibody titer produced in a subject is increased at least 2 times relative to a control. For example, the anti-hMPV/hPIV3 antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-hMPV/hPIV3 antigen antibody titer produced in the subject is increased 2, 3, 4, 5, 6, 7, 8, 9, or 10 times relative to a control. In some embodiments, the anti-hMPV/hPIV3 antigen antibody titer produced in a subject is increased 2-10 times relative to a control. For example, the anti-hMPV/hPIV3 antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-hMPV/hPIV3 antigen antibody titer produced in a subject who has not been administered a hMPV/hPIV3 RNA (e.g., mRNA) vaccine. In some embodiments, a control is an anti-hMPV/hPIV3 antigen antibody titer produced in a subject administered a recombinant or purified hMPV/hPIV3 protein vaccine. Recombinant protein vaccines typically include protein antigens that either have been produced in a heterologous expression system (e.g., bacteria or yeast) or purified from large amounts of the pathogenic organism.

In some embodiments, the ability of a hMPV/hPIV3 vaccine to be effective is measured in a murine model. For example, the hMPV/hPIV3 vaccines may be administered to a murine model and the murine model assayed for induction of neutralizing antibody titers. Viral challenge studies may also be used to assess the efficacy of a vaccine of the present disclosure. For example, the hMPV/hPIV3 vaccines may be administered to a murine model, the murine model challenged with hMPV/hPIV3, and the murine model assayed for survival and/or immune response (e.g., neutralizing antibody response, T cell response (e.g., cytokine response)).

In some embodiments, an effective amount of a hMPV/hPIV3 RNA (e.g., mRNA) vaccine is a dose that is reduced compared to the standard of care dose of a recombinant hMPV/hPIV3 protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified hMPV/hPIV3 protein vaccine, or a live attenuated or inactivated hMPV/hPIV3 vaccine, or a hMPV/hPIV3 VLP vaccine, that a physician/clinician or other medical professional would administer to a subject to treat or prevent hMPV/hPIV3, or a hMPV/hPIV3-related condition, while following the standard of care guideline for treating or preventing hMPV/hPIV3, or a hMPV/hPIV3-related condition.

In some embodiments, the anti-hMPV/hPIV3 antigen antibody titer produced in a subject administered an effective amount of a hMPV/hPIV3 RNA vaccine is equivalent to an anti-hMPV/hPIV3 antigen antibody titer produced in a control subject administered a standard of care dose of a recombinant or purified hMPV/hPIV3 protein vaccine, or a live attenuated or inactivated hMPV/hPIV3 vaccine, or a hMPV/hPIV3 VLP vaccine.

In some embodiments, an effective amount of a hMPV/hPIV3 RNA (e.g., mRNA) vaccine is a dose equivalent to an at least 2-fold reduction in a standard of care dose of a recombinant or purified hMPV/hPIV3 protein vaccine. For example, an effective amount of a hMPV/hPIV3 RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified hMPV/hPIV3 protein vaccine. In some embodiments, an effective amount of a hMPV/hPIV3 RNA vaccine is a dose equivalent to an at least at least 100-fold, at least 500-fold, or at least 1000-fold reduction in a standard of care dose of a recombinant or purified hMPV/hPIV3 protein vaccine. In some embodiments, an effective amount of a hMPV/hPIV3 RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified hMPV/hPIV3 protein vaccine. In some embodiments, the anti-hMPV/hPIV3 antigen antibody titer produced in a subject administered an effective amount of a hMPV/hPIV3 RNA vaccine is equivalent to an anti-hMPV/hPIV3 antigen antibody titer produced in a control subject administered the standard of care dose of a recombinant or protein hMPV/ hPIV3 protein vaccine, or a live attenuated or inactivated hMPV/hPIV3 vaccine, or a hMPV/hPIV3 VLP vaccine. In some embodiments, an effective amount of a hMPV/hPIV3 RNA (e.g., mRNA) vaccine is a dose equivalent to a 2-fold to 1000-fold (e.g., 2-fold to 100-fold, 10-fold to 1000-fold) reduction in the standard of care dose of a recombinant or purified hMPV/hPIV3 protein vaccine, wherein the anti-hMPV/hPIV3 antigen antibody titer produced in the subject is equivalent to an anti-hMPV/hPIV3 antigen antibody titer produced in a control subject administered the standard of care dose of a recombinant or purified hMPV/hPIV3 protein vaccine, or a live attenuated or inactivated hMPV/hPIV3 vaccine, or a hMPV/hPIV3 VLP vaccine.

In some embodiments, the effective amount of a hMPV/hPIV3 RNA (e.g., mRNA) vaccine is a total dose of 50-1000 μg. In some embodiments, the effective amount of a hMPV/hPIV3 RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a hMPV/hPIV3 RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 administered to the subject a total of two times. In some embodiments, the effective amount of a hMPV/hPIV3 RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a hMPV/hPIV3 RNA (e.g., mRNA) vaccine is a total dose of 25, 50, 100, 150, 200, 250, 300, 350, 400, 450, or 500 μg administered to the subject a total of two times.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, efficacy of the hMPV/hPIV3 vaccine is at least 60% relative to unvaccinated control subjects. For example, efficacy of the hMPV/hPIV3 vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a hMPV/hPIV3 vaccine of the present disclosure is sufficient to provide sterilizing immunity in the subject for at least 1 year. For example, the effective amount of a hMPV/hPIV3 vaccine of the present disclosure is sufficient to provide sterilizing immunity in the subject for at least 2 years, at least 3 years, at least 4 years, or at least 5 years. In some embodiments, the effective amount of a hMPV/hPIV3 vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a hMPV/hPIV3 vaccine of the present disclosure is sufficient to produce detectable levels of hMPV/hPIV3 antigen as measured in serum of the subject at 1-72 hours post administration. In some embodiments, the effective amount of a hMPV/hPIV3 vaccine of the present disclosure is sufficient to produce detectable levels of hMPV/hPIV3 antigen as measured in serum of the subject within 14 days (e.g., at 7-14 days) post administration.

Titer. An antibody titer is a measurement of the amount of antibodies within a subject, for example, antibodies that are specific to a particular antigen (e.g., an anti-hMPV/hPIV3 antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of a hMPV/hPIV3 vaccine of the present disclosure is sufficient to produce a 1,000-10,000 neutralizing antibody titer produced by neutralizing antibody against the hMPV/hPIV3 antigen as measured in serum of the subject at 1-72 hours post administration. In some embodiments, the effective amount is sufficient to produce a 1,000-5,000 neutralizing antibody titer produced by neutralizing antibody against the hMPV/hPIV3 antigen as measured in serum of the subject at 1-72 hours post administration. In some embodiments, the effective amount is sufficient to produce a 5,000-10,000 neutralizing antibody titer produced by neutralizing antibody against the hMPV/hPIV3 antigen as measured in serum of the subject at 1-72 hours post administration.

In some embodiments, the effective amount of a hMPV/hPIV3 vaccine of the present disclosure is sufficient to produce a 1,000-10,000 neutralizing antibody titer produced by neutralizing antibody against the hMPV/hPIV3 antigen as measured in serum of the subject within 14 days of vaccine administration. In some embodiments, the effective amount is sufficient to produce a 1,000-5,000 neutralizing antibody titer produced by neutralizing antibody against the hMPV/hPIV3 antigen as measured in serum of the subject within 14 days of vaccine administration. In some embodiments, the effective amount is sufficient to produce a 5,000-10,000 neutralizing antibody titer produced by neutralizing antibody against the hMPV/hPIV3 antigen as measured in serum of the subject within 14 days of vaccine administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-hMPV/hPIV3 antigen antibody titer produced in the subject is increased by at least 1 log relative to a control. For example, an anti-hMPV/hPIV3 antigen antibody titer produced in the subject may be increased by at least 2, 3, 4, 5, 6, 7, 8, 9 or 10 log relative to a control.

In some embodiments, an anti-hMPV/hPIV3 antigen antibody titer produced in the subject is increased at least 2 times relative to a control. For example, an anti-hMPV/hPIV3 antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated hMPV/hPIV3 vaccine, an inactivated hMPV/hPIV3 vaccine, or a protein subunit hMPV/hPIV3 vaccine.

EXAMPLES

The data provided below demonstrates that RNA vaccines comprising hMPV/hPIV3 RNA polynucleotides, formulated in lipid nanoparticles comprising Compound 25 of Formula (I), protect animals from challenge by both viruses. Virus was not detectable in the lung or nose, and there was no evidence of interference between vaccine components. Cotton rats were completely protected from hPIV3 or hMPV after receiving 2 doses of the hMPV/hPIV3 RNA vaccine. hPIV3 F alone had higher neutralization titers than hPIV3 HN or the combination of hPIV3 HN and hPIV3 F. Further, seronegative monkeys were completely protected from hMPV and hPIV3 challenge after 2 doses of the hMPV/hPIV3 RNA vaccine. In naturally seropositive animals, a single dose of vaccine boosted hMPV and hPIV3 titers 4-10 fold. Again, hPIV3 F alone had higher neutralization titers than hPIV3 HN or the combination of hPIV3 HN and hPIV3 F.

Example 1

Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2

Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3' desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG. 2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3

PCR for cDNA Production

PCR procedures for the preparation of cDNA may be performed using 2×KAPA HIFI™ HotStart ReadyMix by Kapa Biosystems (Woburn, Mass.). This system includes 2× KAPA ReadyMix 12.5 µl; Forward Primer (10 µM) 0.75 µl; Reverse Primer (10 µM) 0.75 µl; Template cDNA 100 ng; and dH$_2$O diluted to 25.0 µl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, Calif.) per manufacturer's instructions (up to 5 µg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4

In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 µg |
| 2) | 10x transcription buffer (400 mM Tris-HCl pH 8.0, 190 mM MgCl$_2$, 50 mM DTT, 10 mM Spermidine) | 2.0 µl |
| 3) | Custom NTPs (25 mM each) | 0.2 µl |
| 4) | RNase Inhibitor | 20 U |
| 5) | T7 RNA polymerase | 3000 U |
| 6) | dH$_2$0 | up to 20.0 µl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, Tex.) following the manufacturer's instructions. This kit can purify up to 500 µg of RNA. Following the cleanup, the RNA polynucleotide may be quantified using the NanoDrop and analyzed by agarose gel electrophoresis to confirm the RNA polynucleotide is the proper size and that no degradation of the RNA has occurred.

Example 5

Enzymatic Capping

Capping of a RNA polynucleotide is performed as follows where the mixture includes: IVT RNA 60 µg-180 µg and dH$_2$O up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$O (Up to 28 µl); and incubation at 37° C. for 30 minutes for 60 µg RNA or up to 2 hours for 180 µg of RNA.

The RNA polynucleotide may then be purified using Ambion's MEGACLEAR™ Kit (Austin, Tex.) following the manufacturer's instructions. Following the cleanup, the RNA may be quantified using the NANODROP™ (ThermoFisher, Waltham, Mass.) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6

PolyA Tailing Reaction

Without a poly-T in the cDNA, a poly-A tailing reaction must be performed before cleaning the final product. This is done by mixing capped IVT RNA (100 µl); RNase Inhibitor (20 U); 10× Tailing Buffer (0.5 M Tris-HCl (pH 8.0), 2.5 M NaCl, 100 mM MgCl$_2$) (12.0 µl); 20 mM ATP (6.0 µl); Poly-A Polymerase (20 U); dH$_2$O up to 123.5 µl and incubation at 37° C. for 30 min. If the poly-A tail is already in the transcript, then the tailing reaction may be skipped and proceed directly to cleanup with Ambion's MEGA- CLEAR™ kit (Austin, Tex.) (up to 500 µg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7

Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3"-O-Me-m7G(5)ppp(5') G [the ARCA cap]; G(5) ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 8

Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 9

Agarose Gel Electrophoresis of Modified RNA or RT PCR Products

Individual RNA polynucleotides (200-400 ng in a 20 µl volume) or reverse transcribed PCR products (200-400 ng) may be loaded into a well on a non-denaturing 1.2% Agarose E-Gel (Invitrogen, Carlsbad, Calif.) and run for 12-15 minutes, according to the manufacturer protocol.

Example 10

Nanodrop Modified RNA Quantification and UV Spectral Data

Chemically modified RNA polynucleotides in TE buffer (1 µl) are used for Nanodrop UV absorbance readings to quantitate the yield of each polynucleotide from an chemical synthesis or in vitro transcription reaction.

Example 11

Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 12

Expression of hMPV and hPIV3 Fusion Protein on Cell Surface

Figure 1B:
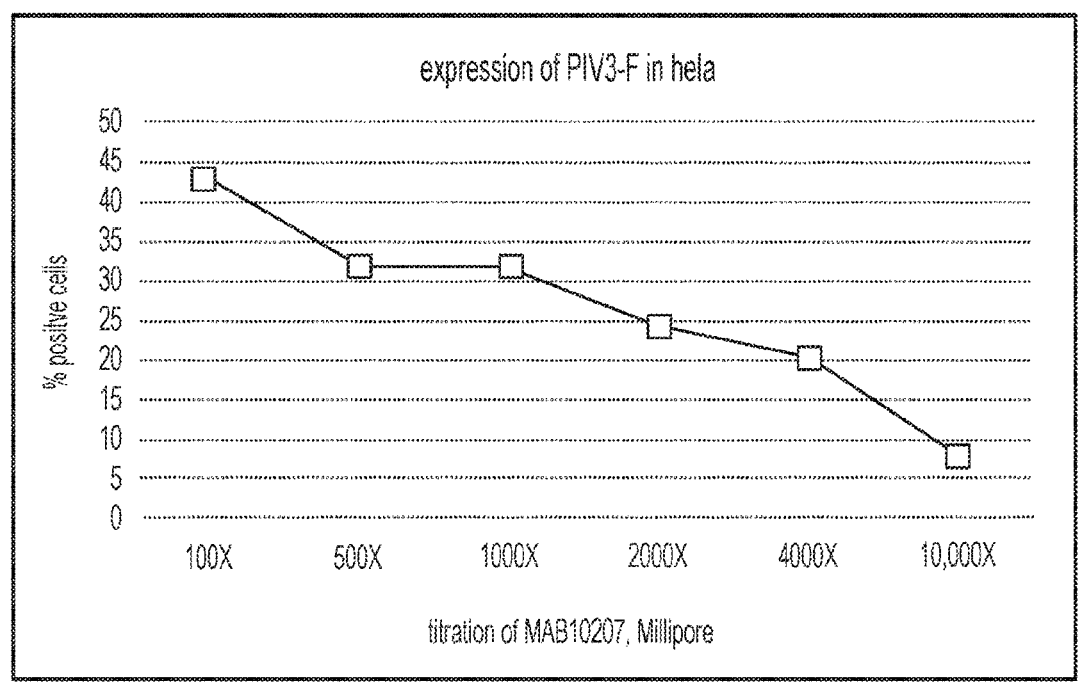

The instant study was designed to show that hMPV/hPIV3 mRNA vaccines encoding the hMPV F protein and the hPIV3 F protein led to cell surface expression of the antigen in cultured Hela cells. The mRNA constructs were transfected into Hela cells. Expression of the hMPV F protein was detected by fluorescent staining using hMPV-F-specific antibodies MPE-8 (Table 1). Untransfected cells (mock) were also stained as negative control. In untransfected cells or cells stained only with secondary antibodies, no hMPV F protein signal was detected, while hMPV F protein signal was detected in transfected cells stained with MPE-8 antibodies (FIG. 1A). Expression of the hPIV3 F protein was detected by staining using the hPIV3-F-specific antibodies MAB10207 and surface expression of hPIV3 protein was detected (FIG. 1B)

TABLE 1

Fluorescent Staining of Cells Transfected with hMPV/HPIV3 mRNA Vaccine Constructs

| Sample | Mean FL4-H |
|---|---|
| Mock-unstained | 494.38 |
| Mock-Secondary only | 3,944.18 |
| Mock-MPE8 (500 nM) | 5,452.55 |
| hMPV-Secondary only | 2,160.82 |
| hMPV-MPE8 (500 nM) | 617,307.76 |

Example 13 hMPV/hPIV3 Cotton Rat Challenge

The instant study was designed to show that the hMPV/hPIV3 mRNA vaccine constructs encoding the hMPV F protein and the hPIV3 F protein induced high levels of neutralizing antibodies in cotton rats and reduced the viral titers in the nose and lungs of the immunized cotton rats after challenge with hMPV or hPIV3 viruses. The study design is shown in Table 2. Animals were dosed on Days 0 and 28 and were challenged on Day 56. Animals were bled on Days −1, 27 and 56. Viral titers were determined 5 days post challenge.

Cotton rats that are negative for hMPV and hPIV3 were divided into 19 groups (n=8), and each group was vaccinated with 2 doses of mRNA vaccines on days 0 and 28. The mRNA vaccines were formulated in either MC3 lipids or Compound 1 lipids. Immunized cotton rats were challenged with a lethal dose of hMPV or hPIV3 on day 57 post immunization. The viral titers in the nose and lungs of the challenged cotton rats were measured on day 5 post challenge and the serum neutralizing antibody titers were measured one day prior to immunization, and on days 27 and 56 post immunization.

Figure 2A:
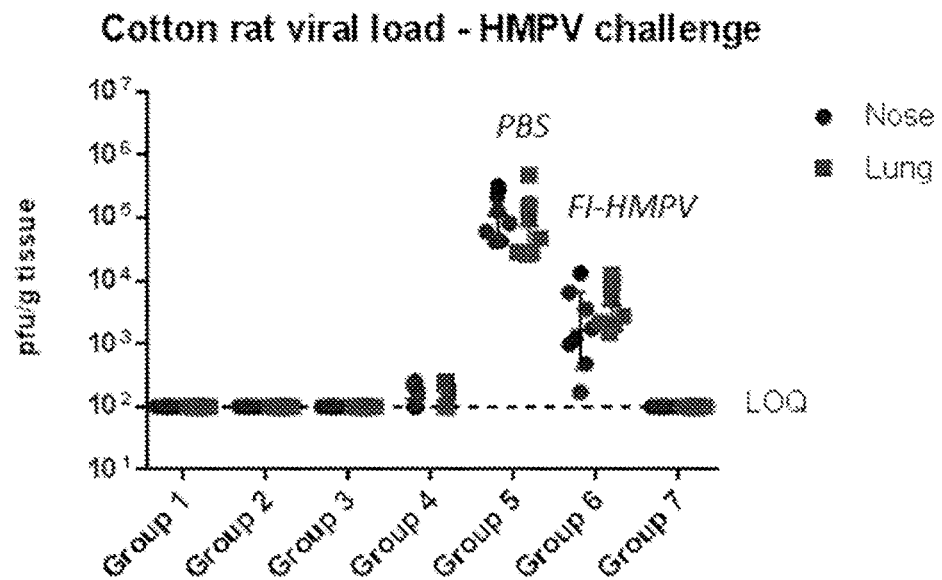
FIGS. 2A-2B are graphs showing the results of cotton rat hMPV and hPIV3 challenge experiments using animals immunized with a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) (see Table 2 for study design).
Figure 2B:
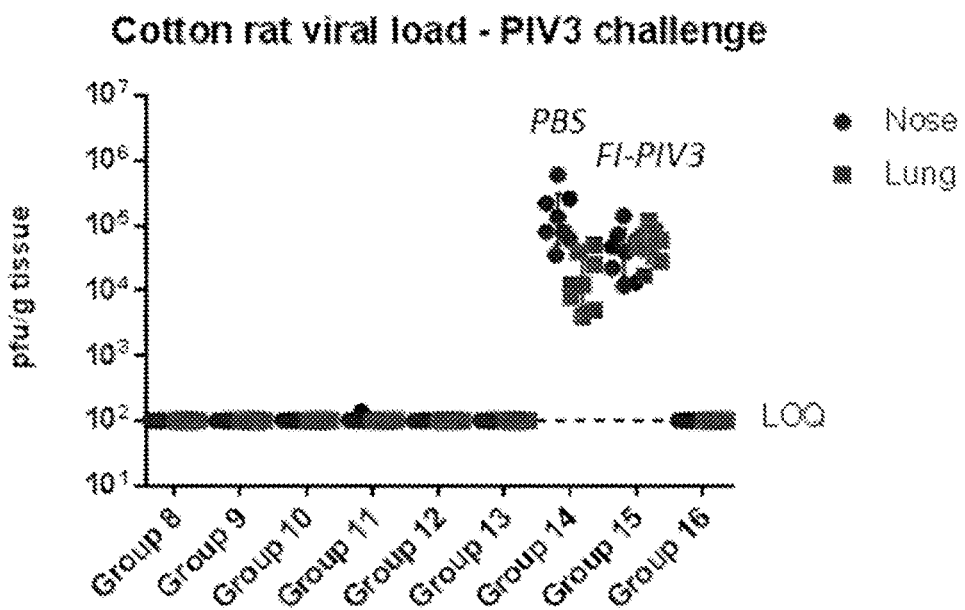
Figure 3A:
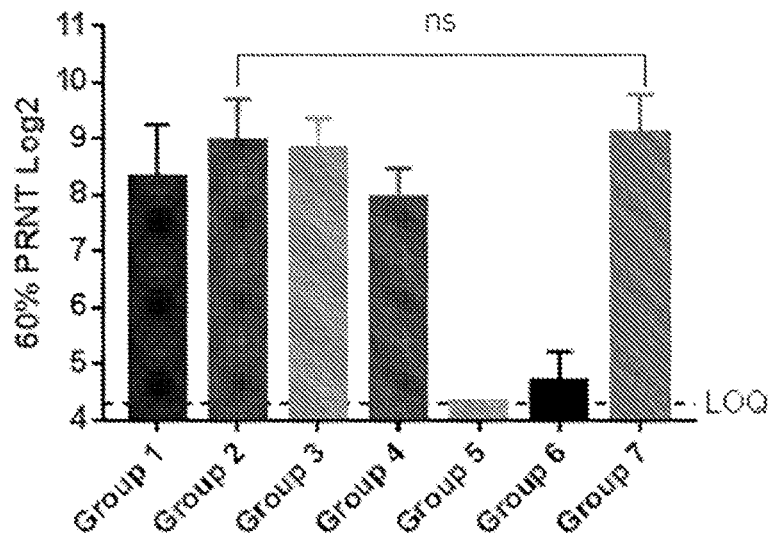
FIGS. 3A-3B are graphs showing neutralizing antibody titers against hMPV/A2 (FIG. 3A) or hPIV3 (FIG. 3B) from the serum of cotton rats immunized with a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) formulated in either MC3 lipids or Compound 1 lipids (see Table 2 for study design). The two formulations yielded comparable levels of neutralizing antibody titers.
Figure 3B:
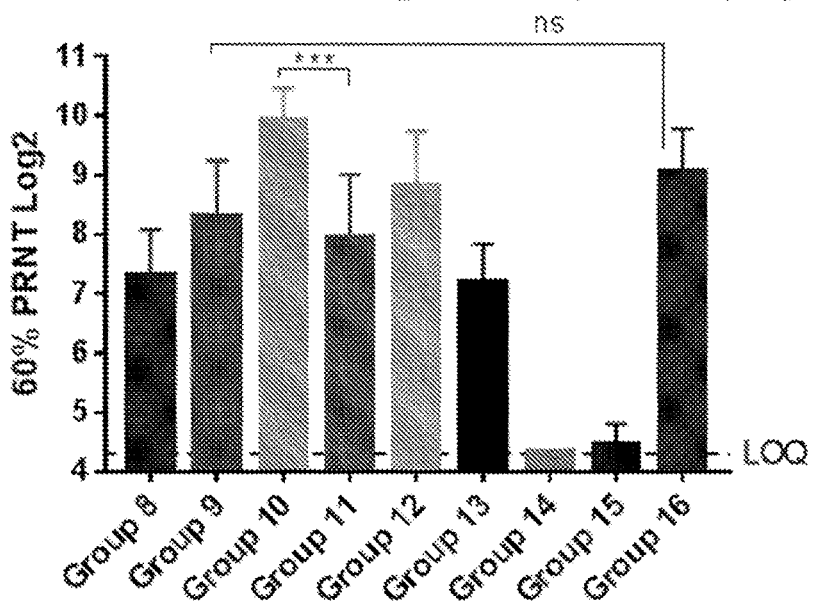

All cotton rats receiving 2 doses of hMPV/HPIV3 mRNA vaccine were completely protected from hMPV or hPIV3 infection, and the two formulations with either MC3 or Compound 1 lipids yielded similar levels of protection (FIGS. 2A-2B). Neutralizing antibody titers in the sera of the immunized cotton rats were analyzed. The results show that the hMPV/HPIV3 mRNA vaccines induced high levels of neutralizing antibodies against hMPV (FIG. 3A) or hPIV3 (FIG. 3B) in immunized cotton rat. Further, mRNA vaccine formulations with Compound 1 or MC3 lipids induced comparable levels of neutralizing antibodies against hMPV (FIG. 3A, compare Group 2 with Group 7). A control group immunized with FI-hMPV showed very low neutralizing antibody titers as expected (FIG. 3A, Group 6). Similarly, mRNA vaccine formulations with Compound 1 or MC3 lipids induced comparable levels of neutralizing antibodies against hPIV3 (FIG. 3, compare Group 9 with Group 16). MRNA vaccines encoding hPIV3 F protein induced neutralizing antibody titers that is 3-fold higher than that of mRNA vaccines encoding hPIV3 HN protein at the same dosage (25 µg) (FIG. 3B, compare Group 10 with Group 11). Further, the presence of mRNA constructs in the mRNA vaccine encoding hMPV antigen does not interfere with the immunogenicity of mRNA constructs encoding hPIV3 antigen (FIG. 3B, compare Group 9 with Group 12).

TABLE 2

Cotton Rat Challenge Study Design

| Cotton Rat Group | n | Vaccine | Dose (µg) | Formulation | Vaccine | Challenge (Day 57) | Endpoint |
|---|---|---|---|---|---|---|---|
| 1 | 8 | hMPV/PIV/RSV | 10/10/30 | Compound 1 | D 0, D 28 | hMPV | Lung and Nose viral titer: Day 5 post challenge and Neutralizing antibody titer (Day-1, D 27, D 56) |
| 2 | 8 | hMPV/PIV | 25/25 | Compound 1 | D 0, D 28 | | |
| 3 | 8 | hMPV | 25 | Compound 1 | D 0, D 28 | | |
| 4 | 8 | hMPV | 10 | Compound 1 | D 0, D 28 | | |
| 5 | 8 | PBS | NA | NA | D 0, D 28 | | |
| 6 | 8 | FI-hMPV | NA | NA | D 0, D 28 | | |
| 7 | 8 | hMPV/PIV | 25/25 | MC3 | D 0, D 28 | | |
| 8 | 8 | hMPV/PIV/RSV | 10/10/30 | Compound 1 | D 0, D 28 | PIV3 | |
| 9 | 8 | hMPV/PIV | 25/25 | Compound 1 | D 0, D 28 | | |
| 10 | 8 | hMPV/PIV-F | 25/25 | Compound 1 | D 0, D 28 | | |
| 11 | 8 | hMPV/PIV-HN | 25/25 | Compound 1 | D 0, D 28 | | |
| 12 | 8 | PIV | 25 | Compound 1 | D 0, D 28 | | |
| 13 | 8 | PIV | 10 | Compound 1 | D 0, D 28 | | |
| 14 | 8 | PBS | NA | NA | D 0, D 28 | | |
| 15 | 8 | FI-PIV3 | NA | NA | D 0, D 28 | | |
| 16 | 8 | hMPV/PIV | 25/25 | MC3 | D 0, D 28 | | |
| 17 | 8 | hMPV/PIV/RSV | 10/10/30 | Compound 1 | D 0, D 28 | RSV | |
| 18 | 8 | RSV | 30 | Compound 1 | D 0, D 28 | | |
| 19 | 8 | PBS | NA | NA | D 0, D 28 | | |

Example 14

Safety and Efficacy of hMPV/hPIV3 Vaccination in Cotton Rat Challenge

The instant study was designed to evaluate the safety and efficacy of human metapneumovirus (hMPV)/parainfluenza 3 (PIV3) mRNA vaccines in the cotton rat model of hMPV or PIV3 challenge. Lipid nanoparticle (LNP)-formulated combinations of mRNA encoding the following antigens:

hMPV fusion (F) protein (Strain: A/TN92-4) (SEQ ID NO: 4)

PIV3 F protein (strain: PER/FLA4815/2008) (SEQ ID NO: 5)

PIV3 hemagglutinin-neuraminidase (HN) protein (Strain: 612507167) (SEQ ID NO: 6)

The mRNAs were formulated in a mixture of 4 lipids, including Compound 1; 1,2-dimyristoyl-sn-glycerol, methoxypolyethyleneglycol (PEG2000-DMG); 1,2-distearoyl-sn-glycero-3-phosphocholine (DSPC); and cholesterol.

The combination vaccine includes hMPV-F and PIV3-F mRNA co-formulated at a 1:1 mass ratio in LNP.

Groups of 8 female cotton rats were immunized with different dose levels of LNP-formulated mRNAs encoding hMPV-F, PIV3-F, and PIV3-HN, either alone or in combination, as indicated in Table 3. Control groups were inoculated with phosphate-buffered saline (PBS), formalin-inactivated (FI)-hMPV, or FI-PIV3. FI-hMPV and FI-PIV3 were produced, and are used as positive controls for vaccine-mediated enhanced respiratory disease (ERD) after hMPV or PIV3 challenge, respectively. All animals were immunized intramuscularly (IM) on Days 0 and 28. Serum was collected on Day 56 for measurement of neutralizing antibody titers to hMPV (Groups 2-6) or PIV3 (Groups 9-15) by 60% plaque reduction neutralization test (PRNT). Animals were challenged intra-nasally on Day 56 with either $10^5$ pfu hMPV/A2 (Groups 2-6) or $10^5$ pfu PIV3 (Groups 9-15). Five days later (Day 61) nasal tissue and lungs were collected. Viral load in both tissues was determined by plaque assay and pulmonary histopathology was evaluated on hematoxylin and eosin (H&E) stained fixed lung sections. Parameters of pulmonary inflation include interstitial pneumonia (inflammatory cell infiltration and thickening of alveolar walls) and alveolitis (cells within the alveolar spaces). Sections were evaluated on a 0-4 severity scale and subsequently converted to a 0-100% histopathology scale.

substrate was added to each well and incubated at room temperature for 10 to 15 minutes. Visible plaques were counted and virus titers were expressed as plaque forming units (pfu) per gram (g) of tissue. Viral titers were reported as mean+standard deviation (SD) of log 10 transformed values for all animals in a group.

PIV3 Lung and Nose Viral Titration

Lung and nose homogenates were clarified by centrifugation and diluted in EMEM. Confluent MA-104 (monkey kidney cells) monolayers were infected in duplicates with diluted homogenates in 24 well plates. After two-hour incubation at 37° C. in a 5% $CO_2$ incubator, the wells were overlaid with 0.75% methylcellulose medium. After 4 days of incubation, the overlays were removed and the cells were fixed and stained with 0.1% crystal violet for one hour and then rinsed and air dried. Plaques were counted and virus titers were expressed as pfu/g of tissue. Viral loads were reported as mean+SD of log 10 transformed values for all animals in a group.

hMPV Neutralizing Antibody Assay

Heat inactivated sera samples were diluted 1:10 with EMEM and serially diluted further 1:4. Diluted serum samples were incubated with hMPV/A2 (25-50 pfu) for 1 hour at room temperature and inoculated in duplicates onto confluent MK-2 monolayers in 24 well plates. After one hour incubation at 37° C. in a 5% $CO_2$ incubator, the wells were overlaid with 0.75% Methylcellulose medium. After 7 days of incubation, the overlays were removed and the cells were fixed in cold acetone/methanol solution for one hour and air dried for immune-staining. Upon blocking the wells with blotto, mouse anti-hMPV N protein at a 1:1000 dilution to each well, followed by HRP conjugated goat anti-mouse IgG diluted at 1:1000. TrueBlue peroxidase substrate was added to each well and incubated at room temperature for 10 to 15 minutes. Visible plaques were counted and the corresponding reciprocal neutralizing antibody titers were determined at the 60% reduction end-point of the virus control using the statistics program "plqrd.manual.entry". Neutralizing titers were reported as mean+/−SD of log 2 transformed titers for all animals in a group.

TABLE 3

| | | | mRNAdose (µg) | | | | Vaccine | Challenge |
|---|---|---|---|---|---|---|---|---|
| Group | n | Vaccine | total | hMPV-F | PIV3-F | PIV3-HN | Schedule | (Day 56) |
| 2 | 8 | hMPV-F/PIV3-F/PIV3-HN | 50 | 25 | 12.5 | 12.5 | Day 0 & 28 | hMPV |
| 3 | 8 | hMPV-F | 25 | 25 | 0 | 0 | Day 0 & 28 | hMPV |
| 4 | 8 | hMPV-F | 10 | 10 | 0 | 0 | Day 0 & 28 | hMPV |
| 5 | 8 | PBS | NA | NA | NA | NA | Day 0 & 28 | hMPV |
| 6 | 8 | FI-hMPV | NA | NA | NA | NA | Day 0 & 28 | hMPV |
| 9 | 8 | hMPV-F/PIV3-F/PIV3-HN | 50 | 25 | 12.5 | 12.5 | Day 0 & 28 | PIV3 |
| 10 | 8 | hMPV-F/PIV3-F | 50 | 25 | 25 | 0 | Day 0 & 28 | PIV3 |
| 11 | 8 | hMPV-F/PIV3-HN | 50 | 25 | 0 | 25 | Day 0 & 28 | PIV3 |
| 12 | 8 | PIV3-F/PIV3-HN | 25 | 0 | 12.5 | 12.5 | Day 0 & 28 | PIV3 |
| 13 | 8 | PIV3-F/PIV3-HN | 10 | 0 | 5 | 5 | Day 0 & 28 | PIV3 |
| 14 | 8 | PBS | NA | NA | NA | NA | Day 0 & 28 | PIV3 |
| 15 | 8 | FI-PIV3 | NA | NA | NA | NA | Day 0 & 28 | PIV3 |

NA—not applicable hMPV Lung and Nose Viral Titration

Lung and nose homogenates were clarified by centrifugation and diluted in EMEM. Confluent MK-2 monolayers were infected in duplicates with diluted homogenates in 24 well plates. After one hour incubation at 37° C. in a 5% $CO_2$ incubator, the wells were overlaid with 0.75% methylcellulose medium. After 7 days of incubation, the overlays were removed and the cells were fixed for one hour and air dried for immune-staining. Upon blocking the wells, mouse anti-hMPV nucleoprotein (N) at a 1:1000 dilution to each well, followed by horseradish peroxidase (HRP) conjugated goat anti-mouse IgG diluted at 1:1000. TrueBlue peroxidase PIV3 Neutralizing Antibody Assay (60% Reduction)

Heat inactivated sera samples were diluted 1:10 with EMEM and serially diluted further 1:4. Diluted serum samples were incubated with PIV3 (25-50 pfu) for 1 hour at room temperature and inoculated in duplicates onto confluent MA-104 monolayers in 24 well plates. After two-hour incubation at 37° C. in a 5% $CO_2$ incubator, the wells were overlaid with 0.75% Methylcellulose medium. After 4 days of incubation, the overlays were removed and the cells were fixed and stained with 0.1% crystal violet for one hour and then rinsed and air dried. The corresponding reciprocal neutralizing antibody titers were determined at the 60% reduction end-point of the virus control using a statistics program. Neutralizing titers were reported as mean+SD of log 2 transformed titers for all animals in a group.

Pulmonary Histopathology

Lungs were dissected and inflated with 10% neutral buffered formalin to their normal volume, and then immersed in the same fixative solution. Following fixation, the lungs were embedded in paraffin, sectioned and stained with H&E. Four parameters of pulmonary inflammation were evaluated: peribronchiolitis (inflammatory cell infiltration around the bronchioles), perivasculitis (inflammatory cell infiltration around the small blood vessels), interstitial pneumonia (inflammatory cell infiltration and thickening of alveolar walls), and alveolitis (cells within the alveolar spaces). Slides were scored blind on a 0-4 severity scale. The scores were subsequently converted to a 0-100% histopathology scale, and reported as mean+SD of all animals in a group.

hMPV neutralizing antibody titers were measured in Day 56 serum from Groups 2-6 (FIG. 4A) and were detected at high levels in all animals immunized with hMPV-F mRNA (Groups 2-4) as well as at low levels in animals immunized with FI-hMPV (Group 6). There was a small dose response to the monovalent hMPV-F vaccine (Group 3 vs. Group 4). Neutralizing antibody titers were similar in Groups 2 and 3, demonstrating no interference of the anti-hMPV antibody response by mRNA encoding hPIV3 proteins.

PIV3 neutralizing antibody titers were measured in Day 56 serum from Groups 9-15 (FIG. 4B) and were detected at high levels in all animals immunized with PIV3-F and/or PIV3-HN mRNA (Groups 9-13) as well as at low levels in animals immunized with FI-PIV3 (Group 15). There was a small dose response to the PIV3-F/PIV3-HN vaccine (Group 12 vs. Group 13). Neutralizing antibody titers were similar in Groups 9 and 12, demonstrating no interference of the anti-PIV3 antibody response by mRNA encoding hMPV-F. The PIV3-F vaccine elicited higher antibody titers than the PIV3-HN vaccine (Group 10 vs. Group 11), suggesting that the PIV3 neutralizing antibody responses induced by the vaccines containing both PIV3-F and PIV3-HN (Groups 9, 12, and 13) were likely dominated primarily by the response to PIV3-F. Among the combination vaccine groups tested, Group 10, the combination of PIV3-F/hMPV-F showed the highest level of PIV3 Neutralizing antibody titers.

Figure 5A:
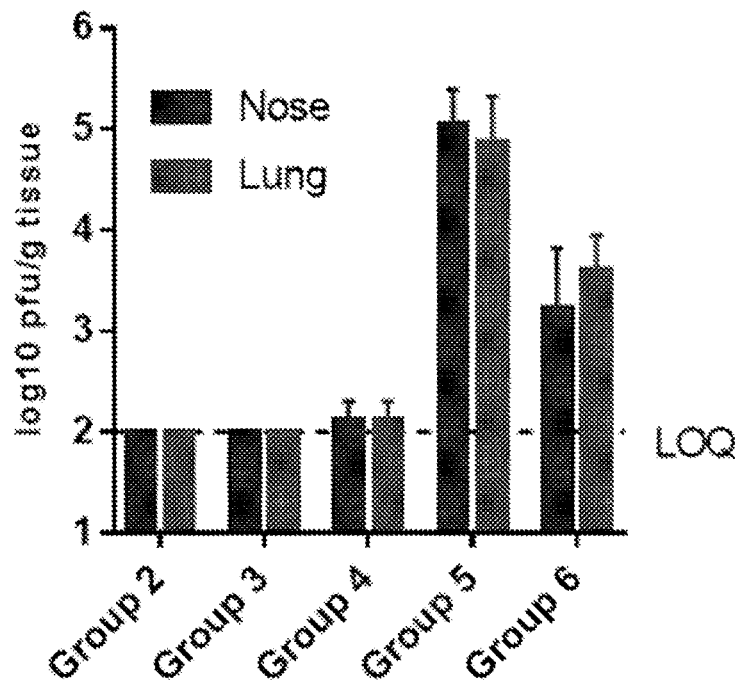
FIGS. 5A-5B are graphs showing viral load after hMPV (FIG. 5A) or PIV3 (FIG. 5B) challenge of cotton rats. High level of virus was detected in PBS control animals (Groups 5 and 14), but was close to or below the limit of quantification in all mRNA-immunized animals (Groups 2-4 and 9-13), demonstrating full protection in both the lung and the nose.
Figure 5B:
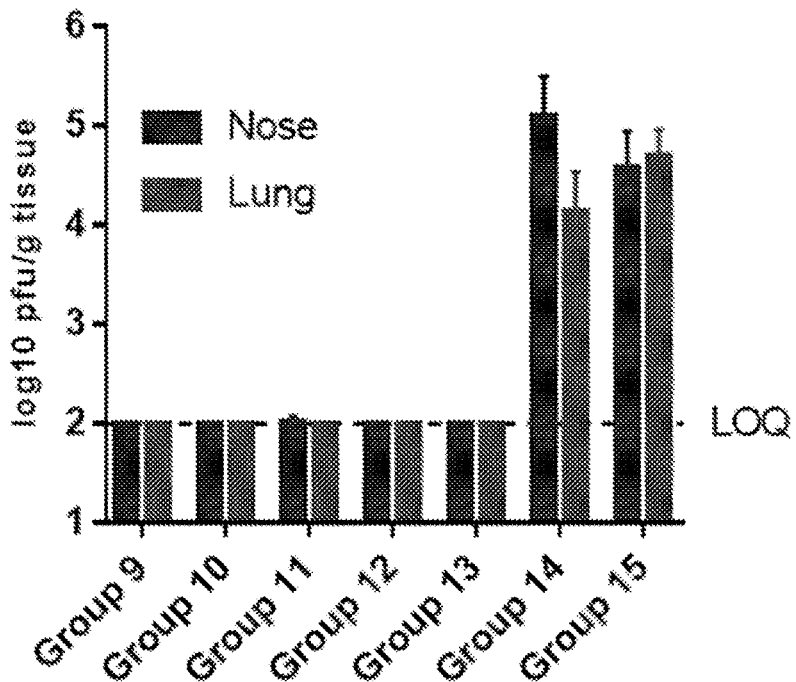

The ability of the hMPV/PIV3 mRNA vaccines to protect against challenge was determined by measuring viral load in lung and nose from immunized animals 5 days after hMPV intranasal challenge (Groups 2-6) (FIG. 5A) or PIV3 challenge (Groups 9-15) (FIG. 5B). High level of virus was detected in PBS control animals (Groups 5 and 14), but was close to or below the limit of quantification in all mRNA-immunized animals (Groups 2-4 and 9-13), demonstrating full protection in both the lung and the nose. The FI-hMPV vaccine (Group 6) afforded only a small level of protection against hMPV challenge, and the FI-PIV3 vaccine (Group 15) provided no protection against PIV3 challenge.

Figure 6A:
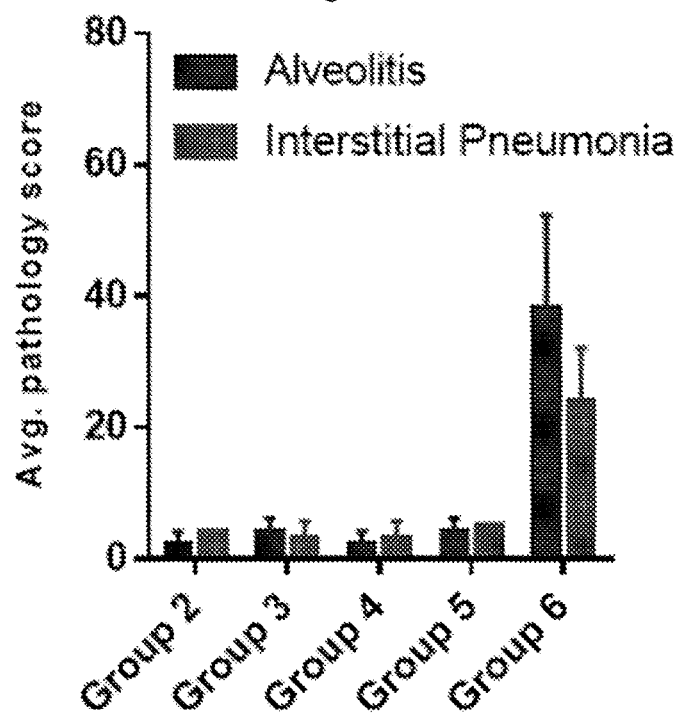
FIGS. 6A-6B are graphs showing the average lung pathology score after hMPV (FIG. 6A) or PIV3 (FIG. 6B) challenge of cotton rats. All mRNA-immunized animals (Groups 2-4 and 9-13) exhibited lung histopathology scores equivalent to the PBS controls (Groups 5 and 14), indicating no vaccine-enhanced respiratory disease (ERD).
Figure 6B:
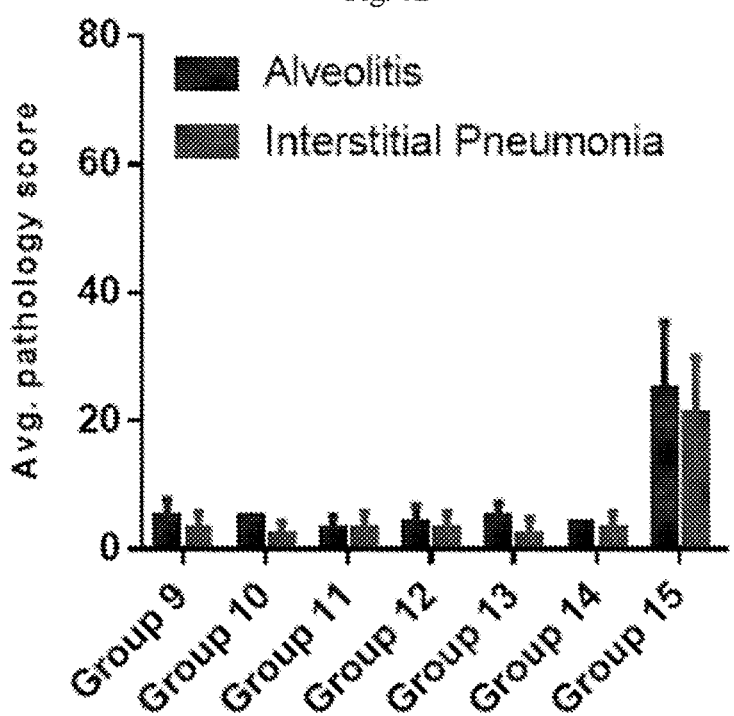

Lung pathology was scored in tissues obtained 5 days after hMPV intranasal challenge (Groups 2-6) (FIG. 6A) or PIV3 challenge (Groups 9-15) (FIG. 6B). All mRNA-immunized animals (Groups 2-4 and 9-13) exhibited lung histopathology scores equivalent to the PBS controls (Groups 5 and 14), indicating no vaccine-enhanced respiratory disease (ERD). In contrast, animals vaccinated with the FI-hMPV (Group 6) or FI-PIV3 (Group 15) positive controls demonstrated elevated levels of both alveolitis and interstitial pneumonia after hMPV or PIV3 challenge, respectively.

Example 15 hMPV/hPIV3 African Green Monkey Challenge

The instant study was designed to show that the hMPV/HPIV3 mRNA vaccine constructs encoding the hMPV F protein and the hPIV3 F protein induced high levels of neutralizing antibodies in African green monkeys and reduced the viral titers in the nose and lungs of the immunized African green monkeys after challenge with hMPV or hPIV3 viruses. The study design is shown in Table 4 (G=Group).

Sero-negative (to both hMPV and hPIV3) African green monkeys were divided into 10 groups (n=3) and hMPV sero-positive or hPIV3 sero-positive African green monkeys were divided into 3 groups, respectively (n=3). Each sero-negative group was vaccinated with 2 doses of mRNA vaccines on days 0 and 28. Each sero-positive group was vaccinated with 1 dose of mRNA vaccines on day 0. The mRNA vaccines were formulated in either MC3 lipids or Compound 1 lipids. All African green monkeys were monitored for injection site reactions 4 hours, 24 hours, and 72 hours after each injection and no erythema or edema was observed in any African green monkey.

Immunized sero-negative African green monkeys were challenged with a lethal dose of hMPV or hPIV3 on day 57 post immunization. The viral titers in the nose and lungs of the challenged sero-negative African green monkeys were measured on day 5 post challenge and the serum neutralizing antibody titers were measured one day prior to immunization, and on days 27 and 56 post immunization. Serum neutralizing antibody titers of sero-positive African green monkeys were measured 28 days prior to immunization, on the day of immunizations, and days 14, 42, and 56 post immunization.

Figure 7A:
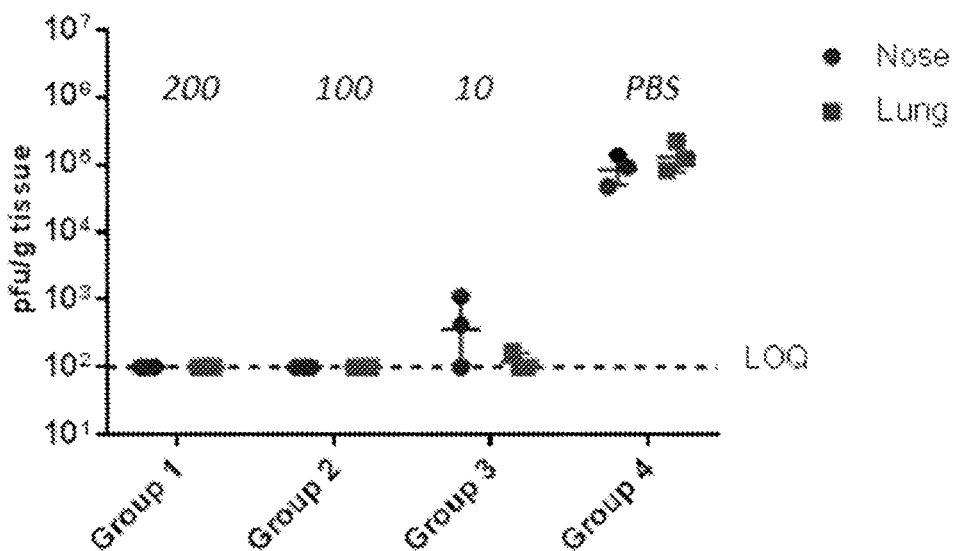
FIGS. 7A-7B are graphs showing results of African green monkey hMPV and hPIV3 challenge experiments using animals immunized with a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) (see Table 3 for study design).
Figure 7B:
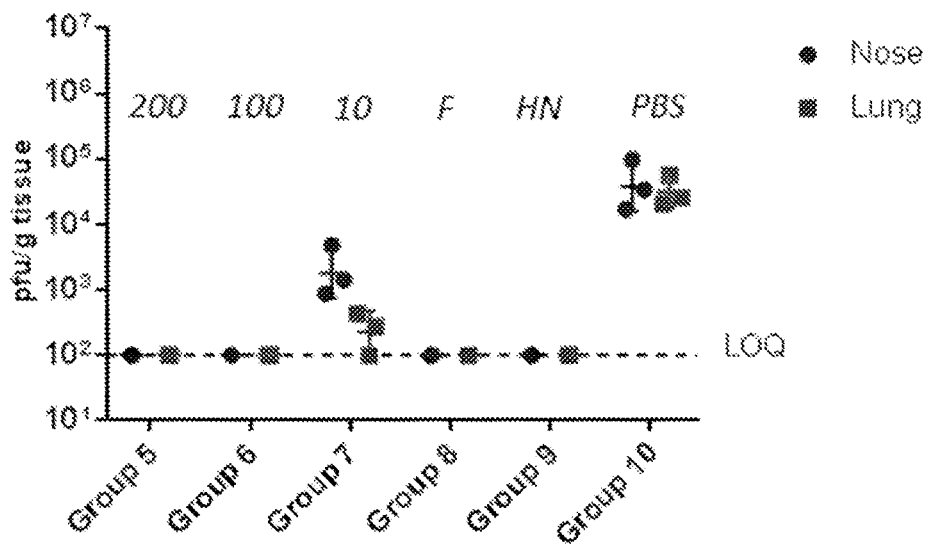
Figure 8A:
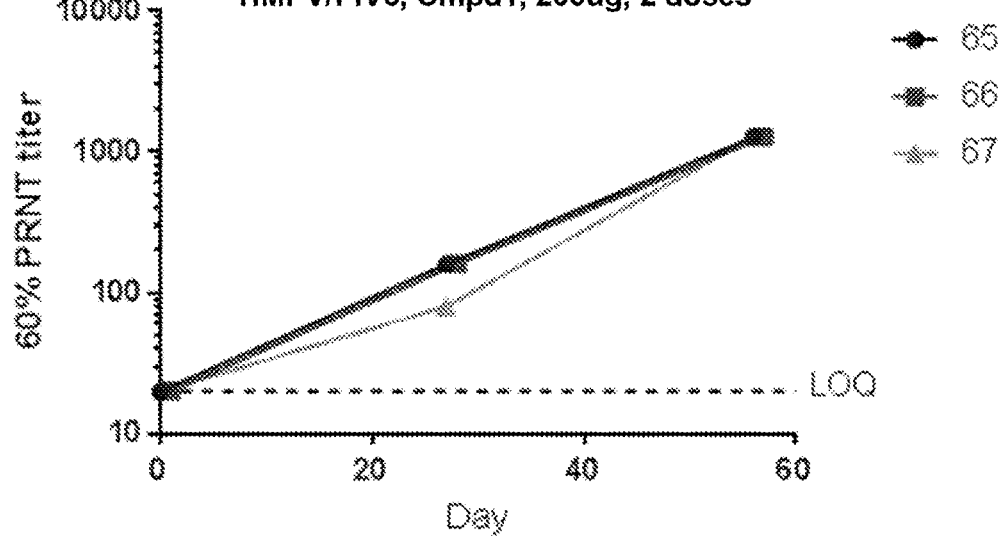
FIGS. 8A-8D are graphs showing neutralizing antibody titers against hMPV in sero-negative African green monkeys immunized with two doses of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) on days 0 and 28 at 200 µg per dose (FIG. 8A), 100 µg per dose (FIG. 8B), 10 µg per dose (FIG. 8C) per dose, or placebo (FIG. 8D). The mRNA vaccines were formulated with Compound 1 lipids.
Figure 8B:
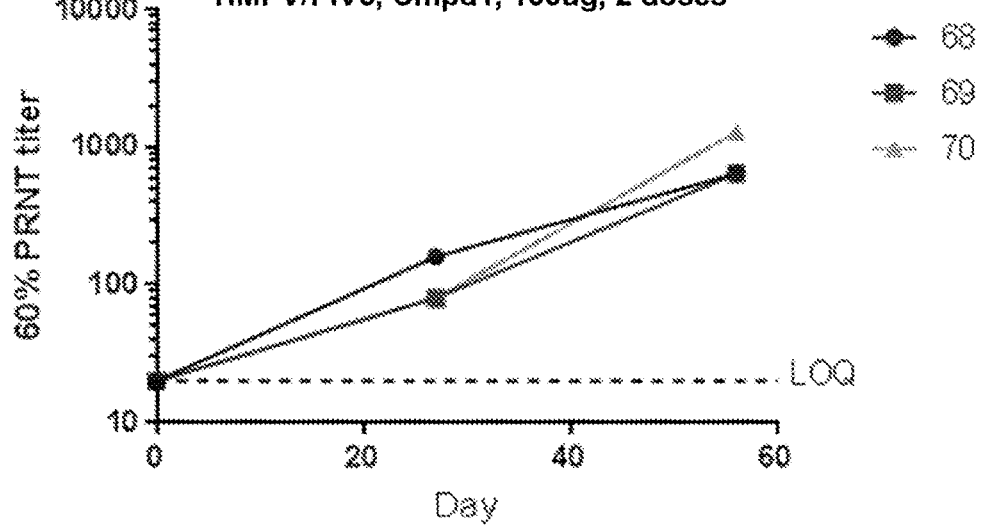
Figure 8C:
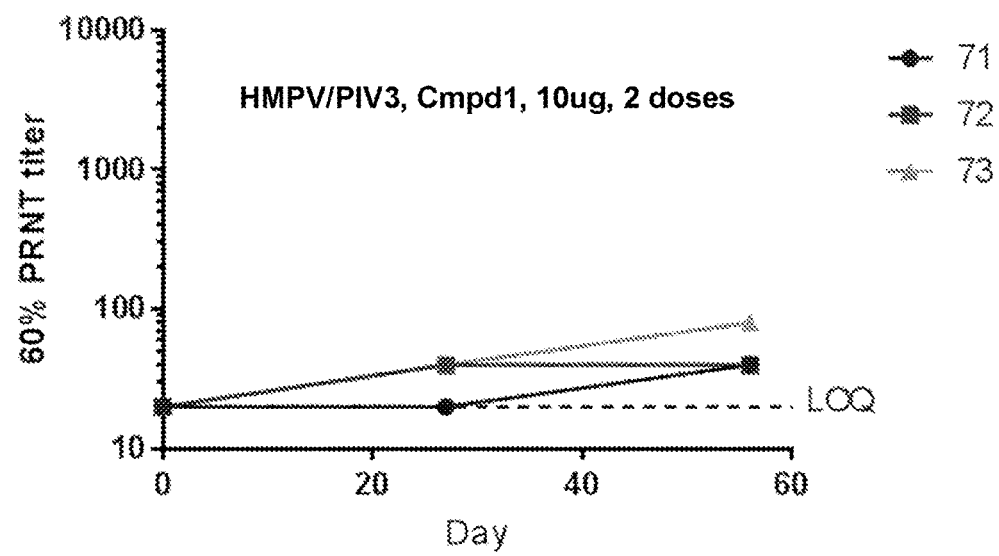
Figure 8D:
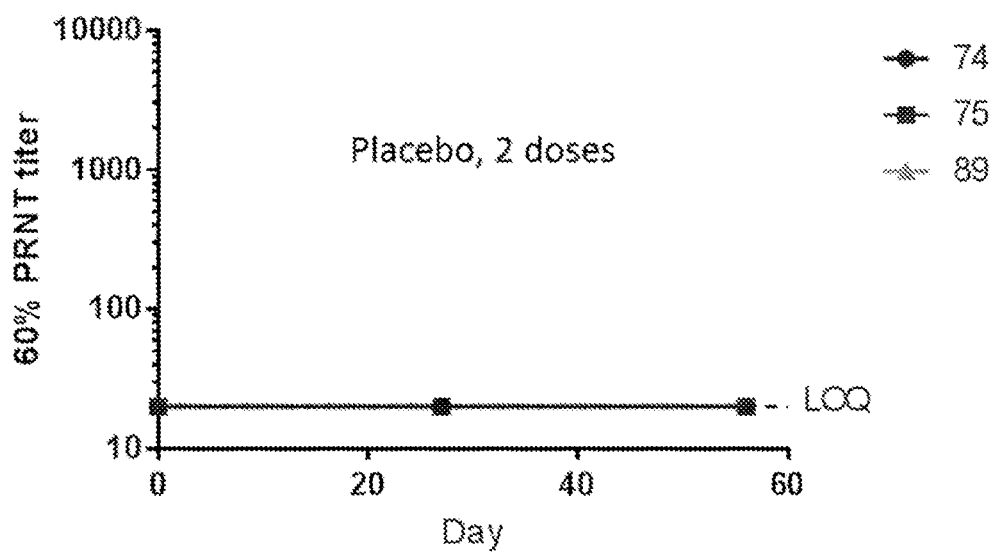
Figure 9A:
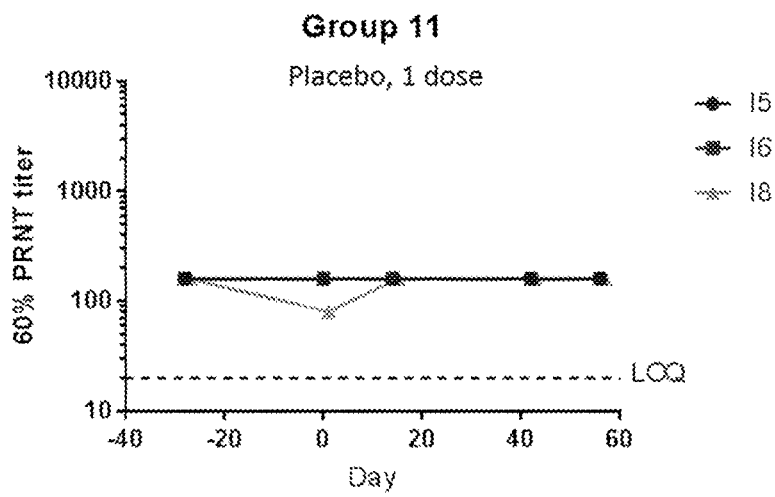
FIGS. 9A-9C are graphs showing neutralizing antibody titers against hMPV in sero-negative African green monkeys immunized with one dose of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) on day 0 at 200 µg per dose (FIG. 9A), 100 µg per dose (FIG. 9B), or 50 µg per dose (FIG. 9C) per dose. The mRNA vaccines were formulated with Compound 1 lipids.
Figure 9B:
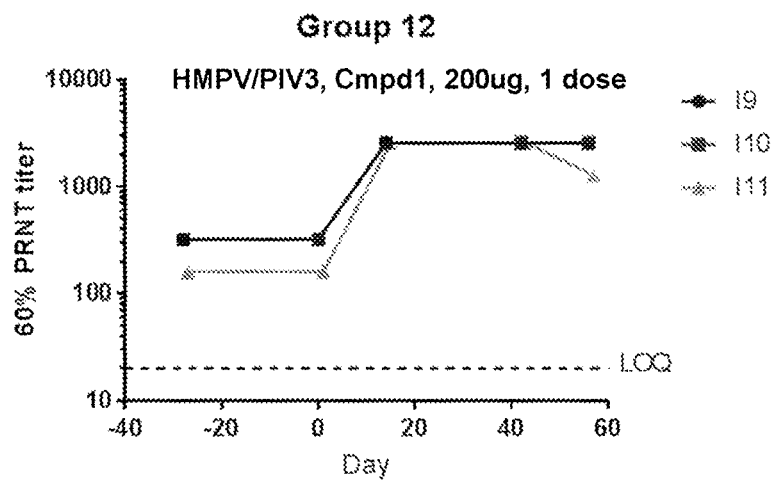
Figure 9C:
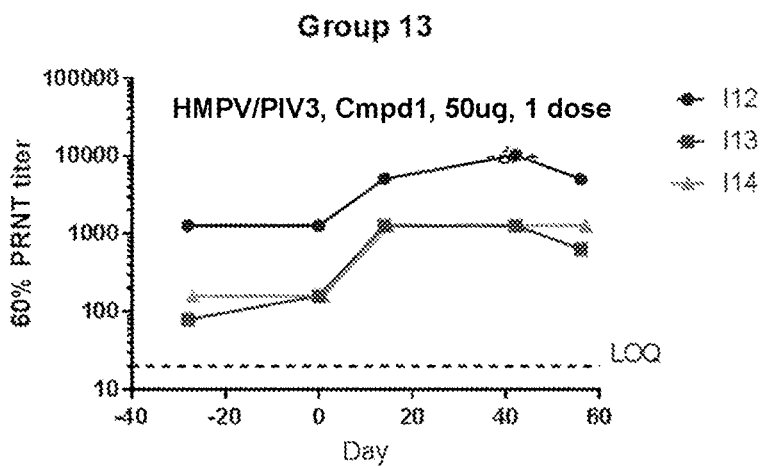
Figure 10A:
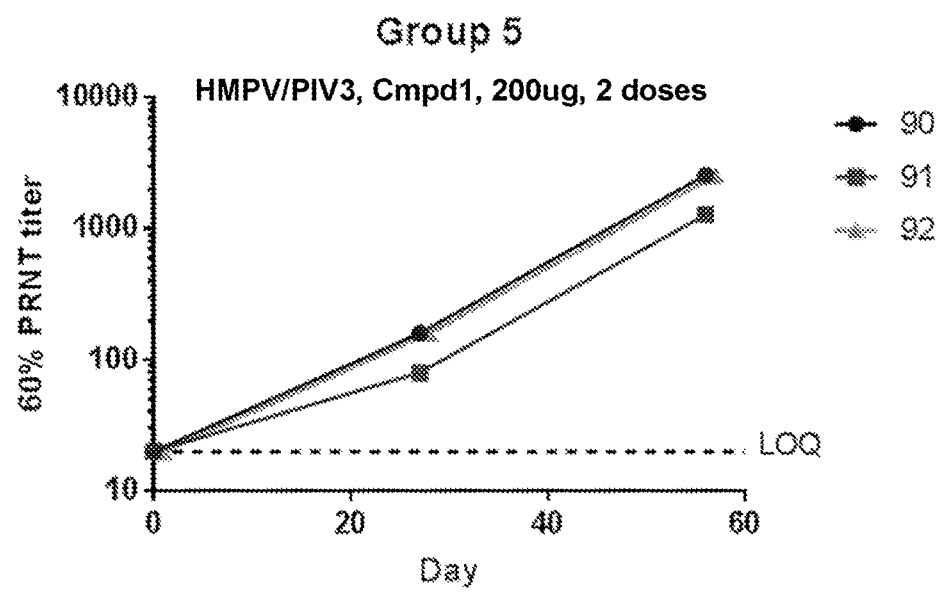
FIGS. 10A-10D are graphs showing the neutralizing antibody titers against hPIV3 in sero-negative African green monkeys immunized with two doses of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) on days 0 and 28 at 200 µg per dose (FIG. 10A), 100 µg per dose (FIG. 10B), 10 µg per dose (FIG. 10C) per dose, or placebo (FIG. 10D). The mRNA vaccines were formulated with Compound 1 lipids.
Figure 10B:
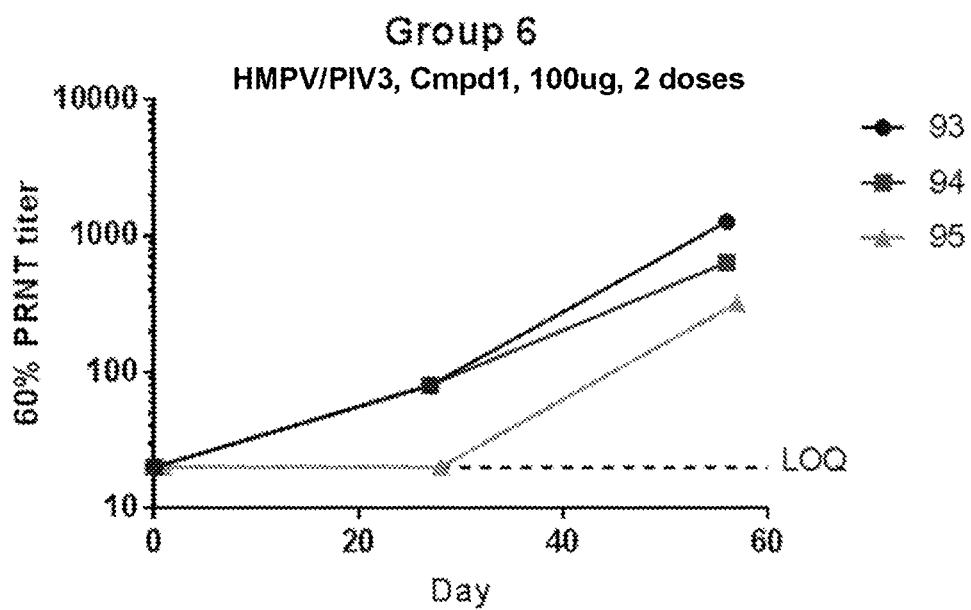
Figure 10C:
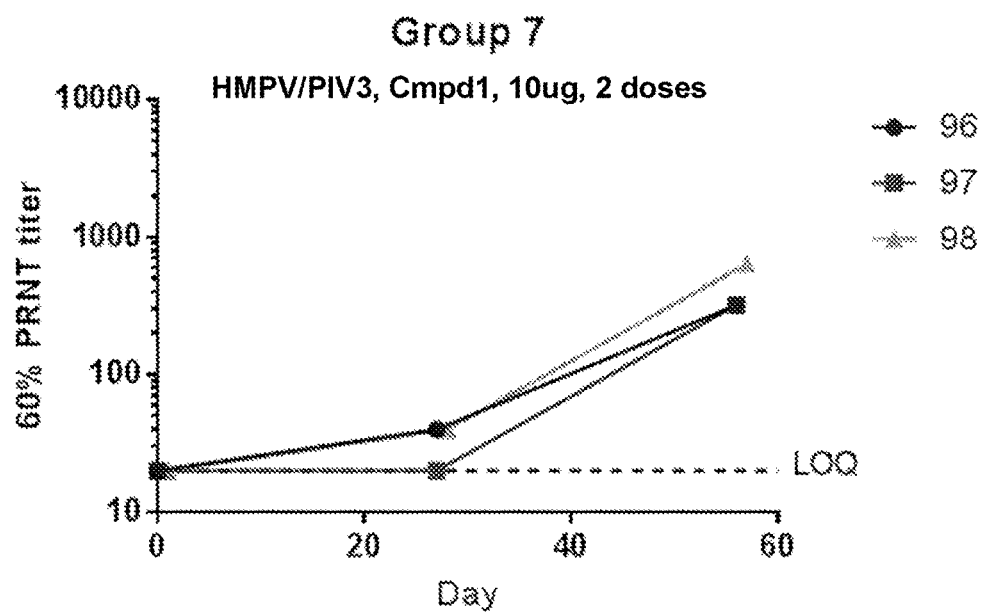
Figure 10D:
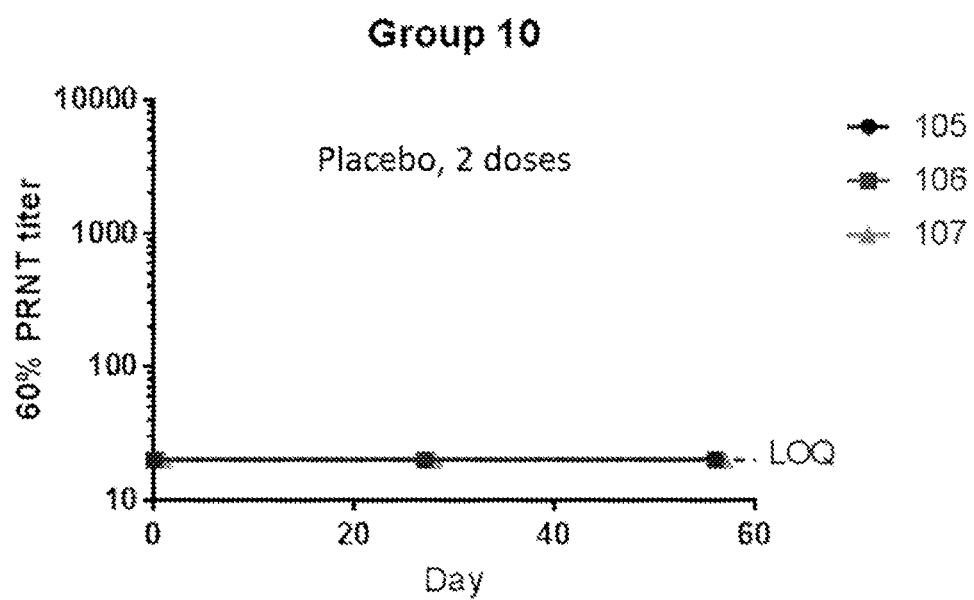
Figure 12A:
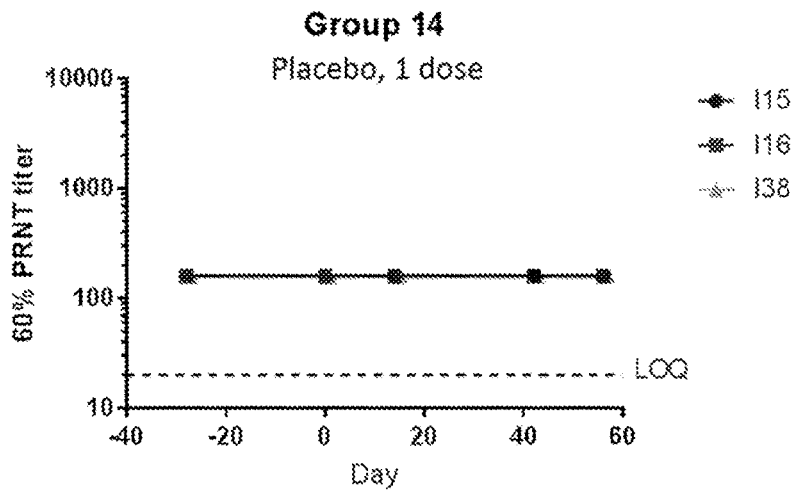
FIGS. 12A-12C are graphs showing the neutralizing antibody titers against hPIV3 in sero-negative African green monkeys immunized with one dose of a vaccine containing (1) mRNA having an open reading frame (SEQ ID NO:4) encoding hMPV F protein (SEQ ID NO:7) and (2) mRNA having an open reading frame (SEQ ID NO:5) encoding hPIV3 F protein (SEQ ID NO:8) on days 0 at 200 µg per dose (FIG. 12B), 50 µg per dose (FIG. 12C), or placebo (FIG. 12A). The mRNA vaccines were formulated with Compound 1 lipids.
Figure 12B:
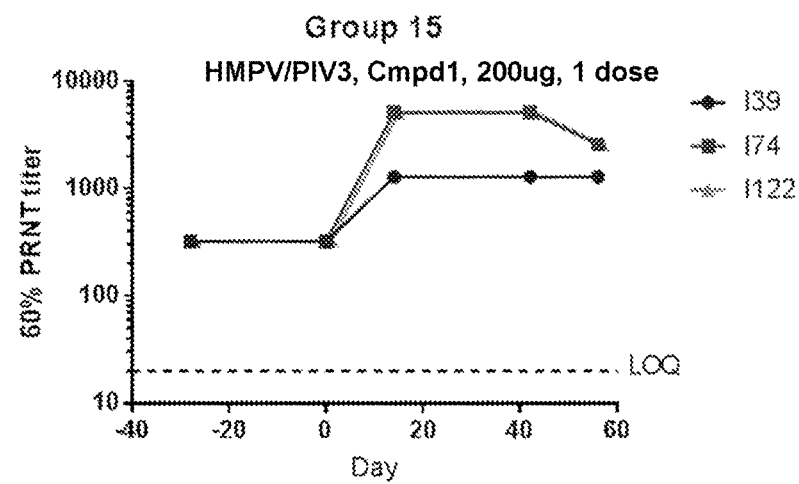
Figure 12C:
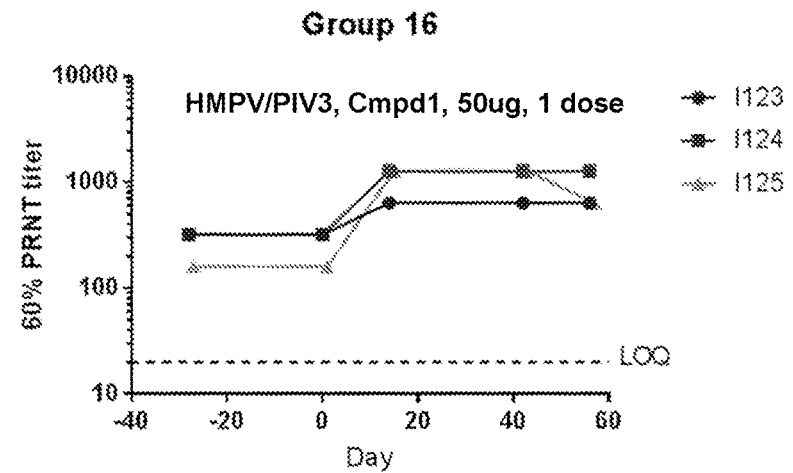
Figure 13A:
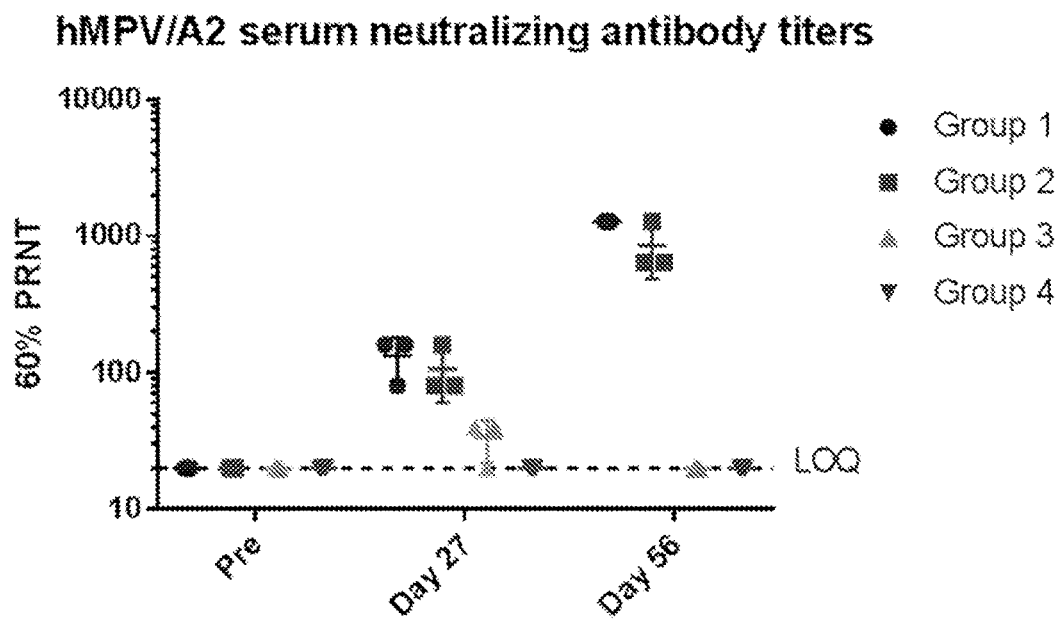
FIGS. 13A-13B are graphs showing the neutralizing antibodies against hMPV/A2 in sero-negative African green monkeys or sero-positive African green monkeys.
Figure 14A:
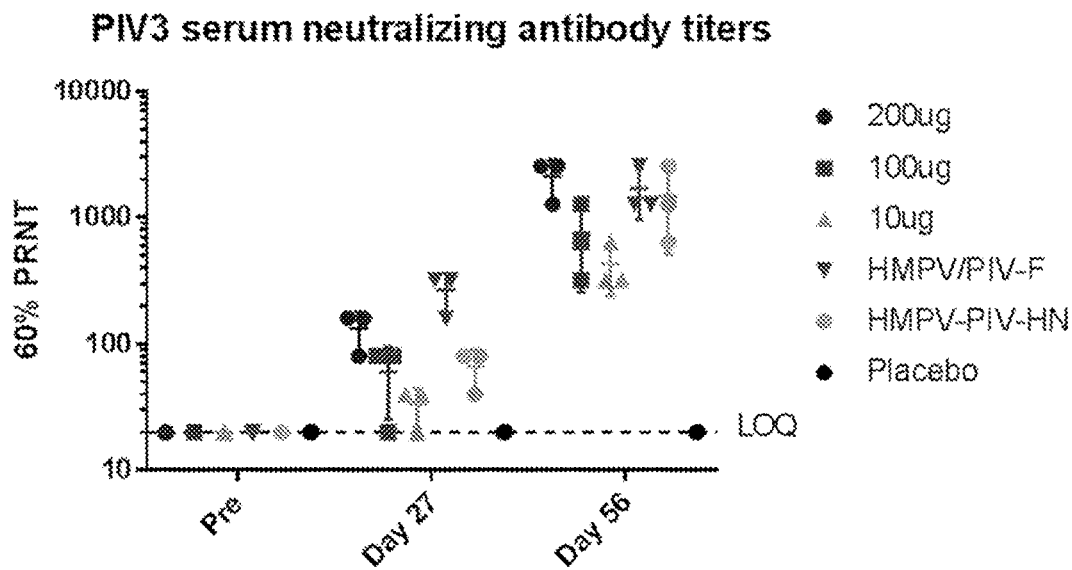
FIGS. 14A-14B are graphs showing the neutralizing antibodies against hPIV3 in sero-negative African green monkeys (AGMs) or sero-positive African green monkeys.

Sero-negative African green monkeys were completely protected from hMPV and hPIV3 infection after two doses of the hMPV/HPIV3 mRNA vaccine (FIGS. 7A-7B). Serum neutralizing antibody titers induced by the hMPV/HPIV3 mRNA vaccines in African green monkeys were analyzed. The results show that in sero-negative African green monkeys, two doses of 200 μg or 100 μg mRNA vaccine induced high levels of neutralizing antibody titers against hMPV (FIGS. 8A and 8B, and FIG. 13A), while two doses of 10μ mRNA vaccine induced lower levels of neutralizing antibody titers against hMPV (FIG. 8C). In hMPV sero-positive African green monkeys, one dose of 200 μg or 50 μg mRNA vaccine induced high levels of neutralizing antibody titers against hMPV (FIGS. 9B and 9C), while the placebo did not induce neutralizing antibodies (FIG. 9A). Similarly, in sero-negative African green monkeys, two doses of 200 μg, 100 μg, or 10 μg mRNA vaccine induced high levels of neutralizing antibody titers against hPIV3 (FIGS. 10A-10C, and FIG. 11A). In hPIV3 sero-positive African green monkeys, one dose of 200 μg or 50 μg mRNA vaccine induced high levels of neutralizing antibody titers against hPIV3 (FIGS. 12B and 12C), while the placebo did not induce neutralizing antibodies (FIG. 12A). Further, mRNA vaccines encoding hPIV3 F protein induced neutralizing antibody titers that is 3-fold higher than that of mRNA vaccines encoding hPIV3 HN protein at the same dosage (FIGS. 11A-11B). However, at day 56 post immunization, neutralizing antibody titer induced by hPIV3 F protein or HN protein became comparable (FIG. 14A). hPIV3 mRNA vaccine alone induced comparable neutralizing antibody titers as the hMPV/HPIV3 mRNA vaccine, indicating that hPIV3 F protein alone is sufficient to generate strong protective response against hPIV3.

Figure 13B:
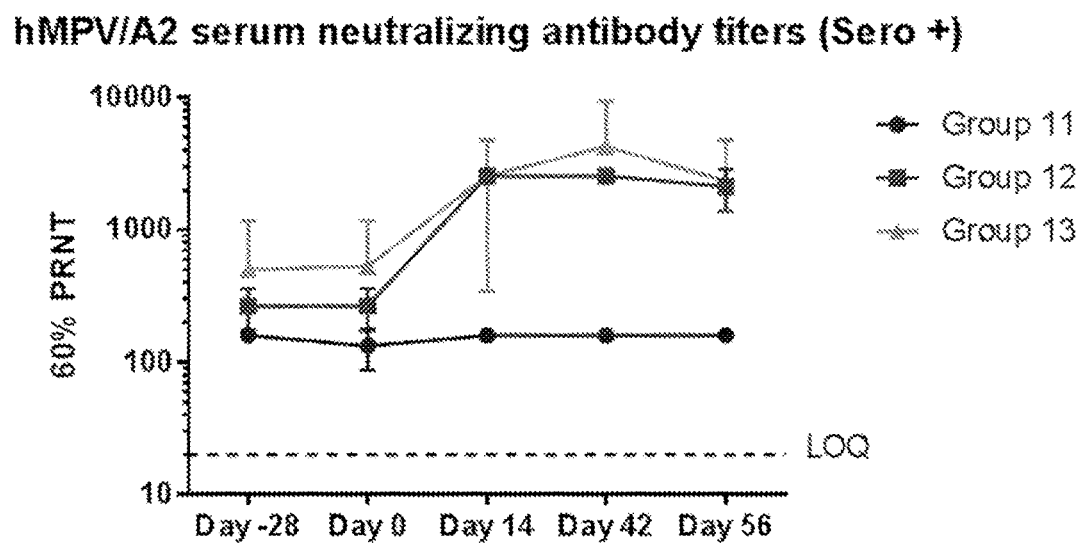
Figure 14B:
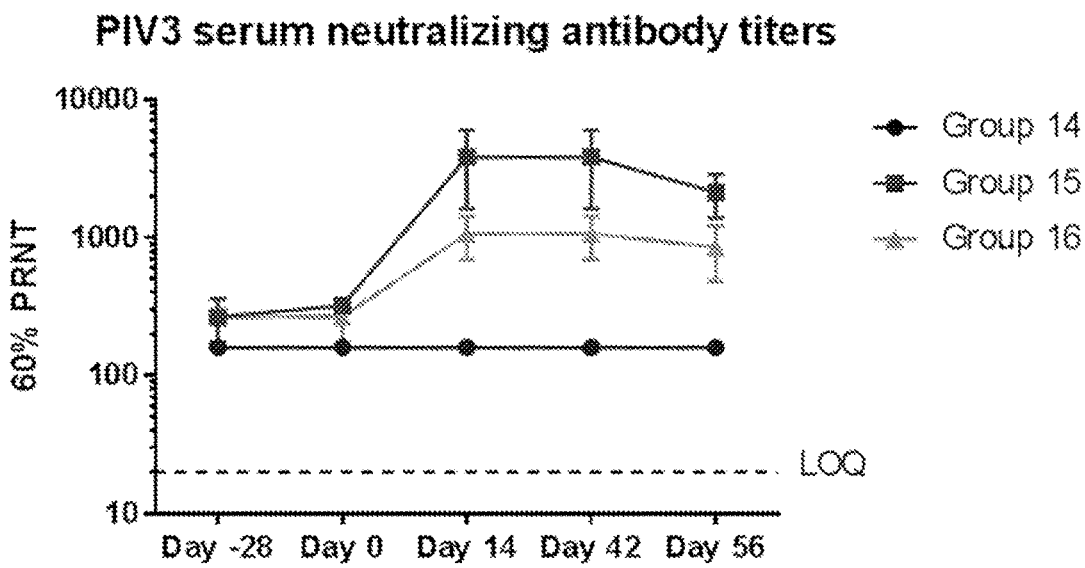

For sero-positive African green monkeys, a single dose of hMPV/HPIV3 mRNA vaccine was able to boost neutralizing antibody titers against hMPV by 8-10 fold (FIG. 13B), and against hPIV3 by 4-10 fold (FIG. 14B) 42 days post immunization.

TABLE 4

African Green Monkey Challenge Study Design

| | G | n | Vaccine | Dose | Formulation | Vaccine | Challenge (Day 57) | Endpoint | |
|---|---|---|---|---|---|---|---|---|---|
| hMPV sero-positive | 1 | 3 | hMPV/PIV | 100/100 | Compound 1 | D 0, D 28 | hMPV | Neutralizing and total IgG titer: Prebleeds, Day 27, Day 56 | Nose and Trachea viral titer by RT-PCR |
| | 2 | 3 | hMPV/PIV | 50/50 | Compound 1 | D 0, D 28 | | | |
| | 3 | 3 | hMPV/PIV | 5/5 | Compound 1 | D 0, D 28 | | | |
| PIV3 sero-positive | 4 | 3 | PBS | NA | NA | D 0, D 28 | | | |
| | 5 | 3 | hMPV/PIV | 100/100 | Compound 1 | D 0, D 28 | PIV3 | | |
| | 6 | 3 | hMPV/PIV | 50/50 | Compound 1 | D 0, D 28 | | | |
| | 7 | 3 | hMPV/PIV | 5/5 | Compound 1 | D 0, D 28 | | | |
| | 8 | 3 | hMPV/PIV-F | 50/50 | Compound 1 | D 0, D 28 | | | |
| | 9 | 3 | hMPV/PIV-HN | 50/50 | SM012 | D 0, D 28 | | | |
| | 10 | 3 | PBS | NA | NA | D 0, D 28 | | | |
| | 11 | 3 | PBS | NA | NA | D 0 | | Neutralizing antibody titers: Day 28, 0, 14, 42, 56 | |
| | 12 | 3 | hMPV/PIV | 100/100 | Compound 1 | D 0 | | | |
| | 13 | 3 | hMPV/PIV | 25/25 | Compound 1 | D 0 | | | |
| | 14 | 3 | PBS | NA | NA | D 0 | | | |
| | 15 | 3 | hMPV/PIV | 100/100 | Compound 1 | D 0 | | | |
| | 16 | 3 | hMPV/PIV | 25/25 | Compound 1 | D 0 | | | |

Example 16

Immunogenicity of hMPV/hPIV3 mRNA Vaccines in African Green Monkeys

Lipid nanoparticle (LNP)—formulated combination of mRNA encoding the following antigens:
hMPV Fusion (F) protein(Strain: A/TN92-4) (SEQ ID NO: 4)
PIV3 F protein (strain: PER/FLA4815/2008) (SEQ ID NO: 5)
PIV3 hemagglutinin-neuraminidase (HN) protein (Strain: 612507167) (SEQ ID NO: 6)

The mRNAs were formulated in a mixture of 4 lipids, including Compound 1; 1,2-dimyristoyl-sn-glycerol, methoxypolyethyleneglycol (PEG2000-DMG); 1,2-distearoyl-sn-glycero-3-phosphocholine (DSPC); and cholesterol.

The immunogenicity of the LNP-formulated hMPV/PIV3-F/PIV3-HN mRNA vaccine was evaluated in African Green Monkeys that had been experimentally infected with hMPV or PIV3 previously, and therefore had serum hMPV or PIV3 neutralizing antibody titers prior to vaccination. African green monkeys previously exposed to hMPV or PIV3 provide a model of immune memory recall responses to vaccination that is intended to mimic the responses that can be anticipated in seropositive human adults. Groups of three hMPV-exposed (Groups 11-13) or PIV3-exposed (Groups 14-16) AGM were immunized intramuscularly (IM) a single time on Day 0 with different dose levels of the hMPV-F/PIV3-F/PIV3-HN vaccine or with a phosphate-buffered saline (PBS) control, as indicated in Table 5. The results in previous Example 15 show that PIV3-HN contributes minimally to the PIV3 neutralizing antibody response. Serum was collected 28 days before immunization (Day −28), the day of immunization (Day 0), and 14, 42, and 56 days after immunization. Serum neutralizing antibody titers to hMPV (Groups 11-13) or PIV3 (Groups 14-16) were measured by 60% plaque reduction neutralization test (PRNT).

TABLE 5

| Group | n | previous infection | Vaccine | mRNA dose (μg) | | | | Vaccine Schedule |
|---|---|---|---|---|---|---|---|---|
| | | | | total | hMPV-F | PIV-F | PIV3-HN | |
| 11 | 3 | hMPV | PBS | NA | NA | NA | NA | Day 0 |
| 12 | 3 | hMPV | hMPV-F/PIV3-F/PIV3-HN | 200 | 100 | 50 | 50 | Day 0 |
| 13 | 3 | hMPV | hMPV-F/PIV3-F/PIV3-HN | 50 | 25 | 12.5 | 12.5 | Day 0 |
| 14 | 3 | PIV3 | PBS | NA | NA | NA | NA | Day 0 |
| 15 | 3 | PIV3 | hMPV-F/PIV3-F/PIV3-HN | 200 | 100 | 50 | 50 | Day 0 |
| 16 | 3 | PIV3 | hMPV-F/PIV3-F/PIV3-HN | 50 | 25 | 12.5 | 12.5 | Day 0 |

NA—not applicable hMPV Neutralizing Antibody Assay

Heat inactivated sera samples are diluted 1:10 and serially diluted further 1:4. Diluted serum samples are incubated with hMPV/A2 (25-50 plaque forming units (pfu)) for 1 hour at room temperature and inoculated in duplicates onto confluent MK-2 monolayers in 24-well plates. After one hour incubation at 37° C. in a 5% $CO_2$ incubator, the wells are overlaid with 0.75% Methylcellulose medium. After 7 days of incubation, the overlays are removed and washed once in PBS. The cells are fixed in cold acetone/methanol solution for one hour and air dried for immuno-staining. The cells are permeabilized in 0.4% Triton-X solution and incubated in blocking solution (10% bovine serum albumin). Mouse anti-hMPV nucleoprotein (N) at a 1:1,000 dilution is added to each well, followed by horseradish peroxidase (HRP) conjugated rabbit anti-mouse IgG diluted at 1:5,000. AEC chromogen detection solution is used for coloration after two hours of incubation or until red plaques are visible. Plaques are counted and virus titers are expressed as plaque forming units. The corresponding reciprocal neutralizing antibody titers are determined at the 60% reduction endpoint of the virus control using a statistics program. Neutralizing titers are reported as mean+/−SD of log 2 transformed titers for all animals in a group at a given time point.

PIV3 Neutralizing Antibody Assay

Figure 15A:
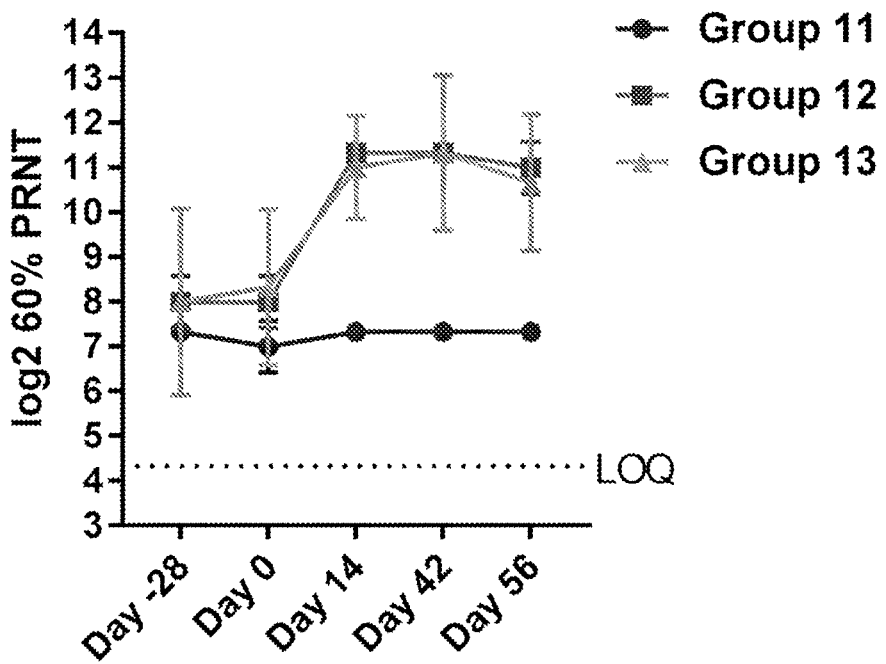
FIGS. 15A-15B are graphs showing the neutralizing antibody titers to hMPV (FIG. 15A) and hPIV3 (FIG. 15B). hMPV or PIV3 neutralizing antibody titers could be detected in all previously-exposed AGM (Groups 11-13 for hMPV and Groups 14-16 for PIV3) and were stable for the 4 weeks preceding immunization. In all cases the peak neutralizing antibody response was reached by 14 days post immunization, and was generally stable for the subsequent 42 days.
Figure 15B:
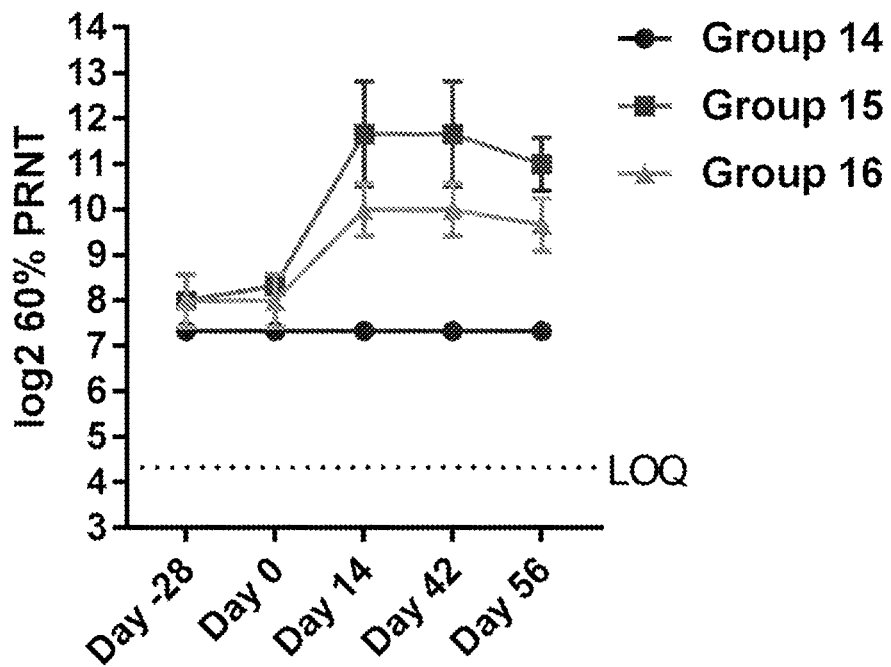

Heat inactivated sera samples are diluted 1:10 with EMEM and serially diluted further 1:4. Diluted serum samples are incubated with PIV3 (25-50 pfu) for 1 hour at room temperature and inoculated in duplicates onto confluent MA-104 monolayers in 24-well plates. After two-hour incubation at 37° C. in a 5% $CO_2$ incubator, the wells are overlaid with 0.75% Methylcellulose medium. After 4 days of incubation, the overlays are removed and the cells are fixed and stained with 0.1% crystal violet for one hour and then rinsed and air dried. The corresponding reciprocal neutralizing antibody titers are determined at the 60% reduction end-point of the virus control using a statistics program. Neutralizing titers are reported as mean+/−SD of log 2 transformed titers for all animals in a group at a given time point.

hMPV or PIV3 neutralizing antibody titers could be detected in all previously-exposed AGM (Groups 11-13 for hMPV and Groups 14-16 for PIV3) and were stable for the 4 weeks preceding immunization (FIGS. 15A-15B). A single 200 µg dose of the hMPV-F/PIV3-F/PIV3-HN mRNA vaccine boosted neutralizing antibody titers to both hMPV (Group 12) and PIV3 (Group 15) by approximately 10 fold. A single 50 µg dose boosted neutralizing antibody titers to hMPV by approximately 8-fold (Groups 13) and to PIV3 by approximately 4-fold (Group 16). In all cases the peak neutralizing antibody response was reached by 14 days post immunization, and was generally stable for the subsequent 42 days.

These data show that the hMPV/PIV3 combination vaccine is a potent booster of neutralizing antibodies primed by hMPV or PIV3 infection in African Green Monkeys.

Example 17

Immunogenicity and Efficacy of hMPV/PIV3 mRNA Vaccines in African Green Monkeys Lipid nanoparticle (LNP)-formulated combinations of mRNA encoding the following antigens:
hMPV Fusion (F) protein (Strain: A/TN92-4) (SEQ ID NO: 4)
PIV3 F protein (strain: PER/FLA4815/2008) (SEQ ID NO: 5)
PIV3 hemagglutinin-neuraminidase (HN) protein (Strain: 612507167) (SEQ ID NO: 6)
The mRNAs were formulated in a mixture of 4 lipids, including Compound 1; 1,2-dimyristoyl-sn-glycerol, methoxypolyethyleneglycol (PEG2000-DMG); 1,2-distearoyl-sn-glycero-3-phosphocholine (DSPC); and cholesterol.

The combination vaccine consists of hMPV-F and PIV3-F mRNA co-formulated at a 1:1 mass ratio in LNP.

The immunogenicity and efficacy of hMPV/PIV3 mRNA vaccines was evaluated in the African Green Monkey models of hMPV or PIV3 challenge. Groups of three African Green Monkeys were immunized with different dose levels of LNP-formulated mRNAs encoding hMPV-F, PIV3-F, and/or PIV3 HN as indicated in Table 6. Control groups were inoculated with phosphate-buffered saline (PBS). All animals were immunized intramuscularly (IM) on Days 0 and 28. Serum was collected before the first immunization and on Days 27 and 56 for measurement of neutralizing antibody titers to hMPV (Groups 1-4) or PIV3 (Groups 5-10) by 60% plaque reduction neutralization test (PRNT). Animals in groups 1-4 were inoculated intratracheally on Day 57 with $5 \times 10^5$ plaque-forming units (pfu) of hMPV strain NL/1/00(A1) and viral load was determined by plaque assay on nose and lung samples collected on Day 61 (4 days post challenge). Animals in groups 5-10 were inoculated intra-nasally and intratracheally on Day 57 with $1 \times 10^6$ pfu of PIV3 strain JS and viral load was determined by plaque assay on nose and lung samples collected on Day 60 (3 days post challenge).

TABLE 6

| | | | mRNA dose (µg) | | | | Vaccine | Challenge |
|---|---|---|---|---|---|---|---|---|
| Group | n | Vaccine | total | hMPV-F | PIV3-F | PIV3-HN | Schedule | (Day 57) |
| 1 | 3 | hMPV-F/PIV3-F/PIV3-HN | 200 | 100 | 50 | 50 | Day 0 & 28 | hMPV |
| 2 | 3 | hMPV-F/PIV3-F/PIV3-HN | 100 | 50 | 25 | 25 | Day 0 & 28 | hMPV |
| 3 | 3 | hMPV-F/PIV3-F/PIV3-HN | 10 | 5 | 2.5 | 2.5 | Day 0 & 28 | hMPV |
| 4 | 3 | PBS | NA | NA | NA | NA | Day 0 & 28 | hMPV |
| 5 | 3 | hMPV-F/PIV3-F/PIV3-HN | 200 | 100 | 50 | 50 | Day 0 & 28 | PIV3 |
| 6 | 3 | hMPV-F/PIV3-F/PIV3-HN | 100 | 50 | 25 | 25 | Day 0 & 28 | PIV3 |
| 7 | 3 | hMPV-F/PIV3-F/PIV3-HN | 10 | 5 | 2.5 | 2.5 | Day 0 & 28 | PIV3 |
| 8 | 3 | hMPV-F/PIV3-F | 100 | 50 | 50 | 0 | Day 0 & 28 | PIV3 |
| 9 | 3 | hMPV-F/PIV3-HN | 100 | 50 | 0 | 50 | Day 0 & 28 | PIV3 |
| 10 | 3 | PBS | NA | NA | NA | NA | Day 0 & 28 | PIV3 |

NA—not applicable hMPV Lung and Nose Viral Titration

Lung and nose homogenates are clarified by centrifugation and diluted in EMEM. Confluent MK-2 monolayers are infected in duplicates with diluted homogenates in 24 well plates. After one hour incubation at 37° C. in a 5% $CO_2$ incubator, the wells are overlaid with 0.75% methylcellulose medium. After 7 days of incubation, the overlays are removed and the cells are fixed for one hour and air dried for immune-staining. Upon blocking the wells, mouse anti-hMPV nucoleoprotein (N) at a 1:1000 dilution to each well, followed by horseradish peroxidase (HRP) conjugated goat anti-mouse IgG diluted at 1:1000. TrueBlue peroxidase substrate is added to each well and incubated at room temperature for 10 to 15 minutes. Visible plaques are counted and virus titers are expressed as pfu per gram (g) of tissue. Viral titers are reported as mean±standard deviation (SD) of log 10 transformed values for all animals in a group.

PIV3 Lung and Nose Viral Titration

Lung and nose homogenates are clarified by centrifugation and diluted in EMEM. Confluent MA-104 (monkey kidney cells) monolayers are infected in duplicates with diluted homogenates in 24 well plates. After two hour incubation at 37° C. in a 5% $CO_2$ incubator, the wells are overlaid with 0.75% methylcellulose medium. After 4 days of incubation, the overlays are removed and the cells are fixed and stained with 0.1% crystal violet for one hour and then rinsed and air dried. Plaques are counted and virus titers are expressed as pfu/g of tissue. Viral loads are reported as mean+/−SD of log 10 transformed values for all animals in a group.

hMPV neutralizing Antibody Assay

Heat inactivated sera samples are diluted 1:10 with OptiMEM and serially diluted further 1:4. Diluted serum samples are incubated with hMPV/A2 (25-50 pfu) for 1 hour at room temperature and inoculated in duplicates onto confluent MK-2 monolayers in 24-well plates. After one hour incubation at 37° C. in a 5% $CO_2$ incubator, the wells are overlaid with 0.75% Methylcellulose medium. After 7 days of incubation, the overlays are removed and washed once in PBS. The cells are fixed in cold acetone/methanol solution for one hour and air dried for immuno-staining. The cells are permeablized in 0.4% Triton-X solution and incubated in blocking solution (10% bovine serum albumin). Mouse anti-hMPV N protein at a 1:1,000 dilution is added to each well, followed by HRP conjugated rabbit anti-mouse IgG diluted at 1:5,000. AEC chromogen detection solution is used for coloration after two hours of incubation or until red plaques are visible. Plaques are counted and virus titers are expressed as plaque forming units. The corresponding reciprocal neutralizing antibody titers are determined at the 60% reduction end-point of the virus control using a statistics program "plqrd.manual.entry". Neutralizing titers are reported as mean+/−SD of log 2 transformed titers for all animals in a group at a given time point.

PIV3 Neutralizing Antibody Assay

Heat inactivated sera samples are diluted 1:10 with EMEM and serially diluted further 1:4. Diluted serum samples are incubated with PIV3 (25-50 pfu) for 1 hour at room temperature and inoculated in duplicates onto confluent MA-104 monolayers in 24 well plates. After two hour incubation at 37° C. in a 5% $CO_2$ incubator, the wells are overlaid with 0.75% Methylcellulose medium. After 4 days of incubation, the overlays are removed and the cells are fixed and stained with 0.1% crystal violet for one hour and then rinsed and air dried. The corresponding reciprocal neutralizing antibody titers are determined at the 60% reduction end-point of the virus control using a statistics program. Neutralizing titers are reported as mean+/−SD of log 2 transformed titers for all animals in a group at a given time point.

Figure 16A:
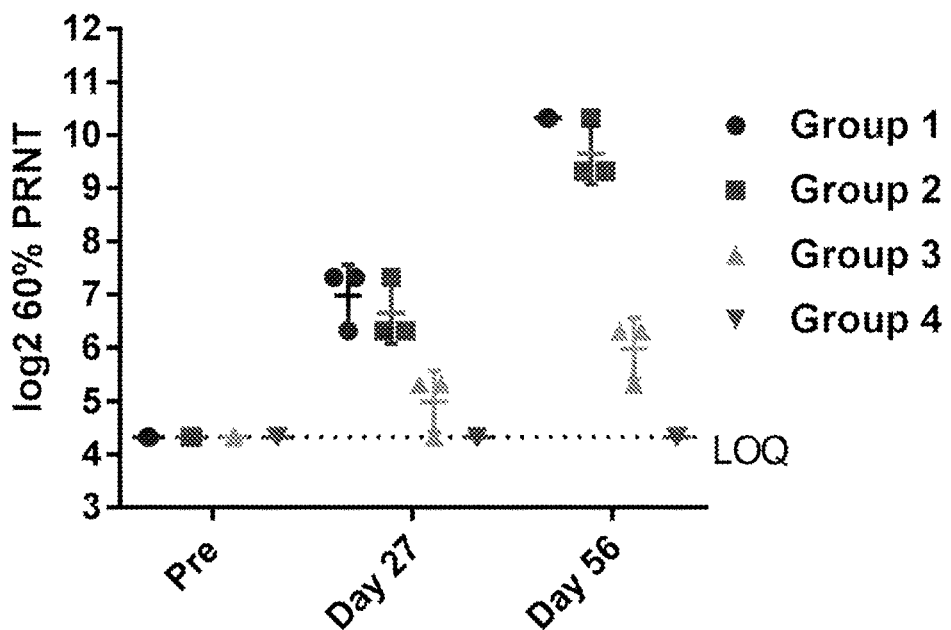
FIGS. 16A-16B are graphs showing the neutralizing antibody titers to hMPV (FIG. 16A) and hPIV3 (FIG. 16B) in AGM. hMPV neutralizing antibodies were detected in serum of the majority of animals 28 days after the first immunization with the hMPV-F/PIV3-F/PIV3-HN mRNA vaccine, and titers were boosted by the second immunization. PIV3 neutralizing antibodies were detected in serum of the majority of animals 28 days after the first immunization with the hMPV/PIV3 mRNA vaccines, and titers were boosted by the second immunization.
Figure 16B:
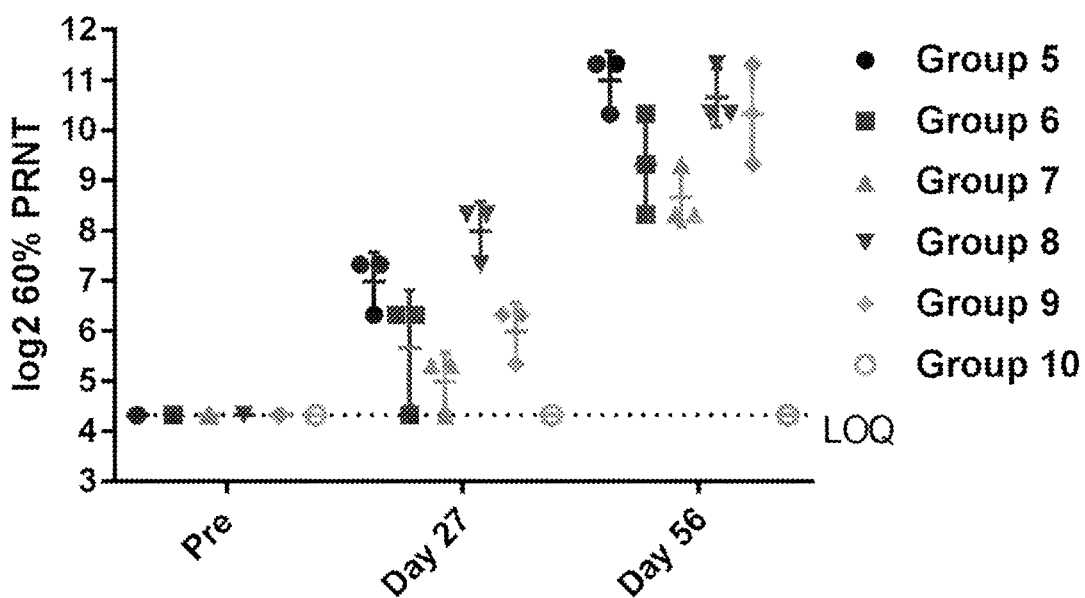

Results hMPV neutralizing antibodies were detected in serum of the majority of animals 28 days after the first immunization with the hMPV-F/PIV3-F/PIV3-HN mRNA vaccine, and titers were boosted by the second immunization (FIG. 16A). The magnitude of the responses were quite high in animals dosed with 200 or 100 µg mRNA (Groups 1 and 2; containing 100 and 50 µg of hMPV-F mRNA, respectively), but was significantly lower in animals dosed with 10 µg mRNA (Group 3; containing 5 µg of hMPV-F mRNA). PIV3 neutralizing antibodies were detected in serum of the majority of animals 28 days after the first immunization with the hMPV/PIV3 mRNA vaccines, and titers were boosted by the second immunization (FIG. 16B). The magnitude of the responses were quite high in all groups, although dose dependent (Groups 5-7). The response induced by the PIV3-F mRNA was equivalent or greater to the response induced by the PIV3-HN mRNA (Group 8 vs. Group 9), and adding PIV3-HN to PIV-F did not enhance PIV3 neutralizing antibody titers (Group 8 vs. Group 5).

Figure 17A:
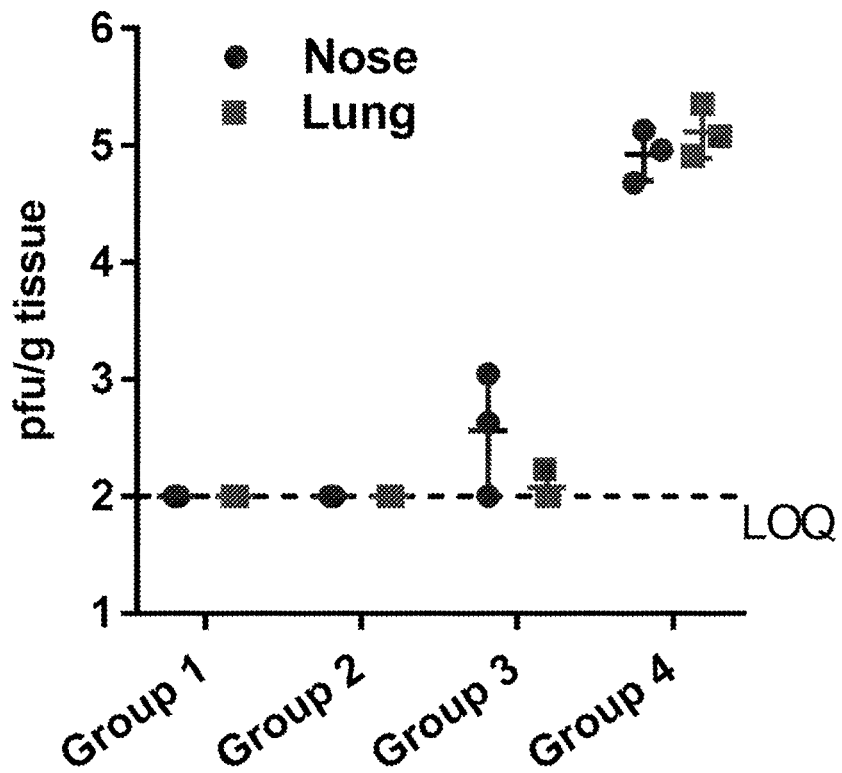
FIGS. 17A-17B are graphs showing viral load after hMPV (FIG. 17A) or hPIV3 (FIG. 17B) challenge of AGM. The hMPV/PIV3 combination vaccine affords full protection against both viruses in the lung and the nose.
Figure 17B:
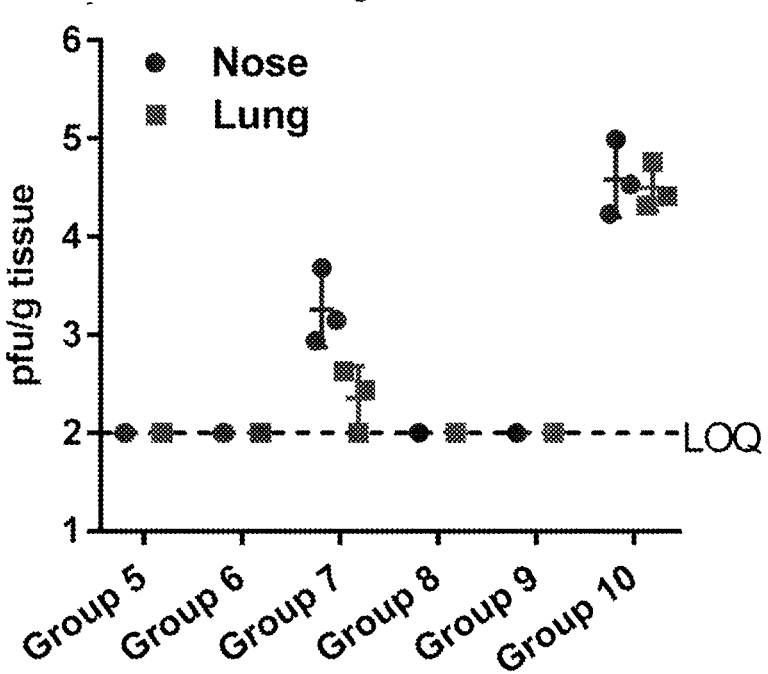

The ability of the hMPV/PIV3 mRNA vaccines to protect African Green Monkeys against challenge was determined by measuring viral load in lungs and noses from immunized animals 4 days after hMPV intratracheal inoculation (Groups 1-4) or 3 days after PIV3 intratracheal and intranasal inoculation (Groups 5-10) (FIGS. 17A-17B). High levels of both viruses were detected in PBS control animals (Groups 4 and 10), but were below the limit of quantification in animals immunized with 100 µg or greater mRNA (Groups 1, 2, 5, 6, 8 and 9), demonstrating that the hMPV/PIV3 combination vaccine affords full protection against both viruses in the lung and the nose. The 10 µg low dose vaccine (Groups 3 and 7) afforded some, but not complete protection against hMPV and PIV3. The animals immunized with the hMPV-F/PIV3-F vaccine (Group 8, which does not include PIV3-HN) were also protected from PIV3 challenge, demonstrating that the immune response to the PIV3-F protein is sufficient for protection against PIV3.

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a polyA tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:
(SEQ ID NO: 12)
GGGAAAUAAGAGAGAAAAGAAGAGUAAGAAGAAAUAUAAGAGCCACC

3' UTR:
(SEQ ID NO: 13)
UGAUAAUAGGCUGGAGCCUCGGUGGCCAUGCUUCUUGCCCCUUGGGCCUC
CCCCCAGCCCCUCCUCCCCUUCCUGCACCCGUACCCCCGUGGUCUUUGAA
UAAAGUCUGAGUGGGCGGC

TABLE 7

Sequences of Antigens encoded by hMPV/HPIV3 mRNA vaccines hMPV F protein

SEQ ID NO: 14 consists of from 5' end to 3' end, 5' UTR SEQ ID NO: 12, mRNA ORF SEQ ID NO: 4, and 3' UTR SEQ ID NO: 13.   14

| | | |
|---|---|---|
| Chemistry | 1-methylpseudouridine | |
| Cap | 7 mG(5')ppp(5')NlmpNp | |
| 5' UTR | GGGAAAUAAGAGAGAAAAGAAGAGUAAGAAGAAAUAUAAGAGCCACC | 12 |

TABLE 7-continued

Sequences of Antigens encoded by hMPV/HPIV3 mRNA vaccines

| | | |
|---|---|---|
| ORF of DNA Construct | ATGAGCTGGAAGGTGGTGATTATCTTCAGCCTGCTGATTAC<br>ACCTCAACACGGCCTGAAGGAGAGCTACCTGGAAGAGAGC<br>TGCTCCACCATCACCGAGGGCTACCTGAGCGTGCTGCGGAC<br>CGGCTGGTACACCAACGTGTTCACCCTGGAGGTGGGCGAC<br>GTGGAGAACCTGACCTGCAGCGACGGCCCTAGCCTGATCA<br>AGACCGAGCTGGACCTGACCAAGAGCGCTCTGAGAGAGCT<br>GAAGACCGTGTCCGCCGACCAGCTGGCCAGAGAGGAACAG<br>ATCGAGAACCCTCGGCAGAGCAGATTCGTGCTGGGCGCCA<br>TCGCTCTGGGAGTCGCCGCTGCCGCTGCAGTGACAGCTGGA<br>GTGGCCATTGCTAAGACCATCAGACTGGAAAGCGAGGTGA<br>CAGCCATCAACAATGCCCTGAAGAAGACCAACGAGGCCGT<br>GAGCACCCTGGGCAATGGAGTGAGAGTGCTGGCCACAGCC<br>GTGGCGGGAGCTGAAGGACTTCGTGAGCAAGAACCTGACCA<br>GAGCCATCAACAAGAACAAGTGCGACATCGATGACCTGAA<br>GATGGCCGTGAGCTTCTCCCAGTTCAACAGACGGTTCCTGA<br>ACGTGGTGAGACAGTTCTCCGACAACGCTGGAATCACACCT<br>GCCATTAGCCTGGACCTGATGACCGACGCCGAGCTGGCTA<br>GAGCCGTGCCCAACATGCCCACCAGCGCTGGCCAGATCAA<br>GCTGATGCTGGAGAACAGAGCCATGGTGCGGAGAAAGGGC<br>TTCGGCATCCTGATTGGGGTGTATGGAAGCTCCGTGATCTA<br>CATGGTGCAGCTGCCCATCTTCGGCGTGATCGACACACCCT<br>GCTGGATCGTGAAGGCCGCTCCTAGCTGCTCCGAGAAGAA<br>AGGAAACTATGCCTGTCTGCTGAGAGAGGACCAGGGCTGG<br>TACTGCCAGAACGCCGGAAGCACAGTGTACTATCCCAACG<br>AGAAGGACTGCGAGACCAGAGGCGACCACGTGTTCTGCGA<br>CACCGCTGCCGGAATCAACGTGGCCGAGCAGAGCAAGGAG<br>TGCAACATCAACATCAGCACAACCAACTACCCCTGCAAGG<br>TGAGCACCGGACGGCACCCCATCAGCATGGTGGCTCTGAG<br>CCCTCTGGGCGCTCTGGTGGCCTGCTATAAGGGCGTGTCCT<br>GTAGCATCGGCAGCAATCGGGTGGGCATCATCAAGCAGCT<br>GAACAAGGGATGCTCCTACATCACCAACCAGGACGCCGAC<br>ACCGTGACCATCGACAACACCGTGTACCAGCTGAGCAAGG<br>TGGAGGGCGAGCAGCACGTGATCAAGGGCAGACCCGTGAG<br>CTCCAGCTTCGACCCCATCAAGTTCCCTGAGGACCAGTTCA<br>ACGTGGCCCTGGACCAGGTGTTTGAGAACATCGAGAACAG<br>CCAGGCCCTGGTGGACCAGAGCAACAGAATCCTGTCCAGC<br>GCTGAGAAGGGCAACACCGGCTTCATCATTGTGATCATTCT<br>GATCGCCGTGCTGGGCAGCTCCATGATCCTGGTGAGCATCT<br>TCATCATTATCAAGAAGACCAAGAAACCCACCGGAGCCCC<br>TCCTGAGCTGAGCGGCGTGACCAACAATGGCTTCATTCCCC<br>ACAACTGA | 1 |
| ORF of mRNA Construct | AUGAGCUGGAAGGUGGUGAUUAUCUUCAGCCUGCUGAUU<br>ACACCUCAACACGGCCUGAAGGAGAGCUACCUGGAAGAG<br>AGCUGCUCCACCAUCACCGAGGGCUACCUGAGCGUGCUGC<br>GGACCGGCUGGUACACCAACGUGUUCACCCUGGAGGUGG<br>GCGACGUGGAGAACCUGACCUGCAGCGACGGCCCUAGCC<br>UGAUCAAGACCGAGCUGGACCUGACCAAGAGCGCUCUGA<br>GAGAGCUGAAGACCGUGUCCGCCGACCAGCUGGCCAGAG<br>AGGAACAGAUCGAGAACCCUCGGCAGAGCAGAUUCGUGC<br>UGGGCGCCAUCGCUCUGGGAGUCGCCGCUGCCGCUGCAG<br>UGACAGCUGGAGUGGCCAUUGCUAAGACCAUCAGACUGG<br>AAAGCGAGGUGACAGCCAUCAACAAUGCCCUGAAGAAGA<br>CCAACGAGGCCGUGAGCACCCUGGGCAAUGGAGUGAGAG<br>UGCUGGCCACAGCCGUGCGGGAGCUGAAGGACUUCGUGA<br>GCAAGAACCUGACCAGAGCCAUCAACAAGAACAAGUGCG<br>ACAUCGAUGACCUGAAGAUGGCCGUGAGCUUCUCCCAGU<br>UCAACAGACGGUUCCUGAACGUGGUGAGACAGUUCUCCG<br>ACAACGCUGGAAUCACACCUGCCAUUAGCCUGGACCUGA<br>UGACCGACGCCGAGCUGGCUAGAGCCGUGCCCAACAUGCC<br>CACCAGCGCUGGCCAGAUCAAGCUGAUGCUGGAGAACAG<br>AGCCAUGGUGCGGAGAAAGGGCUUCGGCAUCCUGAUUGG<br>GGUGUAUGGAAGCUCCGUGAUCUACAUGGUGCAGCUGCC<br>CAUCUUCGGCGUGAUCGACACACCCUGCUGGAUCGUGAA<br>GGCCGCUCCUAGCUGCUCCGAGAAGAAAGGAAACUAUGC<br>CUGUCUGCUGAGAGAGGACCAGGGCUGGUACUGCCAGAA<br>CGCCGGAAGCACAGUGUACUAUCCCAACGAGAAGGACUG<br>CGAGACCAGAGGCGACCACGUGUUCUGCGACACCGCUGCC<br>GGAAUCAACGUGGCCGAGCAGAGCAAGGAGUGCAACAUC<br>AACAUCAGCACAACCAACUACCCCUGCAAGGUGAGCACCG<br>GACGGCACCCCAUCAGCAUGGUGGCUCUGAGCCCUCUGG<br>GCGCUCUGGUGGCCUGCUAUAAGGGCGUGUCCUGUAGCA<br>UCGGCAGCAAUCGGGUGGGCAUCAUCAAGCAGCUGAACA<br>AGGGAUGCUCCUACAUCACCAACCAGGACGCCGACACCGU<br>GACCAUCGACAACACCGUGUACCAGCUGAGCAAGGUGGA<br>GGGCGAGCAGCACGUGAUCAAGGGCAGACCCGUGAGCUC<br>CAGCUUCGACCCCAUCAAGUUCCCUGAGGACCAGUUCAAC | 4 |

TABLE 7-continued

Sequences of Antigens encoded by hMPV/HPIV3 mRNA vaccines

|  |  |  |
|---|---|---|
|  | GUGGCCCUGGACCAGGUGUUUGAGAACAUCGAGAACAGC<br>CAGGCCCUGGUGGACCAGAGCAACAGAAUCCUGUCCAGC<br>GCUGAGAAGGGCAACACCGGCUUCAUCAUUGUGAUCAUU<br>CUGAUCGCCGUGCUGGGCAGCUCCAUGAUCCUGGUGAGC<br>AUCUUCAUCAUUAUCAAGAAGACCAAGAAACCCACCGGA<br>GCCCCUCCUGAGCUGAGCGGCGUGACCAACAAUGGCUUC<br>AUUCCCCACAACUGA |  |
| 3'UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 13 |
| Corresponding<br>amino acid<br>sequence | MSWKVVIIFSLLITPQHGLKESYLEESCSTITEGYLSVLRTGWY<br>TNVFTLEVGDVENLTCSDGPSLIKTELDLTKSALRELKTVSAD<br>QLAREEQIENPRQSRFVLGAIALGVAAAAAVTAGVAIAKTIRL<br>ESEVTAINNALKKTNEAVSTLGNGVRVLATAVRELKDFVSKN<br>LTRAINKNKCDIDDLKMAVSFSQFNRRFLNVVRQFSDNAGITP<br>AISLDLMTDAELARAVPNMPTSAGQIKLMLENRAMVRRKGF<br>GILIGVYGSSVIYMVQLPIFGVIDTPCWIVKAAPSCSEKKGNYA<br>CLLREDQGWYCQNAGSTVYYPNEKDCETRGDHVFCDTAAGI<br>NVAEQSKECNINISTTNYPCKVSTGRHPISMVALSPLGALVAC<br>YKGVSCSIGSNRVGIIKQLNKGCSYITNQDADTVTIDNTVYQL<br>SKVEGEQHVIKGRPVSSSFDPIKFPEDQFNVALDQVFENIENSQ<br>ALVDQSNRILSSAEKGNTGFIIVIILIAVLGSSMILVSIFIIIKKTK<br>KPTGAPPELSGVTNNGFIPHN | 7 |
| PolyA tail | 100 nt |  | hPIV3 F protein

| | | |
|---|---|---|
| SEQ ID NO: 15 consists of from 5' end to 3' end, 5' UTR SEQ ID<br>NO: 12, mRNA ORF SEQ ID NO: 5, and 3' UTR SEQ ID NO: 13. | | 15 |
| Chemistry | 1-methylpseudouridine | |
| Cap | 7 mG(5')ppp(5')N1mpNp | |
| 5' UTR | GGGAAAUAAGAGAGAAAAGAAGAGUAAGAAGAAAUAUA<br>AGAGCCACC | 12 |
| ORF of DNA<br>Construct | ATGCCCATCAGCATCCTGCTGATCATCACCACAATGATCAT<br>GGCCAGCCACTGCCAGATCGACATCACCAAGCTGCAGCAC<br>GTGGGCGTGCTCGTGAACAGCCCCAAGGGCATGAAGATCA<br>GCCAGAACTTCGAGACACGCTACCTGATCCTGAGCCTGATC<br>CCCAAGATCGAGGACAGCAACAGCTGCGGCGACCAGCAGA<br>TCAAGCAGTACAAGCGGCTGCTGGACAGACTGATCATCCC<br>CCTGTACGACGGCCTGCGGCTGCAGAAAGACGTGATCGTG<br>ACCAACCAGGAAAGCAACGAGAACACCGACCCCCGGACCG<br>AGAGATTCTTCGGCGGCGTGATCGGCACAATCGCCCTGGG<br>AGTGGCCACAAGCGCCCAGATTACAGCCGCTGTGGCCCTG<br>GTGGAAGCCAAGCAGGCCAGAAGCGACATCGAGAAGCTGA<br>AAGAGGCCATCCGGGACACCAACAAGGCCGTGCAGAGCGT<br>GCAGTCCAGCGTGGGCAATCTGATCGTGGCCATCAAGTCCG<br>TGCAGGACTACGTGAACAAAGAAATCGTGCCCTCTATCGCC<br>CGGCTGGGCTGTGAAGCTGCCGGACTGCAGCTGGGCATTG<br>CCCTGACACAGCACTACAGCGAGCTGACCAACATCTTCGGC<br>GACAACATCGGCAGCCTGCAGGAAAAGGGCATTAAGCTGC<br>AGGGAATCGCCAGCCTGTACCGCACCAACATCACCGAGAT<br>CTTCACCACCAGCACCGTGGATAAGTACGACATCTACGACC<br>TGCTGTTCACCGAGAGCATCAAAGTGCGCGTGATCGACGTG<br>GACCTGAACGACTACAGCATCACCCTGCAAGTGCGGCTGC<br>CCCTGCTGACCAGACTGCTGAACACCCAGATCTACAAGGTG<br>GACAGCATCTCCTACAACATCCAGAACCGCGAGTGGTACA<br>TCCCTCTGCCCAGCCACATTATGACCAAGGGCGCCTTTCTG<br>GGCGGAGCCGACGTGAAAGAGTGCATCGAGGCCTTCAGCA<br>GCTACATCTGCCCCAGCGACCCTGGCTTCGTGCTGAACCAC<br>GAGATGGAAAGCTGCCTGAGCGGCAACATCAGCCAGTGCC<br>CCAGAACCACCGTGACCTCCGACATCGTGCCCAGATACGCC<br>TTCGTGAATGGCGGCGTGGTGGCCAACTGCATCACCACCAC<br>CTGTACCTGCAACGGCATCGGCAACCGGATCAACCAGCCTC<br>CCGATCAGGGCGTGAAGATTATCACCCACAAAGAGTGTAA<br>CACCATCGGCATCAACGGCATGCTGTTCAATACCAACAAA<br>GAGGGCACCCTGGCCTTCTACACCCCCGACGATATCACCCT<br>GAACAACTCCGTGGCTCTGGACCCCATCGACATCTCCATCG<br>AGCTGAACAAGGCCAAGAGCGACCTGGAAGAGTCCAAAGA<br>GTGGATCCGGCGGAGCAACCAGAAGCTGGACTCTATCGGC<br>AGCTGGCACCAGAGCAGCACCACCATCATCGTGATCCTGAT | 2 |

TABLE 7-continued

| Sequences of Antigens encoded by hMPV/HPIV3 mRNA vaccines | | |
|---|---|---|
| | TATGATGATTATCCTGTTCATCATCAACATTACCATCATCAC<br>TATCGCCATTAAGTACTACCGGATCCAGAAACGGAACCGG<br>GTGGACCAGAATGACAAGCCCTACGTGCTGACAAACAAG | |
| ORF of mRNA Construct | AUGCCCAUCAGCAUCCUGCUGAUCAUCACCACAAUGAUC<br>AUGGCCAGCCACUGCCAGAUCGACAUCACCAAGCUGCAGC<br>ACGUGGGCGUGCUCGUGAACAGCCCCAAGGGCAUGAAGA<br>UCAGCCAGAACUUCGAGACACGCUACCUGAUCCUGAGCC<br>UGAUCCCCAAGAUCGAGGACAGCAACAGCUGCGGCGACC<br>AGCAGAUCAAGCAGUACAAGCGGCUGCUGGACAGACUGA<br>UCAUCCCCCUGUACGACGGCCUGCGGCUGCAGAAAGACG<br>UGAUCGUGACCAACCAGGAAAGCAACGAGAACACCGACC<br>CCCGGACCGAGAGAUUCUUCGGCGGCGUGAUCGGCACAA<br>UCGCCCUGGGAGUGGCCACAAGCGCCCAGAUUACAGCCGC<br>UGUGGCCCUGGUGGAAGCCAAGCAGGCCAGAAGCGACAU<br>CGAGAAGCUGAAAGAGGCCAUCCGGGACACCAACAAGGC<br>CGUGCAGAGCGUGCAGUCCAGCGUGGGCAAUCUGAUCGU<br>GGCCAUCAAGUCCGUGCAGGACUACGUGAACAAAGAAAU<br>CGUGCCCUCUAUCGCCCGGCUGGGCUGUGAAGCUGCCGG<br>ACUGCAGCUGGGCAUUGCCCUGACACAGCACUACAGCGA<br>GCUGACCAACAUCUUCGGCGACAACAUCGGCAGCCUGCA<br>GGAAAAGGGCAUUAAGCUGCAGGGAAUCGCCAGCCUGUA<br>CCGCACCAACAUCACCGAGAUCUUCACCACCAGCACCGUG<br>GAUAAGUACGACAUCUACGACCUGCUGUUCACCGAGAGC<br>AUCAAAGUGCGCGUGAUCGACGUGGACCUGAACGACUAC<br>AGCAUCACCCUGCAAGUGCGGCUGCCCCUGCUGACCAGAC<br>UGCUGAACACCCAGAUCUACAAGGUGGACAGCAUCUCCU<br>ACAACAUCCAGAACCGCGAGUGGUACAUCCCUCUGCCCAG<br>CCACAUUAUGACCAAGGGCGCCUUUCUGGGCGGAGCCGA<br>CGUGAAAGAGUGCAUCGAGGCCUUCAGCAGCUACAUCUG<br>CCCCAGCGACCCUGGCUUCGUGCUGAACCACGAGAUGGA<br>AAGCUGCCUGAGCGGCAACAUCAGCCAGUGCCCCAGAACC<br>ACCGUGACCUCCGACAUCGUGCCCAGAUACGCCUUCGUGA<br>AUGGCGGCGUGGUGGCCAACUGCAUCACCACCACCUGUA<br>CCUGCAACGGCAUCGGCAACCGGAUCAACCAGCCUCCCGA<br>UCAGGGCGUGAAGAUUAUCACCCACAAAGAGUGUAACAC<br>CAUCGGCAUCAACGGCAUGCUGUUCAAUACCAACAAAGA<br>GGGCACCCUGGCCUUCUACACCCCCGACGAUAUCACCCUG<br>AACAACUCCGUGGCUCUGGACCCCAUCGACAUCUCCAUCG<br>AGCUGAACAAGGCCAAGAGCGACCUGGAAGAGUCCAAAG<br>AGUGGAUCCGGCGGAGCAACCAGAAGCUGGACUCUAUCG<br>GCAGCUGGCACCAGAGCAGCACCACCAUCAUCGUGAUCCU<br>GAUUAUGAUGAUUAUCCUGUUCAUCAUCAACAUUACCAU<br>CAUCACUAUCGCCAUUAAGUACUACCGGAUCCAGAAACG<br>GAACCGGGUGGACCAGAAUGACAAGCCCUACGUGCUGAC<br>AAACAAG | 5 |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 13 |
| Corresponding amino acid sequence | MPISILLIITTMIMASHCQIDITKLQHVGVLVNSPKGMKISQNFE<br>TRYLILSLIPKIEDSNSCGDQQIKQYKRLLDRLIIPLYDGLRLQK<br>DVIVTNQESNENTDPRTERFFGGVIGTIALGVATSAQITAAVAL<br>VEAKQARSDIEKLKEAIRDTNKAVQSVQSSVGNLIVAIKSVQD<br>YVNKEIVPSIARLGCEAAGLQLGIALTQHYSELTNIFGDNIGSL<br>QEKGIKLQGIASLYRTNITEIFTTSTVDKYDIYDLLFTESIKVRV<br>IDVDLNDYSITLQVRLPLLTRLLNTQIYKVDSISYNIQNREWYI<br>PLPSHIMTKGAFLGGADVKECIEAFSSYICPSDPGFVLNHEMES<br>CLSGNISQCPRTTVTSDIVPRYAFVNGGVVANCITTTCTCNGIG<br>NRINQPPDQGVKIITHKECNTIGINGMLFNTNKEGTLAFYTPDD<br>ITLNNSVALDPIDISIELNKAKSDLEESKEWIRRSNQKLDSIGSW<br>HQSSTTIIVILIMMIILFIINITIIITIAIKYYRIQKRNRVDQNDKPYV<br>LTNK | 8 |
| PolyA tail | 100 nt | |
| | hPIV3 HN protein | |
| SEQ ID NO: 16 consists of from 5' end to 3' end, 5' UTR SEQ ID NO: 12, mRNA ORF SEQ ID NO: 6, and 3' UTR SEQ ID NO: 13. | | 16 |
| Chemistry | 1-methylpseudouridine | |
| Cap | 7 mG(5')ppp(5')NlmpNp | |
| 5' UTR | GGGAAAUAAGAGAGAAAAGAAGAGUAAGAAGAAAUAUA<br>AGAGCCACC | 12 |

TABLE 7-continued

Sequences of Antigens encoded by hMPV/HPIV3 mRNA vaccines

| ORF of DNA Construct | ATGGAATACTGGAAGCACACCAACCACGGCAAGGACGCCG GCAACGAGCTGGAAACCAGCACAGCCACACACGGCAACAA GCTGACCAACAAGATCACCTACATCCTGTGGACCATCACCC TGGTGCTGCTGAGCATCGTGTTCATCATCGTGCTGACCAAT AGCATCAAGAGCGAGAAGGCCAGAGAGAGCCTGCTGCAGG ACATCAACAACGAGTTCATGGAAGTGACCGAGAAGATCCA GGTGGCCAGCGACAACACCAACGACCTGATCCAGAGCGGC GTGAACACCCGGCTGCTGACCATCCAGAGCCACGTGCAGA ACTACATCCCCATCAGCCTGACCCAGCAGATCAGCGACCTG CGGAAGTTCATCAGCGAGATCACCATCCGGAACGACAACC AGGAAGTGCCCCCCCAGAGAATCACCCACGACGTGGGCAT CAAGCCCCTGAACCCCGACGATTTCTGGCGGTGTACAAGCG GCCTGCCCAGCCTGATGAAGACCCCCAAGATCCGGCTGAT GCCTGGCCCTGGACTGCTGGCCATGCCTACCACAGTGGATG GCTGTGTGCGGACCCCCAGCCTCGTGATCAACGATCTGATC TACGCCTACACCAGCAACCTGATCACCCGGGGCTGCCAGG ATATCGGCAAGAGCTACCAGGTGCTGCAGATCGGCATCAT CACCGTGAACTCCGACCTGGTGCCCGACCTGAACCCTCGGA TCAGCCACACCTTCAACATCAACGACAACAGAAAGAGCTG CAGCCTGGCTCTGCTGAACACCGACGTGTACCAGCTGTGCA GCACCCCCAAGGTGGACGAGAGAAGCGACTACGCCAGCAG CGGCATCGAGGATATCGTGCTGGACATCGTGAACTACGAC GGCAGCATCAGCACCACCCGGTTCAAGAACAACAACATCA GCTTCGACCAGCCCTACGCCGCCCTGTACCCTTCTGTGGGC CCTGGCATCTACTACAAGGGCAAGATCATCTTCCTGGGCTA CGGCGGCCTGGAACACCCCATCAACGAGAACGCCATCTGC AACACCACCGGCTGCCCTGGCAAGACCCAGAGAGACTGCA ATCAGGCCAGCCACAGCCCTGGTTCAGCGACCGCAGAAT GGTCAACTCTATCATCGTGGTGGACAAGGGCCTGAACAGC GTGCCCAAGCTGAAAGTGTGGACAATCAGCATGCGCCAGA ACTACTGGGGCAGCGAGGGCAGACTTCTGCTGCTGGGAAA CAAGATCTACATCTACACCCGGTCCACCAGCTGGCACAGCA AACTGCAGCTGGGAATCATCGACATCACCGACTACAGCGA CATCCGGATCAAGTGGACCTGGCACAACGTGCTGAGCAGA CCCGGCAACAATGAGTGCCCTTGGGGCCACAGCTGCCCCG ATGGATGTATCACCGGCGTGTACACCGACGCCTACCCCCTG AATCCTACCGGCTCCATCGTGTCCAGCGTGATCCTGGACAG CCAGAAAAGCAGAGTGAACCCCGTGATCACATACAGCACC GCCACCGAGAGAGTGAACGAACTGGCCATCAGAAACAAGA CCCTGAGCGCCGGCTACACCACCACAAGCTGCATCACACA CTACAACAAGGGCTACTGCTTCCACATCGTGGAAATCAACC ACAAGTCCCTGAACACCTTCCAGCCCATGCTGTTCAAGACC GAGATCCCCAAGAGCTGCTCC | 3 |
| ORF of mRNA Construct | AUGGAAUACUGGAAGCACACCAACCACGGCAAGGACGCC GGCAACGAGCUGGAAACCAGCACAGCCACACACGGCAAC AAGCUGACCAACAAGAUCACCUACAUCCUGUGGACCAUC ACCCUGGUGCUGCUGAGCAUCGUGUUCAUCAUCGUGCUG ACCAAUAGCAUCAAGAGCGAGAAGGCCAGAGAGAGCCUG CUGCAGGACAUCAACAACGAGUUCAUGGAAGUGACCGAG AAGAUCCAGGUGGCCAGCGACAACACCAACGACCUGAUC CAGAGCGGCGUGAACACCCGGCUGCUGACCAUCCAGAGCC ACGUGCAGAACUACAUCCCCAUCAGCCUGACCCAGCAGAU CAGCGACCUGCGGAAGUUCAUCAGCGAGAUCACCAUCCG GAACGACAACCAGGAAGUGCCCCCCCAGAGAAUCACCCAC GACGUGGGCAUCAAGCCCCUGAACCCCGACGAUUUCUGG CGGUGUACAAGCGGCCUGCCCAGCCUGAUGAAGACCCCCA AGAUCCGGCUGAUGCCUGGCCCUGGACUGCUGGCCAUGC CUACCACAGUGGAUGGCUGUGUGCGGACCCCCAGCCUCG UGAUCAACGAUCUGAUCUACGCCUACACCAGCAACCUGA UCACCCGGGGCUGCCAGGAUAUCGGCAAGAGCUACCAGG UGCUGCAGAUCGGCAUCAUCACCGUGAACUCCGACCUGG UGCCCGACCUGAACCCUCGGAUCAGCCACACCUUCAACAU CAACGACAACAGAAAGAGCUGCAGCCUGGCUCUGCUGAA CACCGACGUGUACCAGCUGUGCAGCACCCCCAAGGUGGAC GAGAGAAGCGACUACGCCAGCAGCGGCAUCGAGGAUAUC GUGCUGGACAUCGUGAACUACGACGGCAGCAUCAGCACC ACCCGGUUCAAGAACAACAACAUCAGCUUCGACCAGCCCU ACGCCGCCCUGUACCCUUCUGUGGGCCCUGGCAUCUACUA CAAGGGCAAGAUCAUCUUCCUGGGCUACGGCGGCCUGGA ACACCCCAUCAACGAGAACGCCAUCUGCAACACCACCGGC UGCCCUGGCAAGACCCAGAGAGACUGCAAUCAGGCCAGC CACAGCCCUGGUUCAGCGACCGCAGAAUGGUCAACUCU AUCAUCGUGGUGGACAAGGGCCUGAACAGCGUGCCCAAG CUGAAAGUGUGGACAAUCAGCAUGCGCCAGAACUACUGG GGCAGCGAGGGCAGACUUCUGCUGCUGGGAAACAAGAUC UACAUCUACACCCGGUCCACCAGCUGGCACAGCAAACUGC | 6 |

TABLE 7-continued

Sequences of Antigens encoded by hMPV/HPIV3 mRNA vaccines

| | | |
|---|---|---|
| | AGCUGGGAAUCAUCGACAUCACCGACUACAGCGACAUCC<br>GGAUCAAGUGGACCUGGCACAACGUGCUGAGCAGACCCG<br>GCAACAAUGAGUGCCCUUGGGGCCACAGCUGCCCCGAUG<br>GAUGUAUCACCGGCGUGUACACCGACGCCUACCCCCUGAA<br>UCCUACCGGCUCCAUCGUGUCCAGCGUGAUCCUGGACAGC<br>CAGAAAAGCAGAGUGAACCCCGUGAUCACAUACAGCACC<br>GCCACCGAGAGAGUGAACGAACUGGCCAUCAGAAACAAG<br>ACCCUGAGCGCCGGCUACACCACCACAAGCUGCAUCACAC<br>ACUACAACAAGGGCUACUGCUUCCACAUCGUGGAAAUCA<br>ACCACAAGUCCCUGAACACCUUCCAGCCCAUGCUGUUCAA<br>GACCGAGAUCCCCAAGAGCUGCUCC | |
| 3' UTR | UGAUAAUAGGCUGGAGCCUCGGUGGCCAUGCUUCUUGCC<br>CCUUGGGCCUCCCCCCAGCCCCUCCUCCCCUUCCUGCACC<br>CGUACCCCCGUGGUCUUUGAAUAAAGUCUGAGUGGGCGG<br>C | 13 |
| Corresponding amino acid sequence | MEYWKHTNHGKDAGNELETSTATHGNKLTNKITYILWTITLV<br>LLSIVFIIVLTNSIKSEKARESLLQDINNEFMEVTEKIQVASDNT<br>NDLIQSGVNTRLLTIQSHVQNYIPISLTQQISDLRKFISEITIRND<br>NQEVPPQRITHDVGIKPLNPDDFWRCTSGLPSLMKTPKIRLMP<br>GPGLLAMPTTVDGCVRTPSLVINDLIYAYTSNLITRGCQDIGKS<br>YQVLQIGIITVNSDLVPDLNPRISHTFNINDNRKSCSLALLNTD<br>VYQLCSTPKVDERSDYASSGIEDIVLDIVNYDGSISTTRFKNNN<br>ISFDQPYAALYPSVGPGIYYKGKIIFLGYGGLEHPINENAICNTT<br>GCPGKTQRDCNQASHSPWFSDRRMVNSIIVVDKGLNSVPKLK<br>VWTISMRQNYWGSEGRLLLLGNKIYIYTRSTSWHSKLQLGIID<br>ITDYSDIRIKWTWHNVLSRPGNNECPWGHSCPDGCITGVYTD<br>AYPLNPTGSIVSSVILDSQKSRVNPVITYSTATERVNELAIRNK<br>TLSAGYTTTSCITHYNKGYCFHIVEINHKSLNTFQPMLFKTEIP<br>KSCS | 9 |
| PolyA tail | 100 nt | |

International Patent Application No. PCT/US2016/58327 is herein incorporated by reference in its entirety.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising:
a human metapneumovirus (hMPV) messenger ribonucleic acid (mRNA) comprising a 5' UTR that comprises the sequence of SEQ ID NO:12, an open reading frame that comprises the sequence of SEQ ID NO:4, and a 3' UTR that comprises the sequence of SEQ ID NO:13; and
a human parainfluenza virus 3 (hPIV3) mRNA comprising a 5' UTR that comprises the sequence of SEQ ID NO:12, an open reading frame that comprises the sequence of SEQ ID NO:5, and a 3' UTR that comprises the sequence of SEQ ID NO:13.

2. The composition of claim 1, wherein the hMPV mRNA comprises the sequence of SEQ ID NO: 14.

3. The composition of claim 1, wherein the hPIV3 mRNA comprises the sequence of SEQ ID NO: 15.

4. The composition of claim 1 comprising the hMPV mRNA and the hPIV3 mRNA at a mass ratio of 1:1.

5. The composition of claim 1, wherein the hMPV mRNA comprises a 7mG(5')ppp(5')NlmpNp cap and/or the hPIV3 mRNA comprises a 7mG(5')ppp(5')NlmpNp cap.

6. The composition of claim 1, wherein the hMPV mRNA comprises a polyA tail and/or the hPIV3 mRNA comprises a polyA tail.

7. The composition of claim 1, wherein the hMPV mRNA and/or the hPIV3 mRNA comprises a chemical modification.

8. The composition of claim 7, wherein the chemical modification is 1-methylpseudouridine.

9. The composition of claim 1 comprising 25 µg 200 µg of the hMPV mRNA.

10. The composition of claim 1 comprising 25 µg 200 µg of the hPIV3 mRNA.

11. The composition of claim 1 further comprising mRNA encoding a respiratory syncytial virus (RSV) antigen.

12. The composition of claim 1, wherein the hMPV mRNA and the hPIV3 mRNA are in a lipid nanoparticle that comprises 1-5 mol % PEG-modified lipid; 10-20 mol % non-cationic lipid; 35-45 mol % cholesterol; and 40-50 mol % ionizable cationic lipid.

13. The composition of claim 12, wherein the PEG-modified lipid is 1,2 dimyristoyl-sn-glycerol, methoxypolyethyleneglycol (PEG2000 DMG), the non-cationic lipid is 1,2 distearoyl-sn-glycero-3-phosphocholine (DSPC), and the ionizable cationic lipid has the structure of Compound 1:

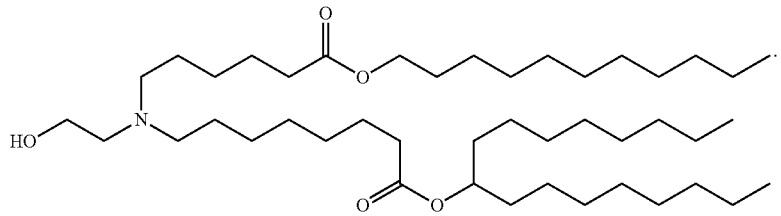

(Compound 1)

14. A composition comprising:
25 µg-200 µg human metapneumovirus (hMPV) messenger ribonucleic acid (mRNA) comprising the sequence of SEQ ID NO:14; and
25 µg-200 µg a human parainfluenza virus 3 (hPIV3) mRNA comprising the sequence of SEQ ID NO:15.

15. The composition of claim 14, wherein the hMPV mRNA and the hPIV3 mRNA are in a lipid nanoparticle that comprises 1-5 mol % 1,2 dimyristoyl-sn-glycerol, methoxypolyethyleneglycol (PEG2000 DMG); 10-20 mol % 1,2 distearoyl-sn-glycero-3-phosphocholine (DSPC); 35-45 mol % cholesterol; and 40-50 mol % ionizable cationic lipid having the structure of Compound 1:

(Compound 1)

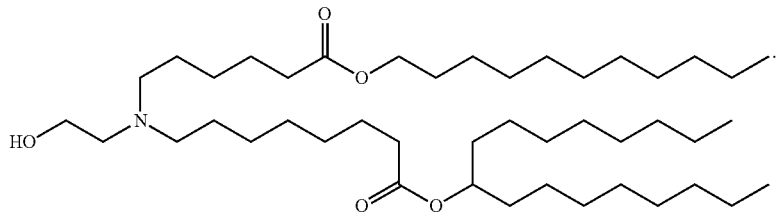

16. The composition of claim 14 further comprising mRNA encoding a respiratory syncytial virus (RSV) antigen.

17. A method comprising administering to a subject the composition of claim 12 in an amount effective to induce a neutralizing antibody response against hMPV and/or hPIV3 in the subject.

18. The method of claim 17, wherein the subject is immunocompromised and/or has a pulmonary disease.

19. The method of claim 17, wherein the subject is 5 years of age or younger, or 65 years of age or older.

20. The method of claim 17 comprising administering to the subject at least two doses of the composition.

21. The method of claim 20, wherein a neutralizing antibody titer against hMPV in the subject at 14 days post-administration of the second dose of the composition is increased by 8-10 fold relative to a control, and/or a neutralizing antibody titer against hPIV3 in the subject at 14 days post-administration of the second dose of the composition is increased by 4-10 fold relative to a control.

22. The composition of claim 12, wherein the lipid nanoparticle comprises 2.5 mol % PEG2000 DMG, 10 mol % DSPC, 38.5 mol % cholesterol; and 49 mol % ionizable cationic lipid, and wherein the ionizable lipid has the structure of Compound 1:

(Compound 1)

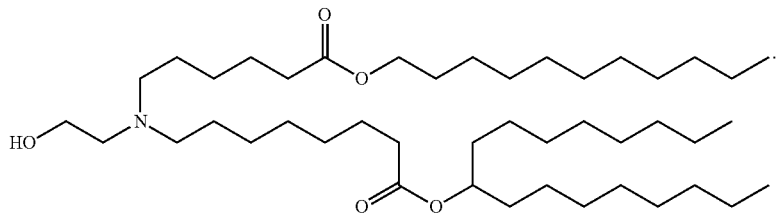

23. The composition of claim 12, wherein the lipid nanoparticle comprises 2.5 mol % PEG2000 DMG, 11 mol % DSPC, 38.5 mol % cholesterol; and 48 mol % ionizable cationic lipid, and wherein the ionizable lipid has the structure of Compound 1:

(Compound 1)

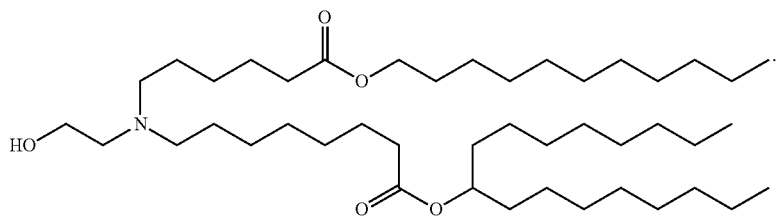

24. The composition of claim 12, wherein the lipid nanoparticle comprises 3.5 mol % PEG2000 DMG, 11 mol % DSPC, 38.5 mol % cholesterol; and 49 mol % ionizable cationic lipid, and wherein the ionizable lipid has the structure of Compound 1:

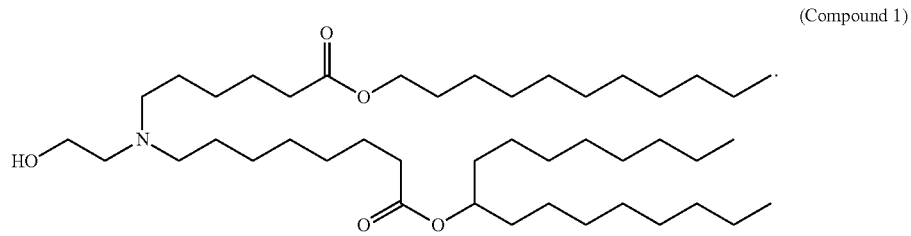 [SMILES: CCCCCCCCCCCOC(=O)CCCCCN(CCO)CCCCCCCC(=O)OC(CCCCCCCC)CCCCCCCC]
(Compound 1)

25. The composition of claim 15, wherein the lipid nanoparticle comprises 2.5 mol % PEG2000 DMG, 10 mol % DSPC, 38.5 mol % cholesterol; and 49 mol % ionizable cationic lipid, and wherein the ionizable lipid has the structure of Compound 1:

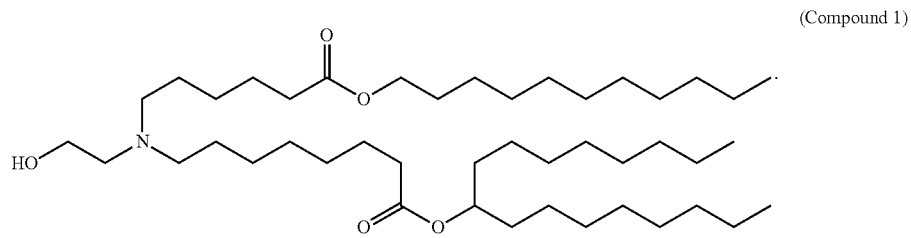 [SMILES: CCCCCCCCCCCOC(=O)CCCCCN(CCO)CCCCCCCC(=O)OC(CCCCCCCC)CCCCCCCC]
(Compound 1)

26. The composition of claim 15, wherein the lipid nanoparticle comprises 2.5 mol % PEG2000 DMG, 11 mol % DSPC, 38.5 mol % cholesterol; and 48 mol % ionizable cationic lipid, and wherein the ionizable lipid has the structure of Compound 1:

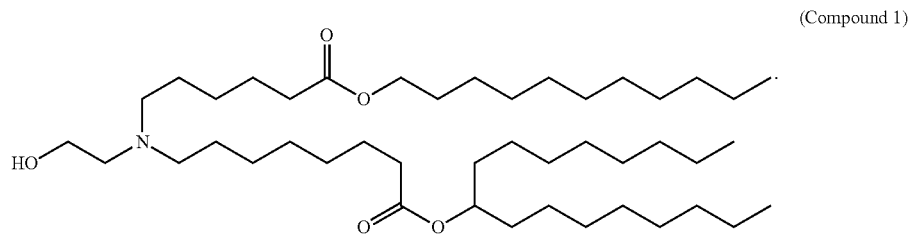 [SMILES: CCCCCCCCCCCOC(=O)CCCCCN(CCO)CCCCCCCC(=O)OC(CCCCCCCC)CCCCCCCC]
(Compound 1)

27. The composition of claim 15, wherein the lipid nanoparticle comprises 3.5 mol % PEG2000 DMG, 11 mol % DSPC, 38.5 mol % cholesterol; and 49 mol % ionizable cationic lipid, and wherein the ionizable lipid has the structure of Compound 1:

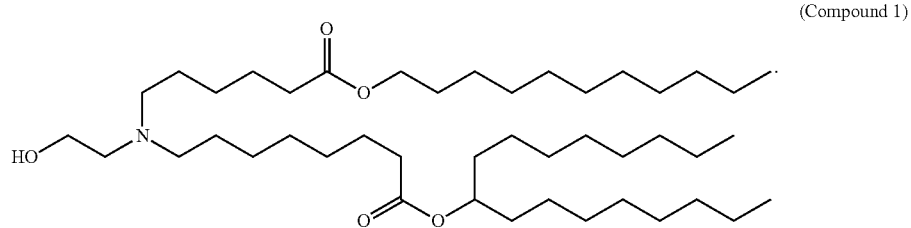 [SMILES: CCCCCCCCCCCOC(=O)CCCCCN(CCO)CCCCCCCC(=O)OC(CCCCCCCC)CCCCCCCC]
(Compound 1)
28. The composition of claim 8, wherein 100% of uracil in the open reading frame of the hMPV mRNA and open reading frame of the hP

SEQUENCE LISTING

<160> NUMBER OF SEQ ID NOS: 25

<210> SEQ ID NO 1
<211> LENGTH: 1620
<212> TYPE: DNA
<213> ORGANISM: Artificial Sequence
<220> FEATURE:
<223> OTHER INFORMATION: Synthetic Polynucleotide

<400> SEQUENCE: 1

```
atgagctgga aggtggtgat tatcttcagc ctgctgatta cacctcaaca cggcctgaag      60
gagagctacc tggaagagag ctgctccacc atcaccgagg gctacctgag cgtgctgcgg     120
accggctggt acaccaacgt gttcaccctg gaggtgggcg acgtggagaa cctgacctgc     180
agcgacggcc ctagcctgat caagaccgag ctggacctga ccaagagcgc tctgagagag     240
ctgaagaccg tgtccgccga ccagctggcc agagaggaac agatcgagaa ccctcggcag     300
agcagattcg tgctgggcgc catcgctctg ggagtcgccg ctgccgctgc agtgacagct     360
```

```
ggagtggcca ttgctaagac catcagactg gaaagcgagg tgacagccat caacaatgcc      420
ctgaagaaga ccaacgaggc cgtgagcacc ctgggcaatg gagtgagagt gctggccaca      480
gccgtgcggg agctgaagga cttcgtgagc aagaacctga ccagagccat caacaagaac      540
aagtgcgaca tcgatgacct gaagatggcc gtgagcttct cccagttcaa cagacggttc      600
ctgaacgtgg tgagacagtt ctccgacaac gctggaatca cacctgccat tagcctggac      660
ctgatgaccg acgccgagct ggctagagcc gtgcccaaca tgcccaccag cgctggccag      720
atcaagctga tgctggagaa cagagccatg gtgcggagaa agggcttcgg catcctgatt      780
ggggtgtatg gaagctccgt gatctacatg gtgcagctgc ccatcttcgg cgtgatcgac      840
acaccctgct ggatcgtgaa ggccgctcct agctgctccg agaagaaagg aaactatgcc      900
tgtctgctga gagaggacca gggctggtac tgccagaacg ccggaagcac agtgtactat      960
cccaacgaga aggactgcga gaccagaggc gaccacgtgt ctgcgacac cgctgccgga     1020 atcaacgtgg ccgagcagag caaggagtgc aacatcaaca tcagcacaac caactacccc     1080
tgcaaggtga gcaccggacg gcaccccatc agcatggtgg ctctgagccc tctgggcgct     1140
ctggtggcct gctataaggg cgtgtcctgt agcatcggca gcaatcgggt gggcatcatc     1200
aagcagctga acaagggatg ctcctacatc accaaccagg acgccgacac cgtgaccatc     1260
gacaacaccg tgtaccagct gagcaaggtg gagggcgagc agcacgtgat caagggcaga     1320
cccgtgagct ccagcttcga ccccatcaag ttccctgagg accagttcaa cgtggccctg     1380
gaccaggtgt ttgagaacat cgagaacagc caggccctgg tggaccagag caacagaatc     1440
ctgtccagcg ctgagaaggg caacaccggc ttcatcattg tgatcattct gatcgccgtg     1500
ctgggcagct ccatgatcct ggtgagcatc ttcatcatta tcaagaagac caagaaaccc     1560
accggagccc ctcctgagct gagcggcgtg accaacaatg gcttcattcc ccacaactga     1620
```

<210> SEQ ID NO 2
<211> LENGTH: 1617
<212> TYPE: DNA
<213> ORGANISM: Artificial Sequence
<220> FEATURE:
<223> OTHER INFORMATION: Synthetic Polynucleotide

<400> SEQUENCE: 2

```
atgcccatca gcatcctgct gatcatcacc acaatgatca tggccagcca ctgccagatc       60
gacatcacca agctgcagca cgtgggcgtg ctcgtgaaca gccccaaggg catgaagatc      120
agccagaact tcgagacacg ctacctgatc ctgagcctga tccccaagat cgaggacagc      180
aacagctgcg gcgaccagca gatcaagcag tacaagcggc tgctggacag actgatcatc      240
cccctgtacg acgcctgcg gctgcagaaa gacgtgatcg tgaccaacca ggaaagcaac      300
gagaacaccg acccccggac cgagagattc ttcggcggcg tgatcggcac aatcgccctg      360
ggagtggcca caagcgccca gattacagcc gctgtggccc tggtggaagc aagcaggcc      420 agaagcgaca tcgagaagct gaaagaggcc atccgggaca ccaacaaggc cgtgcagagc      480
gtgcagtcca gcgtgggcaa tctgatcgtg gccatcaagt ccgtgcagga ctacgtgaac      540
aaagaaatcg tgcctctctat cgccggctg ggctgtgaag ctgccggact gcagctgggc      600
attgccctga cacagcacta cagcgagctg accaacatct tcggcgacaa catcggcagc      660
ctgcaggaaa agggcattaa gctgcaggga atcgccagcc tgtaccgcac caacatcacc      720
gagatcttca ccaccagcac cgtggataag tacgacatct acgacctgct gttcaccgag      780
```

| | |
|---|---|
| agcatcaaag tgcgcgtgat cgacgtggac ctgaacgact acagcatcac cctgcaagtg | 840 |
| cggctgcccc tgctgaccag actgctgaac acccagatct acaaggtgga cagcatctcc | 900 |
| tacaacatcc agaaccgcga gtggtacatc cctctgccca gccacattat gaccaagggc | 960 |
| gcctttctgg gcggagccga cgtgaaagag tgcatcgagg ccttcagcag ctacatctgc | 1020 |
| cccagcgacc ctggcttcgt gctgaaccac gagatggaaa gctgcctgag cggcaacatc | 1080 |
| agccagtgcc ccagaaccac cgtgacctcc gacatcgtgc ccagatacgc cttcgtgaat | 1140 |
| ggcggcgtgg tggccaactg catcaccacc acctgtacct gcaacggcat cggcaaccgg | 1200 |
| atcaaccagc tccccgatca gggcgtgaag attatcaccc acaaagagtg taacaccatc | 1260 |
| ggcatcaacg gcatgctgtt caataccaac aaagagggca ccctggcctt ctacaccccc | 1320 |
| gacgatatca ccctgaacaa ctccgtggct ctggaccccca tcgacatctc catcgagctg | 1380 |
| aacaaggcca agagcgacct ggaagagtcc aaagagtgga tccggcggag caaccagaag | 1440 |
| ctggactcta tcggcagctg gcaccagagc agcaccacca tcatcgtgat cctgattatg | 1500 |
| atgattatcc tgttcatcat caacattacc atcatcacta tcgccattaa gtactaccgg | 1560 |
| atccagaaac ggaaccgggt ggaccagaat gacaagccct acgtgctgac aaacaag | 1617 |

<210> SEQ ID NO 3
<211> LENGTH: 1716
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| atggaatact ggaagcacac caaccacggc aaggacgccg caacgagct ggaaaccagc | 60 |
| acagccacac acggcaacaa gctgaccaac aagatcaccct catcctgtg gaccatcacc | 120 |
| ctggtgctgc tgagcatcgt gttcatcatc gtgctgacca atagcatcaa gagcgagaag | 180 |
| gccagagaga gcctgctgca ggacatcaac aacgagttca tggaagtgac cgagaagatc | 240 |
| caggtggcca gcgacaacac caacgacctg atccagagcg cgtgaacac ccggctgctg | 300 |
| accatccaga gccacgtgca gaactacatc cccatcagcc tgacccagca gatcagcgac | 360 |
| ctgcggaagt tcatcagcga gatcaccatc cggaacgaca accaggaagt gccccccccag | 420 |
| agaatcaccc acgacgtggg catcaagccc ctgaaccccg acgatttctg gcggtgtaca | 480 |
| agcggcctgc ccagcctgat gaagaccccc aagatccggc tgatgcctgg ccctggactg | 540 |
| ctggccatgc ctaccacagt ggatggctgt gtgcggaccc ccagcctcgt gatcaacgat | 600 |
| ctgatctacg cctacaccag caacctgatc acccggggct gccaggatat cggcaagagc | 660 |
| taccaggtgc tgcagatcgg catcatcacc gtgaactccg acctggtgcc cgacctgaac | 720 |
| cctcggatca gccacaccctt caacatcaac gacaacagaa agagctgcag cctggctctg | 780 |
| ctgaacaccg acgtgtacca gctgtgcagc accccccaagg tggacgagag aagcgactac | 840 |
| gccagcagcg gcatcgagga tatcgtgctg gacatcgtga actacgacgg cagcatcagc | 900 |
| accacccggt tcaagaacaa caacatcagc ttcgaccagc cctacgccgc cctgtaccct | 960 |
| tctgtgggcc ctggcatcta ctacaagggc aagatcatct tcctgggcta cggcggcctg | 1020 |
| gaacaccccca tcaacgagaa cgccatctgc aacaccaccg gctgccctgg caagacccag | 1080 |
| agagactgca atcaggccag ccacagcccc tggttcagcg accgcagaat ggtcaactct | 1140 |
| atcatcgtgg tggacaaggg cctgaacagc gtgcccaagc tgaaagtgtg gacaatcagc | 1200 |
| atgcgccaga actactgggg cagcgagggc agacttctgc tgctgggaaa caagatctac | 1260 |

| | |
|---|---|
| atctacaccc ggtccaccag ctggcacagc aaactgcagc tgggaatcat cgacatcacc | 1320 |
| gactacagcg acatccggat caagtggacc tggcacaacg tgctgagcag acccggcaac | 1380 |
| aatgagtgcc cttggggcca cagctgcccc gatggatgta tcaccggcgt gtacaccgac | 1440 |
| gcctacccc tgaatcctac cggctccatc gtgtccagcg tgatcctgga cagccagaaa | 1500 |
| agcagagtga acccgtgat cacatacagc accgccaccg agagtgaa cgaactggcc | 1560 |
| atcagaaaca agaccctgag cgccggctac accaccacaa gctgcatcac acactacaac | 1620 |
| aagggctact gcttccacat cgtggaaatc aaccacaagt ccctgaacac cttccagccc | 1680 |
| atgctgttca agaccgagat ccccaagagc tgctcc | 1716 |

<210> SEQ ID NO 4
<211> LENGTH: 1620
<212> TYPE: RNA
<213> ORGANISM: Artificial Sequence
<220> FEATURE:
<223> OTHER INFORMATION: Synthetic Polynucleotide

<400> SEQUENCE: 4

| | |
|---|---|
| augagcugga aggugugau uaucuucagc cugcugauua caccucaaca cggccugaag | 60 |
| gagagcuacc uggaagagag cugcuccacc aucaccgagg gcuaccugag cgugcugcgg | 120 |
| accggcuggu acaccaacgu guucacccug gaggugggcg acguggagaa ccugaccugc | 180 |
| agcgacggcc cuagccugau caagaccgag cuggaccuga ccaagagcgc ucugagagag | 240 |
| cugaagaccg uguccgccga ccagcuggcc agagaggaac agaucgagaa ccccucggcag | 300 |
| agcagauucg ugcugggcgc caucgcucug ggagucgccg cugccgcugc agugacagcu | 360 |
| ggaguggcca uugcuaagac caucagacug gaaagcgagg ugacagccau caacaaugcc | 420 |
| cugaagaaga ccaacgaggc cgugagcacc cugggcaaug gagugagagu gcuggccaca | 480 |
| gccgugcggg agcugaagga cuucgugagc aagaaccuga ccagagccau caacaagaac | 540 |
| aagugcgaca ucgaugaccu gaagauggcc gugagcuucu cccaguucaa cagacgguuc | 600 |
| cugaacgugg ugagacaguu uccgacaac gcuggaauca caccugccau uagccuggac | 660 |
| cugaugaccg acgccagcu ggcuagagcc gucccaaca ugcccaccag cgcuggccag | 720 |
| aucaagcuga gcuggagaa cagagccaug gugcggagaa agggcuucgg cauccugauu | 780 |
| ggggugugu gaagcuccgu gaucuacaug gugcagcugc ccaucuucgg cgugaucgac | 840 |
| acacccugcu ggaucgugaa ggccgcuccu agcugcuccg agaagaaagg aaacuaugcc | 900 |
| ugucugcuga gagggccca gggcuggac ugccagaacg ccggaagcac aguguacuau | 960 |
| cccaacgaga aggacugcga ccagagggc gaccacgugu ucugcgacac cgcugccgga | 1020 |
| aucaacugug ccgagcagag caaggagugc aacaucaaca ucagcacaac caacuacccc | 1080 |
| ugcaaggugga gcaccggacg gcaccccauc agcauggugg cucugagccc ucugggcgcu | 1140 |
| cugguggccu gcuauaaggg cgugucuegu agcaucggca gcaaucgggu gggcaucauc | 1200 |
| aagcagcuga acaagggaug cucccuacauc accaaccagg acgccgacac cgugaccauc | 1260 |
| gacaacaccg uguaccagcu gagcaaggug gagggcgagc agcacgugau caagggcaga | 1320 |
| cccgugagcu ccagcuucga ccccaucaag uucccugagg accaguucaa cguggcccug | 1380 |
| gaccagugu uugagaacau cgagaacagc caggcccugg ugaccagag caacagaauc | 1440 |
| cuguccagcg cugagaaggg caacaccggc uucaucauug ugaucauucu gaucgccgug | 1500 |
| cugggcagcu ccaugaucu ggugagcauc uucaucauua ucaagaagac caagaaaccc | 1560 | accggagccc cuccugagcu gagcggcgug accaacaaug gcuucauucc ccacaacuga    1620

<210> SEQ ID NO 5
<211> LENGTH: 1617
<212> TYPE: RNA
<213> ORGANISM: Artificial Sequence
<220> FEATURE:
<223> OTHER INFORMATION: Synthetic Polynucleotide

<400> SEQUENCE: 5
augcccauca gcauccugcu gaucaucacc acaaugauca uggccagcca cugccagauc      60
gacaucacca gcugcagca cgugggcgug cucgugaaca gccccaaggg caugaagauc     120
agccagaacu ucgagacacg cuaccugauc cugagccuga uccccaagau cgaggacagc    180
aacagcugcg gcgaccagca gaucaagcag uacaagcggc ugcuggacag acugaucauc    240
cccccuguacg acggccugcg gcugcagaaa gacgugaucu ugaccaacca ggaaagcaac    300
gagaacaccg accccccggac cgagagauuc uucggcggcg ugaucggcac aaucgcccug    360
ggaguggcca aagcgcccca gauuacagcc gcugguggcc ugguggaagc caagcaggcc    420
agaagcgaca ucgagaagcu gaaagaggcc auccgggaca ccaacaaggc cgugcagagc    480
gugcagucca gcgugggcaa ucugaucgug gccaucaagu ccgucagga cuacgugaac    540
aaagaaaucg ugcccucuau cgcccggcug ggcugugaag cugccggacu gcagcugggc    600
auugcccuga cacagcacua cagcgagcug accaacaucu ucggcgacaa caucggcagc    660
cugcaggaaa agggcauuaa gcugcaggga aucgccagcc uguaccgcac caacaucacc    720
gagaucuuca ccaccagcac cguggauaag uacgacaucu acgaccugcu guucaccgag    780
agcaucaaag ugcgcgugau cgacguggac cugaacgacu acagcaucac ccugcaagug    840
cggcugcccc ugcugaccag acugcugaac cccagaucu acaaggugga cagcaucucc    900
uacaacaucc agaaccgcga gugguacauc ccucugccca gccacauuau gaccaagggc    960
gccuuucugg cggagccga cgugaaagag ugcaucgagg ccuucagcag cuacaucugc   1020
cccagcgacc cuggcuucgu gcugaaccac gagauggaaa gcugccugag cggcaacauc   1080
agccagugcc ccagaaccac cgugaccucc gacaucgugc ccagauacgc cuucgugaau   1140
ggcggcgugg uggccaacug caucaccacc accuguaccu gcaacggcau cggcaaccgg   1200
aucaaccagc cucccgauca gggcgugaag auuaucaccc acaaagagug uaacaccauc   1260
ggcaucaacg gcaugcuguu caauaccaac aaagagggca cccuggccuu cuacacccccc   1320
gacgauauca cccugaacaa cuccguggcu cuggaccccca ucgacaucuc caucgagcug   1380
aacaaggcca agagcgaccu ggaagagucc aaagaguggga uccggcggag caaccagaag   1440
cuggacucua ucggcagcug gcaccagagc agcaccacca ucaucgugau ccugauuaug   1500
augauuaucc uguucaucau caacauuacc aucaucacua ucgccauuaa guacuaccgg   1560
auccagaaac ggaaccgggu ggaccagaau gacaagcccu acgugcugac aaacaag     1617

<210> SEQ ID NO 6
<211> LENGTH: 1716
<212> TYPE: RNA
<213> ORGANISM: Artificial Sequence
<220> FEATURE:
<223> OTHER INFORMATION: Synthetic Polynucleotide

<400> SEQUENCE: 6
auggaauacu ggaagcacac caaccacggc aaggacgccg gcaacgagcu ggaaccagc      60
acagccacac acggcaacaa gcugaccaac aagaucaccu acauccugug gaccaucacc    120

-continued

| | |
|---|---|
| cuggugcugc ugagcaucgu guucaucauc gugcugacca auagcaucaa gagcgagaag | 180 |
| gccagagaga gccugcugca ggacaucaac aacgaguuca uggaagugac cgagaagauc | 240 |
| cagguggcca gcgacaacac caacgaccug auccagagcg gcgugaacac ccggcugcug | 300 |
| accauccaga gccacgugca gaacuacauc cccaucagcc ugacccagca gaucagcgac | 360 |
| cugcggaagu caucagcga gaucaccauc cggaacgaca ccaggaagu gcccccccag | 420 |
| agaaucaccc acgacggg caucaagccc ugaaccccg acgauuucug gcgguguaca | 480 |
| agcggccugc ccagccugau gaagaccccc aagauccggc ugaugccugg cccuggacug | 540 |
| cuggccaugc cuaccacagu ggauggcugu gugcggaccc ccagccucgu gaucaacgau | 600 |
| cugaucuacg ccuacaccag caaccugauc acccggggcu gccaggauau cggcaagagc | 660 |
| uaccagguc ugcagaucgg caucaucacc gugaacuccg accuggugcc cgaccugaac | 720 |
| ccucggauca gccacaccuu caacaucaac gacaacagaa agagcugcag ccuggcucug | 780 |
| cugaacaccg acguguacca gcugugcagc accccaagg uggacgagag aagcgacuac | 840 |
| gccagcagcg gcaucgagga uaucgugcug gacaucguga acuacgacgg cagcaucagc | 900 |
| accacccggu ucaagaacaa caacaucagc uucgaccagc ccuacgccgc ccuguacccu | 960 |
| ucugugggcc cuggcaucua cuacaagggc aagaucaucu uccugggcua cggcggccug | 1020 |
| gaacacccca ucaacgagaa cgccaucugc aacaccaccg gcugcccugg caagacccag | 1080 |
| agagacugca aucaggccag ccacagcccc ugguucagcg accgcagaau ggucaacucu | 1140 |
| aucaucgugg uggacaaggg ccugaacagc gugcccaagc ugaaagugug dacaaucagc | 1200 |
| augcgccaga acuacggggg cagcgagggc agacuucugc ugcugggaaa caagaucuac | 1260 |
| aucuacaccc gguccaccag cuggcacagc aaacugcagc ugggaaucau cgacaucacc | 1320 |
| gacuacagcg acauccggau caaguggacc uggcacaacg ugcugagcag acccggcaac | 1380 |
| aaugagugcc cuuggggcca cagcugcccc gauggaugua ucaccggcgu guacaccgac | 1440 |
| gccuaccccc ugaauccuac cggcuccauc guguccagcg ugauccugga cagccagaaa | 1500 |
| agcagaguga accccgugau cacauacagc accgccaccg agagagugaa cgaacuggcc | 1560 |
| aucagaaaca gacccugag cgccggcuac accaccacaa gcugcaucac acacuacaac | 1620 |
| aagggcuacu gcuuccacau cguggaaauc aaccacaagu cccugaacac cuuccagccc | 1680 |
| augcuguuca gaccgagau ccccaagagc ugcucc | 1716 |

<210> SEQ ID NO 7
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 7

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

```
Leu Lys Thr Val Ser Ala Asp Gln Leu Ala Arg Glu Glu Ile Glu
                 85                  90                  95

Asn Pro Arg Gln Ser Arg Phe Val Leu Gly Ala Ile Ala Leu Gly Val
            100                 105                 110

Ala Ala Ala Ala Ala Val Thr Ala Gly Val Ala Ile Ala Lys Thr Ile
            115                 120                 125

Arg Leu Glu Ser Glu Val Thr Ala Ile Asn Asn Ala Leu Lys Lys Thr
        130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Pro Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495
```

-continued

```
Leu Ile Ala Val Leu Gly Ser Ser Met Ile Leu Val Ser Ile Phe Ile
                500                 505                 510
Ile Ile Lys Lys Thr Lys Lys Pro Thr Gly Ala Pro Pro Glu Leu Ser
            515                 520                 525
Gly Val Thr Asn Asn Gly Phe Ile Pro His Asn
        530                 535
```

<210> SEQ ID NO 8
<211> LENGTH: 539
<212> TYPE: PRT
<213> ORGANISM: Artificial Sequence
<220> FEATURE:
<223> OTHER INFORMATION: Synthetic Polypeptide

<400> SEQUENCE: 8

```
Met Pro Ile Ser Ile Leu Leu Ile Ile Thr Thr Met Ile Met Ala Ser
1               5                   10                  15
His Cys Gln Ile Asp Ile Thr Lys Leu Gln His Val Gly Val Leu Val
                20                  25                  30
Asn Ser Pro Lys Gly Met Lys Ile Ser Gln Asn Phe Glu Thr Arg Tyr
            35                  40                  45
Leu Ile Leu Ser Leu Ile Pro Lys Ile Glu Asp Ser Asn Ser Cys Gly
        50                  55                  60
Asp Gln Gln Ile Lys Gln Tyr Lys Arg Leu Leu Asp Arg Leu Ile Ile
65                  70                  75                  80
Pro Leu Tyr Asp Gly Leu Arg Leu Gln Lys Asp Val Ile Val Thr Asn
                85                  90                  95
Gln Glu Ser Asn Glu Asn Thr Asp Pro Arg Thr Glu Arg Phe Phe Gly
            100                 105                 110
Gly Val Ile Gly Thr Ile Ala Leu Gly Val Ala Thr Ser Ala Gln Ile
        115                 120                 125
Thr Ala Ala Val Ala Leu Val Glu Ala Lys Gln Ala Arg Ser Asp Ile
130                 135                 140
Glu Lys Leu Lys Glu Ala Ile Arg Asp Thr Asn Lys Ala Val Gln Ser
145                 150                 155                 160
Val Gln Ser Ser Val Gly Asn Leu Ile Val Ala Ile Lys Ser Val Gln
                165                 170                 175
Asp Tyr Val Asn Lys Glu Ile Val Pro Ser Ile Ala Arg Leu Gly Cys
            180                 185                 190
Glu Ala Ala Gly Leu Gln Leu Gly Ile Ala Leu Thr Gln His Tyr Ser
        195                 200                 205
Glu Leu Thr Asn Ile Phe Gly Asp Asn Ile Gly Ser Leu Gln Glu Lys
    210                 215                 220
Gly Ile Lys Leu Gln Gly Ile Ala Ser Leu Tyr Arg Thr Asn Ile Thr
225                 230                 235                 240
Glu Ile Phe Thr Thr Ser Thr Val Asp Lys Tyr Asp Ile Tyr Asp Leu
                245                 250                 255
Leu Phe Thr Glu Ser Ile Lys Val Arg Val Ile Asp Val Asp Leu Asn
            260                 265                 270
Asp Tyr Ser Ile Thr Leu Gln Val Arg Leu Pro Leu Leu Thr Arg Leu
        275                 280                 285
Leu Asn Thr Gln Ile Tyr Lys Val Asp Ser Ile Ser Tyr Asn Ile Gln
    290                 295                 300
Asn Arg Glu Trp Tyr Ile Pro Leu Pro Ser His Ile Met Thr Lys Gly
305                 310                 315                 320
```

Ala Phe Leu Gly Gly Ala Asp Val Lys Glu Cys Ile Glu Ala Phe Ser
            325                 330                 335

Ser Tyr Ile Cys Pro Ser Asp Pro Gly Phe Val Leu Asn His Glu Met
        340                 345                 350

Glu Ser Cys Leu Ser Gly Asn Ile Ser Gln Cys Pro Arg Thr Thr Val
        355                 360                 365

Thr Ser Asp Ile Val Pro Arg Tyr Ala Phe Val Asn Gly Gly Val Val
    370                 375                 380

Ala Asn Cys Ile Thr Thr Cys Thr Cys Asn Gly Ile Gly Asn Arg
385                 390                 395                 400

Ile Asn Gln Pro Pro Asp Gln Gly Val Lys Ile Ile Thr His Lys Glu
                405                 410                 415

Cys Asn Thr Ile Gly Ile Asn Gly Met Leu Phe Asn Thr Asn Lys Glu
            420                 425                 430

Gly Thr Leu Ala Phe Tyr Thr Pro Asp Asp Ile Thr Leu Asn Asn Ser
        435                 440                 445

Val Ala Leu Asp Pro Ile Asp Ile Ser Ile Glu Leu Asn Lys Ala Lys
    450                 455                 460

Ser Asp Leu Glu Glu Ser Lys Glu Trp Ile Arg Arg Ser Asn Gln Lys
465                 470                 475                 480

Leu Asp Ser Ile Gly Ser Trp His Gln Ser Ser Thr Ile Ile Val
                485                 490                 495

Ile Leu Ile Met Met Ile Ile Leu Phe Ile Ile Asn Ile Thr Ile Ile
            500                 505                 510

Thr Ile Ala Ile Lys Tyr Tyr Arg Ile Gln Lys Arg Asn Arg Val Asp
        515                 520                 525

Gln Asn Asp Lys Pro Tyr Val Leu Thr Asn Lys
    530                 535

<210> SEQ ID NO 9
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 9

Met Glu Tyr Trp Lys His Thr Asn His Gly Lys Asp Ala Gly Asn Glu
1               5                   10                  15

Leu Glu Thr Ser Thr Ala Thr His Gly Asn Lys Leu Thr Asn Lys Ile
            20                  25                  30

Thr Tyr Ile Leu Trp Thr Ile Thr Leu Val Leu Leu Ser Ile Val Phe
        35                  40                  45

Ile Ile Val Leu Thr Asn Ser Ile Lys Ser Glu Lys Ala Arg Glu Ser
    50                  55                  60

Leu Leu Gln Asp Ile Asn Asn Glu Phe Met Glu Val Thr Glu Lys Ile
65                  70                  75                  80

Gln Val Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Ile Ser Asp Leu Arg Lys Phe Ile Ser Glu Ile
        115                 120                 125

Thr Ile Arg Asn Asp Asn Gln Glu Val Pro Pro Gln Arg Ile Thr His
    130                 135                 140

-continued

```
Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
                180                 185                 190

Thr Pro Ser Leu Val Ile Asn Asp Leu Ile Tyr Ala Tyr Thr Ser Asn
            195                 200                 205

Leu Ile Thr Arg Gly Cys Gln Asp Ile Gly Lys Ser Tyr Gln Val Leu
        210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
                260                 265                 270

Lys Val Asp Glu Arg Ser Asp Tyr Ala Ser Ser Gly Ile Glu Asp Ile
            275                 280                 285

Val Leu Asp Ile Val Asn Tyr Asp Gly Ser Ile Ser Thr Thr Arg Phe
        290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Ala Ile Cys Asn Thr
            340                 345                 350

Thr Gly Cys Pro Gly Lys Thr Gln Arg Asp Cys Asn Gln Ala Ser His
        355                 360                 365

Ser Pro Trp Phe Ser Asp Arg Arg Met Val Asn Ser Ile Ile Val Val
        370                 375                 380

Asp Lys Gly Leu Asn Ser Val Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
            420                 425                 430

Gln Leu Gly Ile Ile Asp Ile Thr Asp Tyr Ser Asp Ile Arg Ile Lys
        435                 440                 445

Trp Thr Trp His Asn Val Leu Ser Arg Pro Gly Asn Asn Glu Cys Pro
        450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
            500                 505                 510

Thr Glu Arg Val Asn Glu Leu Ala Ile Arg Asn Lys Thr Leu Ser Ala
        515                 520                 525

Gly Tyr Thr Thr Thr Ser Cys Ile Thr His Tyr Asn Lys Gly Tyr Cys
        530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
```

-continued

```
              565                 570
```

<210> SEQ ID NO 10
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 10

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
            340                 345                 350

Ile Thr Ala Lys Thr Thr Thr Tyr Thr Asp Gly Thr Gly Val Ala Gln
```

```
                355                 360                 365
Thr Gly Ala Val Lys Phe Gly Gly Ala Asn Gly Lys Ser Glu Val Val
            370                 375                 380

Thr Ala Thr Asp Gly Lys Thr Tyr Leu Ala Ser Asp Leu Asp Lys His
385                 390                 395                 400

Asn Phe Arg Thr Gly Gly Glu Leu Lys Glu Val Asn Thr Asp Lys Thr
                405                 410                 415

Glu Asn Pro Leu Gln Lys Ile Asp Ala Ala Leu Ala Gln Val Asp Thr
            420                 425                 430

Leu Arg Ser Asp Leu Gly Ala Val Gln Asn Arg Phe Asn Ser Ala Ile
            435                 440                 445

Thr Asn Leu Gly Asn Thr Val Asn Asn Leu Ser Ser Ala Arg Ser Arg
            450                 455                 460

Ile Glu Asp Ser Asp Tyr Ala Thr Glu Val Ser Asn Met Ser Arg Ala
465                 470                 475                 480

Gln Ile Leu Gln Gln Ala Gly Thr Ser Val Leu Ala Gln Ala Asn Gln
                485                 490                 495

Val Pro Gln Asn Val Leu Ser Leu Leu Arg
            500                 505

<210> SEQ ID NO 11
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 11

Leu Gln Arg Val Arg Glu Leu Ala Val Gln Ser Ala Asn
1               5                   10

<210> SEQ ID NO 12
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 12
gggaauaaag agagaaaaga agaguaagaa gaaauauaag agccacc               47

<210> SEQ ID NO 13
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 13
ugauaauagg cuggagccuc gguggccaug cuucuugccc cuugggccuc ccccagccc   60 cuccuccccu uccugcaccc guaccccgu ggucuuugaa uaaagucuga gugggcggc   119

<210> SEQ ID NO 14
<211> LENGTH: 1786
<212> TYPE: RNA
<213> ORGANISM: Artificial Sequence
<220> FEATURE:
<223> OTHER INFORMATION: Synthetic Polynucleotide

<400> SEQUENCE: 14
gggaauaaag agagaaaaga agaguaagaa gaaauauaag agccaccaug agcuggaagg   60
```

```
uggugauuau cuucagccug cugauuacac cucaacacgg ccugaaggag agcuaccugg      120
aagagagcug cuccaccauc accgagggcu accugagcgu gcugcggacc ggcugguaca      180
ccaacguguu cacccuggag gugggcgacg uggagaaccu gaccugcagc gacggcccua      240
gccugaucaa gaccgagcug gaccugacca agagcgcucu gagagagcug aagaccgugu      300
ccgccgacca gcuggccaga gaggaacaga ucgagaaccc ucggcagagc agauucgugc      360
ugggcgccau cgcucuggga gucgccgcug ccgcugcagu gacagcugga guggccauug      420
cuaagaccau cagacuggaa agcgagguga cagccaucaa caaugcccug aagaagacca      480
acgaggccgu gagcacccug ggcaauggag ugagagugcu ggccacagcc gugcgggagc      540
ugaaggacuu cgugagcaag aaccugacca gagccaucaa caagaacaag ugcgacaucg      600
augaccugaa gauggccgug agcuucuccc aguucaacag acgguuccug aacgugguga      660
gacaguucuc cgacaacgcu ggaaucacac cugccauuag ccuggaccug augaccgacg      720
ccgagcuggc uagagccgug cccaacaugc ccaccagcgc uggccagauc aagcugaugc      780
uggagaacag agccaugguc cggagaaagg gcuucggcau ccgauuggga guguauggaa      840
gcuccgugau cuacaugguc cagcugccca ucuucggcgu gaucgacaca cccgcuggga      900
ucgugaaggc cgcuccuagc ugcuccgaga agaaaggaaa cuaugccugu cugcugagag      960
aggaccaggg cugguacugc cagaacgccg gaagcacagu guacuauccc aacgagaagg      1020
acugcgagac cagaggcgac cacguguucu gcgacaccgc ugccggaauc aacgugcccg      1080
agcagagcaa ggagugcaac aucaacauca gcacaaccaa cuaccccugc aaggugagca      1140
ccggacggca ccccaucagc augguggcuc ugagcccucu gggcgcucug guggccugcu      1200 auaaggcgu guccuguagc aucggcagca aucggguggg caucaucaag cagcugaaca      1260
agggaugcuc cuacaucacc aaccaggacg ccgacaccgu gaccaucgac aacaccgugu      1320
accagcugag caagguggag ggcgagcagc acgugaucaa gggcagaccc gugagcucca      1380
gcuucgaccc caucaaguuc ccugaggacc aguucaacgu ggcccuggac cagguguuug      1440
agaacaucga gaacagccag gcccuggugg accagagcaa cagaauccug uccagcgcug      1500
agaagggcaa caccggcuuc aucauuguga ucauucugau cgccgugcug ggcagccca      1560 ugauccuggu gagcaucuuc aucauuauca agaagaccaa gaaacccacc ggagcccuc      1620 cugagcugag cggcgugacc aacaauggcu ucauucccca caacgauga uaauaggcug      1680 gagccucggu ggccaugcuu cuugcccuu gggccucccc ccagccccuc uccccuucc      1740 ugcacccgua cccccguggu cuugaauaa agucugagug ggcggc              1786
```

<210> SEQ ID NO 15  
<211> LENGTH: 1783  
<212> TYPE: RNA  
<213> ORGANISM: Artificial Sequence  
<220> FEATURE:  
<223> OTHER INFORMATION: Synthetic Polynucleotide

<400> SEQUENCE: 15

```
gggaauaag agagaaaga agaguaagaa gaaauauaag agccaccaug cccaucagca       60
uccugcugau caucaccaca augaucaugg ccagccacug ccagaucgac aucaccaagc      120
ugcagcacgu gggcgugcuc gugaacagcc ccaagggcau gaagaucagc cagaacuucg      180
agacacgcua ccugauccug agccugaucc ccaagaucga ggacagcaac agcugcggcg      240
accagcagau caagcaguac aagcggcugc uggacagacu gaucaucccc cuguacgacg      300
```

```
gccugcggcu gcagaaagac gugaucguga ccaaccagga aagcaacgag aacaccgacc    360
cccggaccga gagauucuuc ggcggcguga ucggcacaau cgcccuggga guggccacaa    420
gcgcccagau uacagccgcu guggcccugg uggaagccaa gcaggccaga agcgacaucg    480
agaagcugaa agaggccauc cgggacacca acaaggccgu gcagagcgug caguccagcg    540
ugggcaaucu gaucguggcc aucaaguccg ugcaggacua cgugaacaaa gaaaucgugc    600
ccucuaucgc ccggcugggc ugugaagcug ccggacugca gcugggcauu gcccugacac    660
agcacuacag cgagcugacc aacaucuucg cgacaacau cggcagccug caggaaaagg    720
gcauuaagcu gcagggaauc gccagccugu accgcaccaa caucaccgag aucuucacca    780
ccagcaccgu ggauaaguac gacaucuacg accugcuguu caccgagagc aucaaagugc    840
gcgugaucga cguggaccug aacgacuaca gcaucacccu gcaagugcgg cugccccugc    900
ugaccagacu gcugaacacc cagaucuaca aggugacag cauccccuac aacauccaga    960
accgcgagug guacaucccu cugcccagcc acauuaugac caagggcgcc uuucuggggcg   1020 gagccgacgu gaaagagugc aucgaggccu ucagcagcua caucugcccc agcgacccug   1080
gcuucgugcu gaaccacgag auggaaagcu gccugagcgg caacaucagc cagugcccca   1140
gaaccaccgu gaccuccgac aucgugccca gaucgccuu cgugaauggc ggcguggugg   1200
ccaacugcau caccaccacc uguaccugac acggcaucgg caaccggauc aaccagccuc   1260
ccgaucaggg cgugaagauu uacacccaca agagaguaa caccaucggc aucaacggca   1320
ugcuguucaa uaccaacaaa gagggcaccc uggccuucua caccccgac gauaucaccc   1380 ugaacaacuc cguggcucug gaccccaucg acaucuccau cgagcugaac aaggccaaga   1440
gcgaccugga agauccaaa gaguggaucc ggcggagcaa ccagaagcug gacucuaucg   1500
gcagcuggca ccagagcagc accaccauca ucgugauccu gauuaugaug auuauccugu   1560
ucaucaucaa cauuaccauc aucacauacg ccauuaagua cuaccggauc cagaaacgga   1620 accggggugga ccagaaugac aagcccuacg ugcugacaaa caagugauaa uaggcuggag   1680 ccucggugc caugcuucuu gccccuuggg ccuccccca gcccucuc cccuuccugc   1740 acccguaccc ccguggucuu ugaauaaagu cugagugggc ggc                    1783
```

<210> SEQ ID NO 16
<211> LENGTH: 1882
<212> TYPE: RNA
<213> ORGANISM: Artificial Sequence
<220> FEATURE:
<223> OTHER INFORMATION: Synthetic Polynucleotide

<400> SEQUENCE: 16

```
gggaaauaag agagaaaaga agaguaagaa gaaauauaag agccaccaug gaauacugga    60
agcacaccaa ccacggcaag gacgccggca acgagcugga aaccagcaca gccacacacg    120
gcaacaagcu gaccaacaag aucaccuaca uccuguggac caucacccug gugcugcuga    180
gcaucguguu caucaucgug cugaccaaua gcaucaagag cgagaaggcc agagagagcc    240
ugcugcagga caucaacaac gaguucaugg aagugaccga aaagauccag guggccagcg    300
acaacaccaa cgaccugauc cagagcggcg ugaacacccg gcugcugacc auccagagcc    360
acgugcagaa cuacauccc aucagccuga cccagcagau cagcgaccug cggaaguuca    420
ucagcgagau caccaccccgg aacgacaacc aggaagugcc ccccagaga aucacccacg    480 acgugggcau caagccccug aacccccgacg auuucuggcg guguacaagc ggccugccca    540
gccugaugaa gacccccaag aucccggcuga ugccuggccc uggacugcug gccaugccua    600
```

```
ccacagugga uggcugugug cggaccccca gccucgugau caacgaucug aucuacgccu    660
acaccagcaa ccugaucacc cggggcugcc aggauaucgg caagagcuac caggugcugc    720
agaucggcau caucaccgug aacuccgacc uggugcccga ccugaacccu cggaucagcc    780
acaccuucaa caucaacgac aacagaaaga gcugcagccu ggcucugcug aacaccgacg    840
uguaccagcu gugcagcacc cccaaggugg acgagagaag cgacuacgcc agcagcggca    900
ucgaggauau cgucuggac aucgugaacu acgacgcag caucagcacc acccggauca    960
agaacaacaa caucagcuuc gaccagcccu acgccgcccu guacccuucu gugggcccug   1020
gcaucuacua caagggcaag aucaucuucc ugggcuacgg cggccuggaa cacccau      1080 acgagaacgc caucugcaac accaccggcu gcccuggcaa gacccagaga gacugcaauc   1140
aggccagcca cagcccuggg uucagcgacc gcagaauggu caacucuauc aucguggug    1200 acaagggccu gaacagcgug cccaagcuga aguguggac aaucagcaug cgccagaacu    1260
acuggggcag cgagggcaga cuucugcugc ugggaaacaa gaucuacauc uacacccggu   1320
ccaccagcug gcacagcaaa cugcagcugg gaaucaucga caucaccgac uacagcgaca   1380
uccggaucaa guggaccugg cacaacgugc ugagcagacc cggcaacaau gagugcccuu   1440
ggggccacag cugccccgau ggauguauca ccggcgugua caccgacgcc uaccccuga    1500 auccuaccgg cuccaucgug uccagcguga uccuggacag ccagaaaagc agagugaacc   1560
ccgugaucac auacagcacc gccaccgaga gagugaacga acuggccauc agaaacaaga   1620
cccugagcgc cggcuauacc accacaagcu gcaucacaca cuacaacaag ggcuacugcu   1680
uccacaucgu ggaaaucaac cacaagucc ugaacaccuu ccagcccaug cuguucaaga   1740
ccgagauccc caagagcugc uccugauaau aggcuggagc ucggguggcc augcuucuug   1800
ccccuugggc cucccccag ccccuccucc ccuuccugca cccguacccc cguggucuuu    1860
gaauaaaguc ugaguggggcg gc                                          1882
```

<210> SEQ ID NO 17
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 17

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly
            20                  25                  30

<210> SEQ ID NO 18
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 18

Met Asp Trp Thr Trp Ile Leu Phe Leu Val Ala Ala Ala Thr Arg Val
1               5                   10                  15

His Ser

<210> SEQ ID NO 19
<211> LENGTH: 20

```
<212> TYPE: PRT
<213> ORGANISM: Artificial Sequence
<220> FEATURE:
<223> OTHER INFORMATION: Synthetic Polypeptide

<400> SEQUENCE: 19

Met Glu Thr Pro Ala Gln Leu Leu Phe Leu Leu Leu Leu Trp Leu Pro
1               5                   10                  15

Asp Thr Thr Gly
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 20

Met Leu Gly Ser Asn Ser Gly Gln Arg Val Val Phe Thr Ile Leu Leu
1               5                   10                  15

Leu Leu Val Ala Pro Ala Tyr Ser
            20

<210> SEQ ID NO 21
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 21

Met Lys Cys Leu Leu Tyr Leu Ala Phe Leu Phe Ile Gly Val Asn Cys
1               5                   10                  15

Ala

<210> SEQ ID NO 22
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 22

Met Trp Leu Val Ser Leu Ala Ile Val Thr Ala Cys Ala Gly Ala
1               5                   10                  15

<210> SEQ ID NO 23
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 23 ccrccaugg                                                                  9

<210> SEQ ID NO 24
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 24
```

```
gggauccuac c                                                          11

<210> SEQ ID NO 25
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 25 uuauuuaww                                                             9
```